(12) United States Patent
Bailey et al.

(10) Patent No.: US 10,428,185 B2
(45) Date of Patent: Oct. 1, 2019

(54) THERMOPLASTIC ELASTOMER HYDROGELS

(71) Applicants: Colorado State University Research Foundation, Fort Collins, CO (US); The Regents of the University of Colorado, a Body Corporate, Denver, CO (US)

(72) Inventors: Travis S. Bailey, Fort Collins, CO (US); Chen Guo, Newark, DE (US); Jackson T. Lewis, Fort Collins, CO (US); Kristine Fischenich, Fort Collins, CO (US); Tammy Haut Donahue, Fort Collins, CO (US); Dilanji Wijayasekara, Fort Collins, CO (US); Matthew G. Cowan, Boulder, CO (US); Douglas L. Gin, Longmont, CO (US); Richard D. Noble, Boulder, CO (US)

(73) Assignees: Colorado State University Research Foundation, Fort Collins, CO (US); The Regents of the University of Colorado, a Body Corporate, Denver, CO (US)

( * ) Notice: Subject to any disclaimer, the term of this patent is extended or adjusted under 35 U.S.C. 154(b) by 0 days.

(21) Appl. No.: 15/539,312

(22) PCT Filed: Dec. 5, 2016

(86) PCT No.: PCT/US2016/064956
§ 371 (c)(1),
(2) Date: Jun. 23, 2017

(87) PCT Pub. No.: WO2017/096367
PCT Pub. Date: Jun. 8, 2017

(65) Prior Publication Data
US 2019/0031835 A1    Jan. 31, 2019

Related U.S. Application Data

(60) Provisional application No. 62/263,025, filed on Dec. 4, 2015, provisional application No. 62/281,497, filed
(Continued)

(51) Int. Cl.
*C08J 3/075* (2006.01)
*B01D 69/02* (2006.01)
(Continued)

(52) U.S. Cl.
CPC .............. *C08J 3/075* (2013.01); *B01D 69/02* (2013.01); *B01D 71/76* (2013.01); *B01D 71/80* (2013.01);
(Continued)

(58) Field of Classification Search
CPC ..... C08J 3/075; C08L 53/005; C08L 2201/54; C08L 71/02
See application file for complete search history.

(56) References Cited

U.S. PATENT DOCUMENTS

| | | |
|---|---|---|
| 2002/0159982 A1 | 10/2002 | Bonassar et al. |
| 2003/0232895 A1 | 12/2003 | Omidian et al. |

(Continued)

FOREIGN PATENT DOCUMENTS

| | | |
|---|---|---|
| WO | WO 2015/038577 A1 | 3/2015 |
| WO | WO 2017/096352 A1 | 6/2017 |
| WO | WO 2017/096367 A1 | 6/2017 |

OTHER PUBLICATIONS

Guo C, Bailey TS. Highly distensible nanostrucured elastic hydrogels from AB diblock and ABA triblock copolymer melt blends. Soft Matter (online). Aug. 16, 2010 (retrieved on Jan. 26, 2017 from the internet), vol. 6, issue 19, pp. 4807-4818.
(Continued)

*Primary Examiner* — Mark S Kaucher
(74) *Attorney, Agent, or Firm* — Polsinelli PC

(57) ABSTRACT

Provided herein is a block copolymer hydrogel, comprising a glass formed from a dry blend of polystyrene-poly(ethyl-
(Continued)

ene oxide) diblock copolymer (SO) and polystyrene-poly(ethylene oxide)-polystyrene triblock copolymer (SOS) in a molar ratio from between 95:5 and 1:99 SO/SOS and a liquid medium at a concentration between about 32:1 and about 2:1 liquid medium/SO—SOS by weight. The block copolymer hydrogel has a fatigue resistance to at least 500,000 compression cycles. Also provided are methods for forming the hydrogel.

44 Claims, 38 Drawing Sheets

Related U.S. Application Data on Jan. 21, 2016, provisional application No. 62/306,340, filed on Mar. 10, 2016.

(51) Int. Cl.
| | | |
|---|---|---|
| *B01D 71/80* | (2006.01) | |
| *B01J 13/00* | (2006.01) | |
| *C08L 53/00* | (2006.01) | |
| *H01M 2/16* | (2006.01) | |
| *B01D 71/76* | (2006.01) | |
| *B01D 71/28* | (2006.01) | |
| *B01D 71/52* | (2006.01) | |

(52) U.S. Cl.
CPC ........... *B01J 13/0052* (2013.01); *C08L 53/00* (2013.01); *H01M 2/1653* (2013.01); *B01D 71/28* (2013.01); *B01D 71/52* (2013.01); *B01D 2325/20* (2013.01); *B01D 2325/42* (2013.01); *B01J 2219/00051* (2013.01); *B01J 2219/00162* (2013.01); *C08J 2353/00* (2013.01); *C08J 2453/00* (2013.01); *C08L 2207/04* (2013.01)

(56) References Cited

U.S. PATENT DOCUMENTS

| | | |
|---|---|---|
| 2003/0236513 A1 | 12/2003 | Schwarz et al. |
| 2004/0101518 A1 | 5/2004 | Vacanti et al. |
| 2008/0191200 A1 | 8/2008 | Frisbie et al. |
| 2010/0221614 A1 | 9/2010 | Bertin et al. |
| 2011/0104452 A1 | 5/2011 | Grozea et al. |
| 2015/0110772 A1 | 4/2015 | Scherman et al. |

OTHER PUBLICATIONS

Guo C, Bailey TS. Tailoring mechanical response through coronal layer overlap in tethered micelle hydrogel networks. Soft Matter (online). Aug. 14, 2015 (retrieved on Jan. 26, 2017 from the internet), vol. 11, issue 37, pp. 7345-7355.

International Search Report and Written Opinion, PCT/US2016/064956, dated Feb. 21, 2017.

FIG. 6A 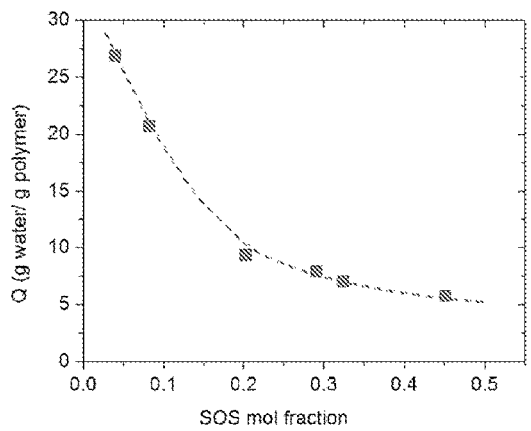 FIG. 6B 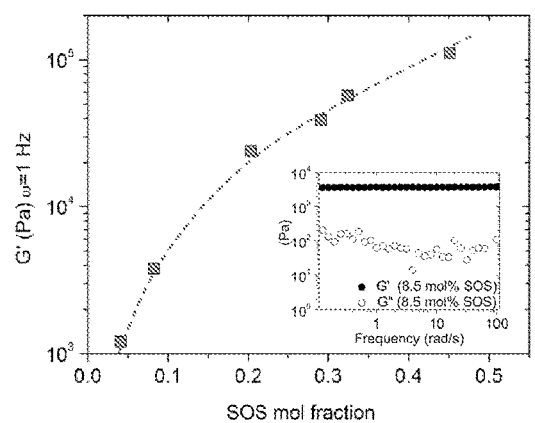
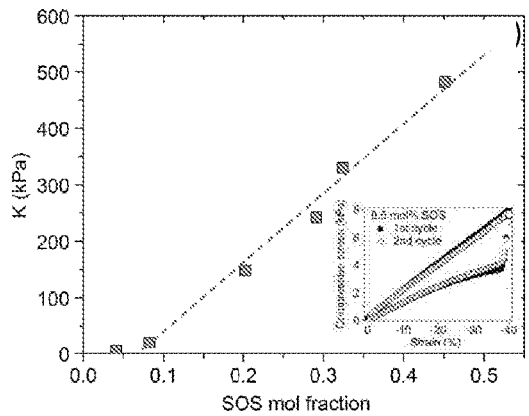 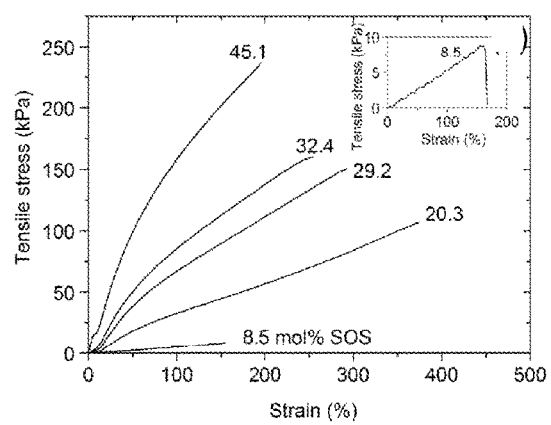
FIG. 6C FIG. 6D
FIG. 6

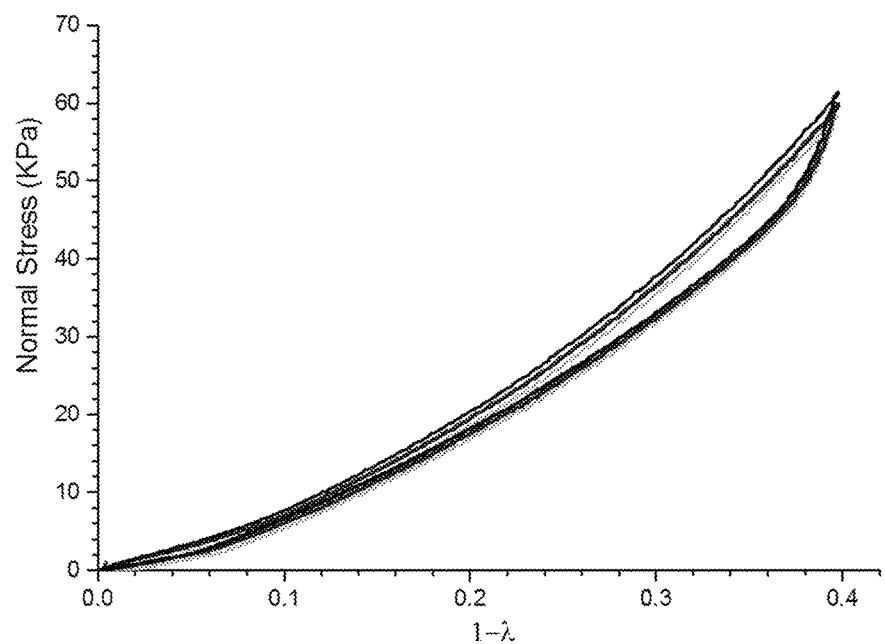
FIG. 30
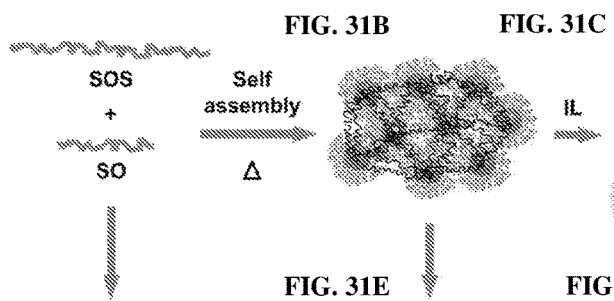
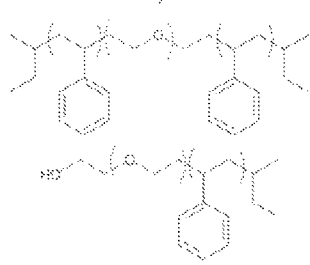
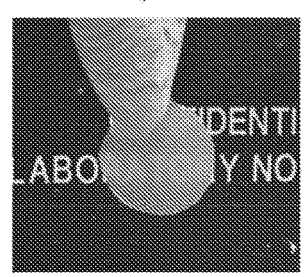
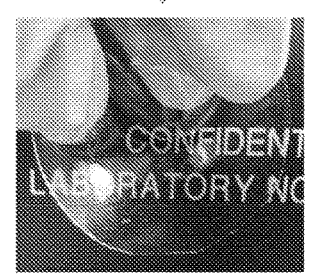

THERMOPLASTIC ELASTOMER HYDROGELS

CROSS-REFERENCE

This application claims the benefit under 35 U.S.C. § 119(e) of U.S. Provisional application Ser. No. 62/263,025 entitled "Mechanically Elastic RTIL Composite Membranes for Efficient Carbon Dioxide Separations from Light Gas Mixtures," filed Dec. 4, 2015; U.S. Provisional application Ser. No. 62/281,497 entitled "Thermoplastic Elastomer Hydrogels," filed Jan. 21, 2016; and U.S. Provisional application Ser. No. 62/306,340 entitled "Thermoplastic Elastomer Hydrogels," filed Mar. 10, 2016, the disclosures of which are herein incorporated by reference in their entireties for all purposes.

GOVERNMENT SUPPORT

This invention was made with government support under Grants CBET1160026 and DMR0645781 awarded by the National Science Foundation; and DE-AR0000098 awarded by the U.S. Department of Energy; and R21 AR069826 awarded by the National Institutes of Health. The government has certain rights in the invention.

TECHNICAL FIELD

Aspects of the present disclosure relate to copolymer blends. More specifically, the present disclosure relates to thermoplastic elastomer hydrogels, which have a high water content while maintaining superior fatigue resistance and modulus recovery.

BACKGROUND

Mechanical performance in hydrogels ranges from very soft and brittle gels to extremely tough and stiff gels, all of which may be widely applied. Conventional hydrogels, such as highly crosslinked polyvinyl alcohols, have been particularly successful in low-load bearing biomedical applications including drug delivery, wound dressings, and injectable fillers, due to their high water content and biocompatibility. The low-load bearing limits of conventional hydrogels are a product of the intrinsic heterogeneity and brittle primary network. During synthesis, the initial differences in reactivity between monomers and crosslinkers create densely crosslinked microgels, which later assemble into macrogels. This inhomogeneous gel formation causes regions of high strain on the polymer system exacerbated during swelling. Thus, the system has few mechanisms available to distribute load effectively, leading to network failure.

Great interest exists for expanding the scope of hydrogel applications in more mechanically demanding environments by bridging the gap between these conventional, weaker hydrogel networks and tough polymeric elastomers. Double network hydrogels (DN) can absorb large amounts of energy and attain a very high modulus but with significant disadvantages. These DN hydrogels compensate for the brittleness and low modulus of conventional single network hydrogels by reinforcing them with a second or third interpenetrating network, introduced at reduced osmotic stress relative to the primary network. In most configurations, a high initial stress state in the primary network produces an enhanced modulus while the secondary and tertiary networks provide enhanced structure and some additional absorption of energy even after the high modulus primary network fails. This method of toughening through additional networks has even been incorporated into non-hydrated elastomers with good success, but is not compatible with fatigue resistance as the primary network is no longer intact for subsequent loading cycles. Like single network hydrogels with low fatigue resistance, the failure mode of the primary network is also correlated to its heterogeneity, leading fragmentation into microgels. These microgels then act as sliding crosslinkers for the secondary network, giving additional energy absorption capabilities, but no longer providing access to the high strain and stress capabilities exhibited under initial loading.

Many advanced applications of hydrogels need to undergo very high levels of cyclic loading. The permanent mechanical fatigue present in many DN and TN gels is incompatible with such applications. Healable primary networks may remedy this issue if incorporated into a DN hydrogel; however, rates of recovery are usually very slow (>12 hours), making them impractical for applications requiring high frequency cyclic loading. There is a long-felt, but unmet need for hydrogel systems that possesses the significant modulus and fatigue resistance (toughness) of such DN and TN systems, while also being able to undergo high levels of cyclic loading without experiencing permanent mechanical fatigue.

SUMMARY

The polymer compositions of the present disclosure include hydrogels that exploit reversible energy absorption to achieve exceptional fatigue resistance, long-term mechanical stability, and elastic recovery ideal for mechanically-demanding applications, particularly those involving repetitive cyclic loading. Sacrificial bond breaking and slow recovery dynamics of most advanced hydrogel systems are avoided. The modular network assembly, including in-situ toughening capabilities, allow the direct tuning of the mechanical properties including elasticity, network mesh density, the uptake of liquid media, mass transfer characteristics, fatigue resistance, strength, and mechanical hysteresis. The assembly of the network uses melt-state fabrication compatible with thermoplastic processing technologies and avoids solution-based crosslinking reactions that limit manufacturing integration.

In one aspect, the present disclosure provides block copolymer hydrogel, comprising a glass formed from a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and a liquid medium at a concentration between about 32:1 and about 2:1 liquid medium/SO—SOS by weight. The block copolymer hydrogel may have a fatigue resistance to at least 500,000 compression cycles.

The molar ratio may be between 80:20 and 1:99 SO/SOS, such as between about 70:30 and about 20:80 SO/SOS. The polystyrene may be a partially or fully hydrogenated polystyrene. The SO—SOS dry blend may be heated to a temperature between about 100° C. and about 180° C. The SO—SOS dry blend may be heated under a pressure between about 50 psig and about 800 psig. The SO—SOS dry blend may be heated for between about 5 minutes and about 50 minutes.

The hydrogel may have a concentration of liquid medium between about 16:1 and about 4:1 liquid medium/SO—SOS by weight. The compression cycles operate with at least 12% compression at a frequency of about 1 Hz. The compression cycles may operate with at least 50% compression at least every eleventh cycle, The fatigue resistance may be characterized by a modulus recoverable to at least 80% of its value before the compression cycles were run, to at least 92% of its value, or to at least 98% of its value.

The liquid medium may be chosen from an aqueous medium, a room-temperature ionic liquid, and combinations thereof. The liquid medium may comprise one or more room-temperature ionic liquids selected from the group consisting of 1-ethyl-3-methyl imidazolium bis(trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis(trifluoromethane)sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([($C_{11}$OH)MIM][TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM][BF4]), 1-(2,3-dihydroxypropyl)-3-alkyl imidazolium bis(trifluoromethane)sulfonimide ([(dhp)MIM][TFSI]), and 1-(2,3-dihydroxypropyl)-3-alkyl imidazolium hexafluorophosphate ([(dhp)MIM][PF6]). The liquid medium may be a room-temperature ionic liquid comprising 1-ethyl-3-methylimidazolium bis(trifluoromethanesulfonyl)imide. The hydrogel may have chain ends of the SO which are functionalized with azide and alkyne groups.

The present disclosure also provides a glass comprising glassy domains having a glass transition temperature of at least 60° C. and comprising crystalline domains, wherein the glass is formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS. The molar ratio may be between about 80:20 and 1:99 SO/SOS, such as between about 70:30 and about 20:80 SO/SOS. The polystyrene may be a partially or a fully hydrogenated polystyrene. The glass may be formed from the SO—SOS dry blend heated to a temperature between about 100° C. and about 180° C. and then allowed to attain ambient temperature. The SO—SOS dry blend may be heated under a pressure between about 50 psig and about 800 psig. The SO—SOS dry blend may be heated for between about 5 minutes and about 50 minutes.

Provided herein is a method for preparing a block copolymer hydrogel. The method comprises: contacting the polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS to form an SO—SOS dry blend; heating SO—SOS dry blend to form an SO—SOS melt; allowing the SO—SOS melt to attain ambient temperature to form an SO—SOS glass; and contacting the SO—SOS glass with a liquid medium to form a block copolymer hydrogel. The block copolymer hydrogels formed by this method may have a fatigue resistance to at least 500,000 compression cycles.

The SO—SOS dry blend may be formed by dissolving the SO and SOS in an organic solvent and removing the organic solvent. The molar ratio may be between about 70:30 and about 20:80 SO/SOS. The SO—SOS dry blend may be heated to a temperature between about 100° C. and about 180° C. The SO—SOS dry blend may be heated under a pressure between about 50 psig and about 800 psig, such as between about 400 psig and about 600 psig. The pressure may be applied to the SO—SOS dry blend mounted within a vacuum bag. The SO—SOS dry blend may be heated for between about 5 minutes and about 50 minutes. Contacting the SO—SOS glass with the liquid medium may occur at a temperature above 0° C. and below about 20° C. The chain ends of the SO may be functionalized with azide and alkyne groups, and the method may further comprises coupling the SO chain ends in the liquid medium to modify the SO/SOS molar ratio.

The compression cycles may operate with at least 12% compression at a frequency of about 1 Hz. The compression cycles may operate with at least 50% compression at least every eleventh cycle. The fatigue resistance may be characterized by a modulus recoverable to at least 80% of its value before the compression cycles were run, such as by a modulus recoverable to at least 98% of its value before the compression cycles were run, such as to at least 98% of its value before the compression cycles were run.

The block copolymer hydrogel may have a liquid medium concentration between about 32:1 and 2:1 liquid medium/SO—SOS by weight, such as between about 16:1 and about 4:1 liquid medium/SO—SOS by weight. The liquid medium may be chosen from an aqueous medium, a room-temperature ionic liquid, and combinations thereof. In particular, the liquid medium may comprise one or more room-temperature ionic liquids selected from the group consisting of 1-ethyl-3-methyl imidazolium bis(trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis(trifluoromethane)sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([($C_{11}$OH)MIM][TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM][BF4]), 1-(2,3-dihydroxypropyl)-3-alkyl imidazolium bis(trifluoromethane)sulfonimide ([(dhp)MIM][TFSI]), and 1-(2,3-dihydroxypropyl)-3-alkyl imidazolium hexafluorophosphate ([(dhp)MIM][PF6]). Specifically, the liquid medium may be a room-temperature ionic liquid comprising 1-ethyl-3-methylimidazolium bis(trifluoromethanesulfonyl)imide.

Provided herein is a membrane, comprising any block copolymer hydrogel described herein. The membrane has a $CO_2/N_2$ selectivities between about 20:1 and about 60:1.

Also provided herein is a battery separator, comprising any block copolymer hydrogel described herein. The battery separator may increase the effective resistance of an electrolyte by a factor of less than about 8, such as a factor less than about 5, or less than about 4. The battery separator may have sufficient porosity to absorb liquid electrolyte for high ionic conductivity, for example as defined by the American Society for Testing and Materials (ASTM) D-2873 or 1294 standard. In some embodiments, the porosity may be at least about 40%, such as at least about 60%, or at least about 80%.

The battery separator may also be chemically stable against electrolyte and electrode material under ordinary battery operation.

BRIEF DESCRIPTION OF THE DRAWINGS

In addition to the exemplary aspects and embodiments described in this disclosure, further aspects and embodiments will become apparent by reference to the drawings and by study of the following descriptions.

FIG. 6. Behavior of baseline SO/SOS hydrogels as a function of SOS triblock copolymer composition. FIG. 6A Swelling ratio (Q). FIG. 6B Elastic modulus (G') under dynamic shear ($\omega$=1 Hz); FIG. 6C Compressive modulus (K) in unconfined compression (strain rate=20% $\min^{-1}$). FIG. 6D Tensile tests, (strain rate=5 mm s$^{-1}$). Insets in FIG. 6B and FIG. 6C describe the dynamic frequency sweep and unconfined compression data for the baseline SO/SOS hydrogel containing 8.5 mol % SOS triblock copolymer. The inset in FIG. 6D provides a zoomed representation of the 8.5 mol % SOS hydrogel.

FIG. 10. Unconfined compression testing results showing stress (kPa) vs. extension ratio of swollen hydrogels of three distinct SOS blends (22, 46, and 72 mol %).

FIGS. 14(C-F) SOS61 held with tweezers. Elastomer-like bending (SOS61). Twisting ability (SOS30) from left to right.

FIG. 30. Cyclic compression loading on SOS46. Stress strain curves for the cycles 2-9 were overlaid.

FIG. 31. Membrane fabrication. FIG. 31A Cartoon representation of polystyrene-b-poly(ethylene oxide)-polystyrene triblock (SOS) and polystyrene-b-poly(ethylene oxide) diblock (SO). FIG. 31B Chemical structure of SOS and SO. FIG. 31C Melt state self-assembly of SO/SOS blend with heat; polystyrene blocks in spherical domains with poly(ethylene oxide) coronas and tethers (highlighted in bold). FIG. 31D Melt-pressed film before RTIL loading. FIG. 31E Swelling of self-assembled film in RTIL with preservation of tethered spherical morphology. FIG. 31F Example of an elastic free-standing membrane of SOS46 loaded with 94 wt % RTIL.

FIG. 34. Mechanical response of SOS22 and SOS46 swollen to equilibrium dimensions in [EMIM][TFSI]. All data were collected at 20° C.

DETAILED DESCRIPTION

Figure 1:
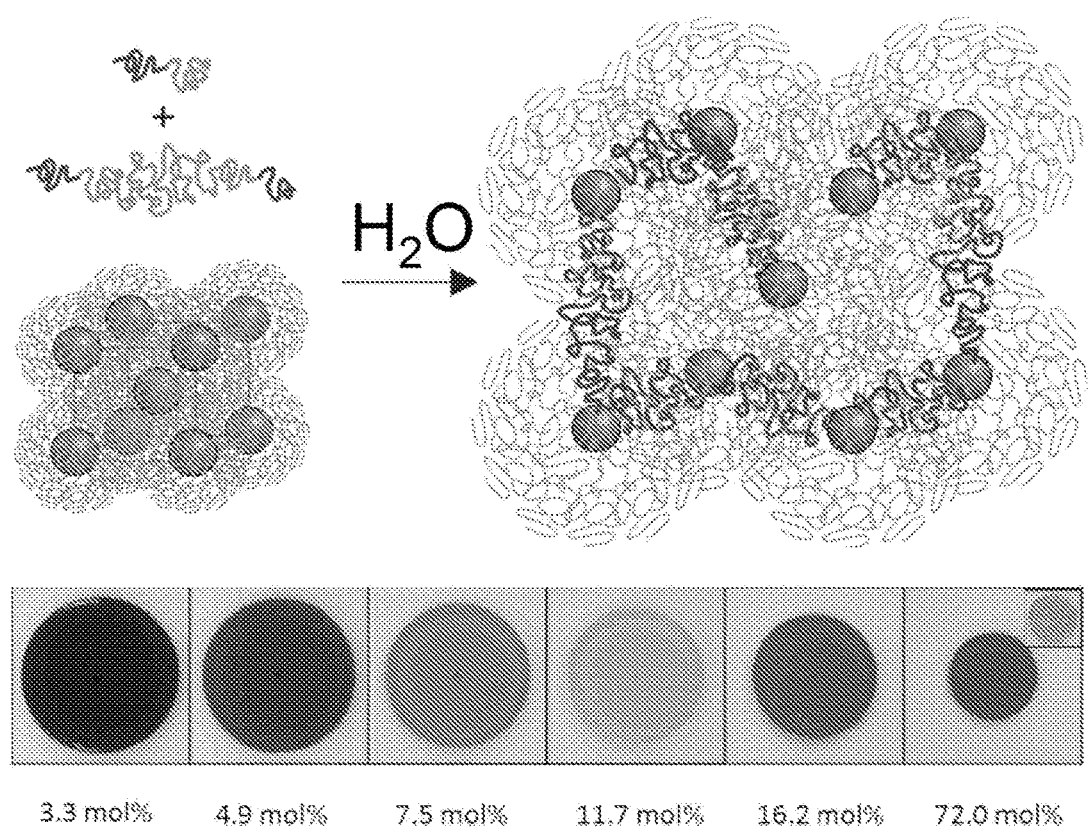
FIG. 1. Generalized fabrication strategy for block copolymer based hydrogels based on sphere-forming SO diblock and SOS triblock copolymer blends. Constituent block copolymers are pre-assembled in the melt and vitrified prior to swelling. SOS triblock copolymer (in bold) acts to tether adjacent spherical PS domains. The change in the amount of SOS triblock copolymer is labeled in mol %.

The present disclosure may be understood by reference to the following detailed description, taken in conjunction with the drawings as described above.

Provided herein is a method for fabricating elastomeric, mechanically tunable hydrogels using blends of melt processable, sphere-forming amphiphilic block copolymers. The processed solid is easily swollen in liquid media to give hydrogels exhibiting excellent mechanical properties and outstanding fatigue resistance. "Hydrogel" as used herein refers to a gel (substantially dilute cross-linked system) in which the liquid component is a liquid medium comprising an aqueous medium, a room-temperature ionic liquid (RTIL), or combinations thereof.

The swellable polymer network is produced by using melt-state self-assembly of blends of poly(A)-block-poly(B) or AB diblock copolymers, with ABA triblock copolymers, synthetically designed to thermodynamically adopt a sphere morphology during microphase separation of the blocks. Each spherical aggregate contains a number of block copolymer chains, depending on the overall molecular weight of the block copolymer and its composition. Mass fractions of A block in the 0.05 to 0.20 range typically formed spherical aggregates during microphase separation in melt-state, with the A block (known as the minority component) forming a spherical core, and the B block forming a coronal brush-like layer coating that core. Spherical aggregates can contain from 100 to 400 A block chains, depending on molecular weight and composition of the AB diblock copolymer. In any specific system, the number of chains in an aggregate is fairly constant, providing aggregates with very narrow size distributions.

Core diameters typically range between 5 nm and 40 nm, depending on the molecular weight and composition of the specific block copolymer. The core diameters were centered about a mean value plus or minus a couple nanometers, with the breadth of this distribution narrowing with increased annealing time in the melt. The ABA triblock copolymer tethered the spherical aggregates and formed the network. ABA triblock copolymer compositions with greater than 17 mol % impart exceptional fatigue resistance. Changing the B block lengths in the ABA triblock copolymer enhanced swelling and improved modulus. The in-situ formation of dangling-end double networks using functionalized AB diblock copolymer dramatically improves the fatigue resistance and elasticity at low ABA triblock copolymer concentrations.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification, the drawings, the chemical structures, and descriptions, which forms a part of this disclosure. Any description of any R-group or chemical substituent, alone or in any combination, may be used in any chemical Formula described herein, and Formulae include all conformational and stereoisomers, including diastereomers, epimers, and enantiomers. Moreover, any feature of a copolymer disclosed herein may be used in combination with any other feature of a copolymer disclosed herein, including but not limited to the physical properties of the copolymer, properties of the guest molecule disposed therein or thereupon, or any intermediate structures, metastructures or combinations.

(a) Thermoplastic Elastomeric Hydrogels

The present disclosure provides block copolymer hydrogel, comprising a glass formed from a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and a liquid medium at a concentration between about 32:1 and about 2:1 liquid medium/SO—SOS by weight. The block copolymer hydrogel may have a fatigue resistance to at least 500,000 compression cycles.

Block copolymer-based hydrogels have a regular structure attained through self-assembly in the melt state, leading to a more homogeneous network formation. This non-solution based thermally processable gel formation allowed the hydrogel to be shaped before swelling, giving it many industrial advantages of plastics, such as die-casting and coating capabilities. Also, blending relative amounts of the two constituents tuned the mechanical properties of the gel through a large range.

The two-component polystyrene-poly(ethylene oxide) diblock (SO) and polystyrene-poly(ethylene oxide)-polystyrene triblock (SOS) copolymer-based hydrogel system does not form through chemical crosslinkers like conventional brittle hydrogels. Instead, self-assembly of block copolymers into micellar domains in the melt state physically crosslinked the polystyrene cores through the SOS tethers (FIG. 1). This formation produced far fewer fixed junction points than found in most crosslinked hydrogels.

For example, the molecular weight between fixed junction points in a typical crosslinked PVA hydrogel is about $10^3$-$10^4$, where the present hydrogel allows a molecular weight of more than $10^5$ between crosslinks, creating a high degree of mobility within the system and allowing energy absorption without straining the polymer chains. Energy absorption was typically facilitated through extensive chain stretching and the recoverable sliding of topologically constrained entanglements in the O block of the SOS triblock tethers. Additionally, the dynamic and transient entanglements of the O chains in the SO diblock copolymer with other chains in the swollen O matrix could reversibly absorb energy through chain reptation without breaking bonds.

(i) SO—SOS Glass

The block copolymer hydrogels described herein comprise a glass formed from a dry blend comprising diblock copolymer and a copolymer in a molar ratio from between 95:5 and 1:99 diblock to triblock copolymer. In some embodiments, the block copolymer hydrogels described herein comprise a glass formed from a dry blend comprising polystyrene-poly(ethylene oxide) diblock copolymer (SO) and polystyrene-poly(ethylene oxide)-polystyrene triblock copolymer (SOS) in a molar ratio from between 80:20 and 1:99 SO/SOS. The polystyrene blocks may be hydrogenated, for example to polycyclohexylethlene (PCHE).

As used herein, "glass" refers to completely vitrified solids as well as to partially crystalline or glassy solids. Generally, a "glass" is a material below its glass transition temperature ($T_g$), as defined by for example differential scanning calorimetry (DSC) or dynamic mechanical analysis (DMA). Use temperatures defined as a range include all temperatures in which the swelling medium remains in the liquid phase. For aqueous media this may have a range including 0-100° C. For room temperature ionic liquids, as described herein, this may have a range from 0-160° C. Typically, the glassy domains may have a glass transition temperature of at least 60° C.

Thermoplastic elastomer (TPE) hydrogels described herein possessed fatigue resistance (toughness) and elasticity not typically found in processable, physically crosslinked hydrogels. These TPE hydrogels were fabricated by melt blending sphere-forming AB diblock and ABA triblock copolymers followed by vitrifying or chemical cross-linking of the isolated spherical domains of block A which form during the self-assembly process (FIG. 1). Each sphere comprised several hundred minority component (A) blocks, which were necessarily (by block connectivity) enveloped by a dense brush of equal number majority component (B) blocks, giving rise to the micelle-like appearance. Without solvent present, a highly regular and periodic lattice of densely packed micelles was produced. Vitrifying or cross-linking the interior spherical domain (A blocks) allowed one to completely preserve the melt state self-assembled structure both on the micro- and macroscale. Upon selectively hydrating the majority component (B blocks), the lattice of micelles expanded as liquid medium penetrated the dense coronal brush layer of each micelle.

The ABA triblock copolymer, even at small quantities, tethers individual micelles together into an infinite network. Each sphere was a junction point in physically cross-linked system. Equilibrium swelling dimensions were determined by the balance of osmotic swelling forces, entropic restoring forces contributed by the ABA tethering midblocks, and the quantity of topological ABA entanglements produced within the network (FIG. 1) during self-assembly. Generally, the A blocks are a polystyrenic block, such as polystyrene or polycyclohexylethylene. The B blocks are a polyether, such as polyethylene oxide (PEO).

Unexpectedly, at low SOS concentrations the most elastic modulus was produced not by the tethering concentration itself, but through the overlap in the PEO coronal brush layers imposed by the topologically constrained entanglements in the tethers. Without wishing to be bound by theory, the dynamic (non-topologically constrained) entanglements among the dangling PEO chain ends appeared to be responsible for a considerable fraction of the mechanical response under small-strain dynamic shear.

The homogeneous structure provided by melt-state self-assembly of macromolecular block copolymers produced a primary or first network that was quite tough compared with most hydrogel systems. These networks could absorb strains elastically to a few hundred percent, with the exact modulus exhibited tunable through the triblock copolymer content in the original melt-state blend. However, installing a second network of tethers that, instead of altering the mechanical performance directly, remained largely passive under small strain conditions could increase fatigue resistance dramatically. Without wishing to be bound by theory, the secondary network of tethers was only actively engaged when the primary network approaches its strain limitations, thereby improving the high strain fatigue resistance of the hydrogel without impacting the smaller strain mechanical response of the primary network. Adding this second network of tethers could also be done without sacrificing the thermoprocessibility of the system.

The large number of hydroxyl-terminated diblock copolymers comprising each micellar domain could be exploited. For example, the hydroxyl groups may be activated with leaving groups, such as mesyl or tosyl, or activated with a strong base, such as sodium hydride. The activated hydroxyl groups may then be converted to pairs of orthogonal groups, such as alkynes and azides. These orthogonal groups can react with each other within the polymer, such as in a 1,3-dipolar Huisgen cycloaddition between the azide and alkyne to form a 1,2,3-triazole. The Huisgen cycloaddition is also called the "click reaction." Using orthogonal chemistry, excess diblock copolymer could be coupled to form additional triblock copolymer in situ after the hydrogel has already reached equilibrium.

Not wishing to be bound by theory, the triblock copolymer added in the original melt blend and that which formed via Cu(I)-catalyzed Huisgen coupling between azide and alkyne terminal groups in the hydrated state were molecularly identical (effectively), but the stress state of these two triblock copolymer populations was significantly different. The triblock copolymer present during melt-state self-assembly of the spherical morphology became trapped in its current conformation during sample vitrification. Upon exposure to aqueous media, the entropic restoring force in the tethering midblocks of the triblock copolymer population, combined with topological entanglements present among nearby tethers, precluded infinite swelling and osmotically-driven micelle dispersal. The concentration of topological entanglements scaled with triblock copolymer composition, and dramatically influenced the equilibrium dimensions. Effectively, the osmotic driving force to swell was opposed by an equal and opposite force supplied by the entangled triblock copolymer adjoining the spherical PS domains.

In contrast, triblock copolymer formed through diblock copolymer coupling in the hydrated state at swelling equilibrium produces a population of tethers free of the mechanical stress osmotically imposed on the primary network. Importantly, with the exception of the Cu(I) catalyst specific to this particular choice of chemistry, formation of the DN through the coupling of dangling chain ends lacked leachable small molecule reagents or sol fractions intrinsic to traditional DN hydrogel systems.

The block copolymer may comprise at least one polyalkylene oxide block, especially polyethylene oxide (PEO). The PEO may have an average molecular weight of 3 kDa to 400 kDa. For example, the PEO may have an average molecular weight from about 3 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 35 kDa, from about 35 kDa to about 40 kDa from about 40 kDa to about 45 kDa, from about 45 kDa to about 50 kDa, from about 50 kDa to about 55 kDa, from about 55 kDa to about 60 kDa, from about 60 kDa to about 65 kDa, from about 65 kDa to about 70 kDa, from about 70 kDa to about 75 kDa, from about 75 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 110 kDa to about 115 kDa, from about 115 kDa to about 120 kDa, from about 120 kDa to about 125 kDa, from about 125 kDa to about 130 kDa, from about 130 kDa to about 135 kDa, from about 135 kDa to about 140 kDa, from about 140 kDa to about 145 kDa, from about 145 kDa to about 150 kDa, from about 150 kDa to about 155 kDa, from about 155 kDa to about 160 kDa, from about 160 kDa to about 170 kDa, from about 170 kDa to about 180 kDa, from about 180 kDa to about 190 kDa, from about 190 kDa to about 200 kDa, from about 200 kDa to about 250 kDa, from about 250 kDa to about 300 kDa, from about 300 kDa to about 350 kDa, or from about 350 kDa to about 400 kDa. The PEO may have an average molecular weight of greater than about 100 kDa. The PEO may have an average molecular weight of less than 400 kDa.

The block copolymer may comprise at least one polystyrene block (PS). The PS may have an average molecular weight of 3 kDa to 160 kDa. For example, the PS may have an average molecular weight from about 3 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 35 kDa, from about 35 kDa to about 40 kDa from about 40 kDa to about 45 kDa, from about 45 kDa to about 50 kDa, from about 50 kDa to about 55 kDa, from about 55 kDa to about 60 kDa, from about 60 kDa to about 65 kDa, from about 65 kDa to about 70 kDa, from about 70 kDa to about 75 kDa, from about 75 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 110 kDa to about 115 kDa, from about 115 kDa to about 120 kDa, from about 120 kDa to about 125 kDa, from about 125 kDa to about 130 kDa, from about 130 kDa to about 135 kDa, from about 135 kDa to about 140 kDa, from about 140 kDa to about 145 kDa, from about 145 kDa to about 150 kDa, from about 150 kDa to about 155 kDa, or from about 155 kDa to about 160 kDa. The PS may have an average molecular weight of greater than about 3 kDa. The PS may have an average molecular weight of less than 160 kDa. In particular, the PS may have an average molecular weight between about 5 kDa and about 20 kDa.

Upon heating, the copolymer may form domains of the at least one polystyrene block and of the at least one polyalkylene oxide block with domain sizes from about 5 nm to about 50 nm. For example, the domains may have sizes of about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 35 nm, about 40 nm, about 45 nm, or about 50 nm. The domain size may be greater than about 5 nm. The domain size may be less than 50 nm. In particular, the PEO domain is typically between about 22 nm and about 27 nm. The PS domain is typically between about 18 nm and about 20 nm. At higher molecular weights, the domain size of the PEO domain may be almost 50 nm.

The polystyrene may be partially hydrogenated, yielding cyclohexyl, cyclohexenyl, and cyclohexadienyl moieties. For example, PS domain of the block copolymer may be based on the hydrogenated forms of styrenic monomers, such as vinyl cylcohexylethylene. Hydrogenation may occur under increased partial pressure of hydrogen with or without a catalyst, such as palladium, platinum, rhodium, ruthenium, nickel, or other metal. The catalyst may have a support matrix, such as calcium carbonate ($CaCO_3$), carbon, or porous silica. Suitable examples of hydrogenation catalysts include palladium on carbon, palladium on calcium carbonate, and platinum on porous silica.

The hydroxyl groups of the diblock copolymer may be activated with a leaving group, such as mesyl or tosyl. The activated hydroxyl group may be converted to an azide. The hydroxyl groups of the diblock copolymer may instead be activated with a strong base, such as sodium hydride. The activated hydroxyl group may be converted to any alkyne. When present together in the same hydrogel, the hydroxyl groups of diblock copolymers having alkynes and azides may react together in a Huisgen cycloaddition, resulting in new triblock copolymers formed between the reacted segments within the hydrogel.

In some embodiments, the block copolymer may have an average thickness of about 25 μm to about 100 for example about 25 μm to about 30 about 30 μm to about 35 μm to about 40 about 40 μm to about 45 about 45 μm to about 50 μm, about 50 μm to about 55 about 55 μm to about 60 about 60 μm to about 65 about 65 μm to about 70 about 70 μm to about 75 about 75 μm to about 80 about 80 μm to about 85 about 85 μm to about 90 about 90 μm to about 95 about 95 μm to about 100 In a particular embodiment, the film is about 50 μm thick. The block copolymer may have an average thickness of about 10 μm to about 40 μm, such as between about 10 μm and about 15 μm, between about 15 μm and about 20 μm, between about 20 μm and about 25 μm, between about 25 μm and about 30 μm, between about 30 μm and about 35 μm, or between about 35 μm and about 40 μm. The block copolymer may have an average thickness of about 1 mm to about 5 mm, such as from about 1 mm to about 2 mm, from about 2 mm to about 3 mm, from about 3 mm to about 4 mm, or from about 4 mm to about 5 mm.

(ii) Liquid Medium

The diblock copolymer hydrogel also comprises a liquid medium at a concentration of between about 32:1 and about 2:1 liquid medium/SO—SOS by weight. The liquid medium may be an aqueous medium, a room-temperature ionic liquid (RTIL), a dialkylcarbonate, an alkylenecarbonate, or combinations thereof. The liquid medium may be a liquid electrolyte.

The aqueous medium may be water, a buffer, such as phosphate-buffered saline (PBS) or Ringer's solution, or the like. In particular, the aqueous medium may be buffer. In other embodiments, the aqueous medium may be water.

The liquid medium may be a room-temperature ionic liquid (RTIL), which are relatively non-volatile, highly tunable molten salts whose melting points are below ambient temperature. RTILs are solvents with low viscosities (10-100 cP), low melting points, a range of densities, and relatively small molar volumes. Generally, RTILs consist of a cation and an anion.

The cation in the RTIL may be imidazolium, phosphonium, ammonium, and pyridinium. In particular embodiments, the RTIL comprises an imidazolium cation; that is, the RTIL is an imidazolium-based ionic liquid. Each cation may be substituted with one or more R groups, such as an imidazolium having the formula [Rmim] or [$R_2$mim], wherein "mim" references the imidiazolium. The R group may comprise one or more n-alkyl, branched alkyl, alkenyl, such as vinyl or allyl, alkynyl, fluoroalkyl, benzyl, styryl, hydroxyl, ether, amine, nitrile, silyl, siloxy, oligo(ethylene glycol), isothiocyanates, and sulfonic acids. In particular, the R group may be an alkyl selected from methyl or ethyl.

The RTIL may be functionalized with one, two, three, or more oligo(alkylene glycol) substituents, such as an oligo (ethylene glycol). Alternatively, the oligo(alkylene glycol) may be a methylene glycol or a propylene glycol.

A vicinal diol substituent on the RTILs may provide greater aqueous solubility and possible water miscibility.

Polymerizable RTILs may be provided choosing one or more R groups on the cation from a styrene, vinyl, allyl, or other polymerizable group.

Examples of suitable cations in the RTIL include, but are not limited to, 1-ethyl-3-methyl imidazolium ([EMIM]), 1-hexyl-3-methyl imidazolium ([HMIM]), 1-vinyl-3-ethyl-imidazolium ([VEIM]), 1-allyl-3-methyl-imidazolium ([AMIM]), 1-hexyl-3-butyl-imidazolium ([HBIM]), 1-vinyl-3-methylimidazolium ([VMIM]), 1-hydroxyundecanyl-3-methylimidazolium ([($C_{11}$OH)MIM]), tetrabutylphosphonium ([P4444]), 1-(2,3-dihydroxypropyl)-alkyl imidazolium ([(dhp)MIM]), and combinations thereof. For example, the cation may be 1-ethyl-3-methyl imidazolium ([EMIM]). The cation may be 1-hexyl-3-methyl imidazolium ([HMIM]). The cation may be 1-vinyl-3-ethyl-imidazolium ([VEIM]). The cation may be 1-allyl-3-methyl-imidazolium ([AMIM]). The cation may be 1-hexyl-3-butyl-imidazolium ([HBIM]), 1-vinyl-3-methylimidazolium ([VMIM]). The cation may be 1-hydroxyundecanyl-3-methylimidazolium ([($C_{11}$OH)MIM]). The cation may be tetrabutylphosphonium ([P4444]). The cation may also be 1-(2,3-dihydroxypropyl)-alkyl imidazolium ([(dhp)MIM]).

Suitable anions (X) in the RTIL include, but are not limited to, triflate (OTf), dicyanamide (DCA), tricyanomethanide (TCM), tetrafluoroborate (BF4), hexafluorophosphate (PF6), taurinate (Tau), and bis(trifluoromethane)sulfonimide (TSFI). For example, the anion may be triflate (OTf). The anion may be dicyanamide (DCA). The anion may be tricyanomethanide (TCM). The anion may be tetrafluoroborate (BF4). The anion may be hexafluorophosphate (PF6). The anion may be taurinate (Tau). The anion may be bis(trifluoromethane)sulfonimide (TSFI).

Any combination of cations and anions described herein may be used to form a suitable RTIL. Examples of suitable RTILs include, but are not limited to, 1-ethyl-3-methyl imidazolium bis(trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis (trifluoromethane)sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([($C_{11}$OH)MIM][TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM][BF4]), 1-(2,3-dihydroxypropyl)-3-alkyl imidazolium bis(trifluoromethane)sulfonimide ([(dhp)MIM][TFSI]), 1-(2,3-dihydroxypropyl)-3-alkyl imidazolium hexafluorophosphate ([(dhp)MIM][PF6]), or combinations thereof.

For example, the RTIL may be 1-ethyl-3-methyl imidazolium bis(trifluoromethane)sulfonamide ([EMIM][TFSI]). The RTIL may be 1-hexyl-3-methyl imidazolium bis(trifluoromethane)sulfonamide ([HMIM][TFSI]). The RTIL may be 1-vinyl-3-ethyl-imidazolium bis(trifluoromethane)sulfonamide ([VEIM][TFSI]). The RTIL may be 1-allyl-3-methyl-imidazolium bis(trifluoromethane)sulfonamide ([AMIM][TFSI]). The RTIL may be 1-hexyl-3-butyl-imidazolium bis(trifluoromethane)sulfonamide ([HBIM][TFSI]). The RTIL may be 1-vinyl-3-methylimidazolium bis(trifluoromethane)sulfonamide ([VMIM][TFSI]). The RTIL may be 1-hydroxyundecanyl-3-methylimidazolium bis(trifluoromethane)sulfonamide ([(C$_{11}$OH)MIM][TFSI]). The RTIL may be 1-ethyl-3-methylimidazolium tricyanomethanide ([EMIM][TCM]). The RTIL may be tetrabutylphosphonium taurinate. The RTIL may be ([P4444][Tau]). The RTIL may be 1-ethyl-3-methylimidazolium dicyanamide ([EMIM][DCA]). The RTIL may be 1-(2,3-dihydroxypropyl)-alkyl imidazolium dicyanamide ([(dhp)MIM][DCA]). The RTIL may be 1-(2,3-dihydroxypropyl)-3-alkyl imidazolium tetrafluoroborate ([(dhp)MIM][BF4]). The RTIL may be 1-(2,3-dihydroxypropyl)-3-alkyl imidazolium bis(trifluoromethane)sulfonimide ([(dhp)MIM][TFSI]). The RTIL may also be 1-(2,3-dihydroxypropyl)-3-alkyl imidazolium hexafluorophosphate ([(dhp)MIM][PF6]). These exemplary RTILs are further illustrated below at Table 1.

TABLE 1

Exemplary RTILs.

| Abbreviation | Chemical Name | Structure |
|---|---|---|
| [EMIM][TSFI] | 1-ethyl-3-methylimidazolium bis(trifluoromethane)sulfonimide | 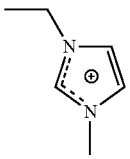 |
| [VEIM][TSFI] | 1-vinyl-3-ethyl-imidazolium bis(trifluoromethane)sulfonimide | 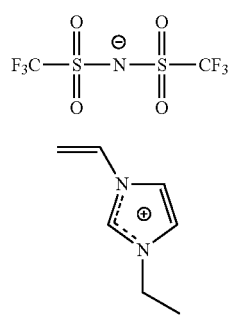 |
| [HMIM][TSFI] | 1-hexyl-3-methyl-imidazolium bis(trifluoromethane)sulfonimide | 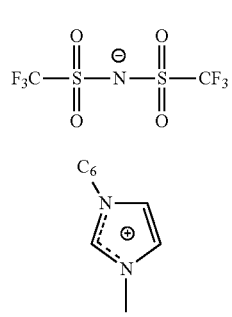 |
| [AMIM][TSFI] | 1-allyl-3-methyl-imidazolium bis(trifluoromethane)sulfonimide | 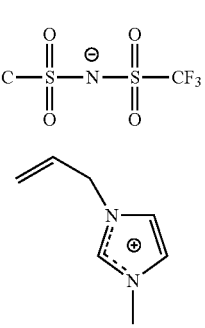 |

TABLE 1-continued

Exemplary RTILs.

| Abbreviation | Chemical Name | Structure |
|---|---|---|
| [HBIM][TSFI] | 1-hexyl-3-butyl-imidazolium bis(trifluoromethane)sulfonimide | |
| [VMIM][TSFI] | 1-vinyl-3-methylimidazolium bis(trifluoromethane)sulfonimide | |
| [(C$_{11}$OH)MIM][TSFI] | 1-hydroxyundecanyl-3-methylimidazolium bis(trifluoromethane)sulfonimide | |
| [EMIM][TCM] | 1-ethyl-3-methylimidazolium tricyanomethanide | |
| [P4444][Tau] | tetrabutylphosphonium taurinate | 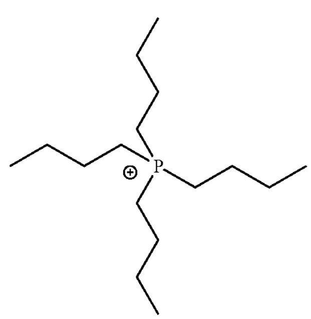 |

TABLE 1-continued

Exemplary RTILs.

| Abbreviation | Chemical Name | Structure |
|---|---|---|
| [EMIM][DCA] | 1-ethyl-3-methylimidazolium dicyanamide | 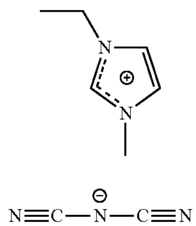 |
| [DMIM][Tf2N] or [DEIM][Tf2N] | 1-(2,3-dihydroxypropyl)-3-methylimidazolium bis(trifluoromethanesulfonimide) or 1-(2,3-dihydroxypropyl)-3-ethylimidazolium bis(trifluoromethanesulfonimide) | 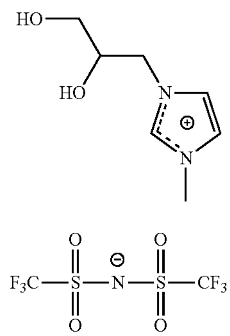 |
| [DMIM][BF4] or [DEIM][BF4] | 1-(2,3-dihydroxypropyl)-3-methylimidazolium tetrafluoroborate or 1-(2,3-dihydroxypropyl)-3-ethylimidazolium tetrafluoroborate | 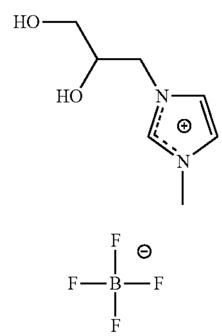 |
| [DMIM][DCA] or [DEIM][DCA] | 1-(2,3-dihydroxypropyl)-3-methylimidazolium dicyanamide or 1-(2,3-dihydroxypropyl)-3-ethylimidazolium dicyanamide | 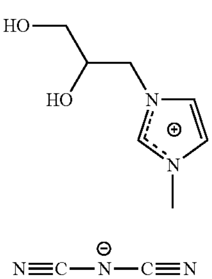 |
| [DMIM][PF6] or [DEIM][PF6] | 1-(2,3-dihydroxypropyl)-3-methylimidazolium hexafluorophosphate or 1-(2,3-dihydroxypropyl)-3-ethylimidazolium hexafluorophosphate | 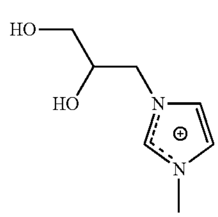 |

TABLE 1-continued

Exemplary RTILs.

| Abbreviation | Chemical Name | Structure |
| --- | --- | --- |
| | | $PF_6^-$ |

The RTIL may be [Rmim][TSFI]. In particular, the RTIL may be [Rmim][TSFI], wherein R is ethyl; that is, the RTIL may be 1-ethyl-3-methylimidazolium bis(trifluoromethanesulfonyl)imide ([EMIM][TSFI]).

The liquid medium may comprise a dialkylcarbonate. Dialkylcarbonates have the general formula RO—C(O)—OR', were R and R' are independently alkyl and are not taken together to form a cyclic ring. In some embodiments, the alkyl selected from the group consisting of methyl, ethyl, propyl, isopropyl, n-butyl, isobutyl, sec-butyl, and tert-butyl. In other embodiments, the alkyl is optionally substituted with one or more alkyl, alkoxyl, or hydroxy groups. Examples of suitable dialkylcarbonates include dimethylcarbonate, ethylmethylcarbonate, diethyl carbonate, ethylpropylcarbonate, methylpropyl carbonate, dipropylcarbonate, butyl ethylcarbonate, butylpropylcarbonate, butylmethylcarbonate, and dibutylcarbonate. The liquid medium may be dimethylcarbonate (DMC). The liquid medium may be diethyl carbonate (DEC)

The liquid medium may comprise an alkylenecarbonate. Alkylenecarbonates have the general formula RO—C(O)—OR', were R and R' are alkyl and taken together to form a cyclic ring. In some embodiments, the alkylene are selected from the group consisting of ethylene, propylene, isopropylene, n-butylene, isobutylene, sec-butylene, and tert-butylene. In other embodiments, the alkylene is optionally substituted with one or more alkyl, alkoxyl, or hydroxy groups. Examples of suitable alkylenecarbonates include ethylenecarbonate, propylenecarbonate, and butylenecarbonate. The liquid medium may be ethylene carbonate (EC). The liquid medium may be propylene carbonate (PC).

The liquid medium may be a liquid electrolyte. The liquid electrolyte may comprise dialkylcarbonate, alkylenecarbonate, or combination thereof. The liquid electrolyte may further comprise a lithium salt, such as lithium perchlorate or lithium hexafluorophosphate. Suitable liquid electrolytes include, but are not limited to, 1 M lithium perchlorate ($LiClO_4$) in ethylenecarbonate/diethylcarbonate/dimethylcarbonate (EC/DEC/DMC, 1:1:1 by volume), 1 M lithium hexafluorophosphate ($LiPF_6$) in ethylenecarbonate/diethylcarbonate (EC/DEC, 1:1 by volume), 1 M lithium hexafluorophosphate ($LiPF_6$) in dimethylcarbonate (DMC), dimethylcarbonate, diethylcarbonate, and propylenecarbonate. The liquid electrolyte may be 1 M lithium perchlorate ($LClO_4$) in ethylenecarbonate/diethylcarbonate/dimethylcarbonate (EC/DEC/DMC, 1:1:1 by volume). The liquid electrolyte may be 1 M lithium hexafluorophosphate ($LiPF_6$) in ethylenecarbonate/diethylcarbonate (EC/DEC, 1:1 by volume). The liquid electrolyte may be 1 M lithium hexafluorophosphate ($LiPF_6$) in dimethylcarbonate (DMC). The liquid electrolyte may be dimethylcarbonate. The liquid electrolyte may be diethylcarbonate. The liquid electrolyte may be propylenecarbonate.

The liquid medium may be a mixture of an aqueous medium and an RTIL. For such mixtures, the volume ratio may be between about 99:1 and about 1:99 aqueous medium/RTIL, such as between about 99:1 and about 95:5 aqueous medium/RTIL, between about 95:5 and about 90:10 aqueous medium/RTIL, between about 90:10 and about 85:15 aqueous medium/RTIL, between about 85:15 and about 80:20 aqueous medium/RTIL, between about 80:20 and about 75:25 aqueous medium/RTIL, between about 75:25 and about 70:30 aqueous medium/RTIL, between about 70:30 and about 65:35 aqueous medium/RTIL, between about 65:35 and about 60:40 aqueous medium/RTIL, between about 60:40 and about 55:45 aqueous medium/RTIL, between about 55:45 and about 50:50 aqueous medium/RTIL, between about 50:50 and about 55:45 aqueous medium/RTIL, between about 55:45 and about 45:65 aqueous medium/RTIL, between about 45:65 and about 40:60 aqueous medium/RTIL, between about 40:60 and about 35:65 aqueous medium/RTIL, between about 35:65 and about 30:70 aqueous medium/RTIL, between about 30:70 and about 25:75 aqueous medium/RTIL, between about 25:75 and about 20:80 aqueous medium/RTIL, between about 20:80 and about 15:85 aqueous medium/RTIL, between about 15:85 and about 10:90 aqueous medium/RTIL, between about 10:90 and about 5:95 aqueous medium/RTIL, or between about 5:95 and about 1:99 aqueous medium/RTIL. In particular, the molar ratio may between about 70:30 and about 20:80 aqueous medium/RTIL, between about 60:40 and about 30:70 aqueous medium/RTIL, or at about 40:60 aqueous medium/RTIL.

Generally, the block copolymer hydrogel may have a water concentration between about 32:1 and 2:1 water/SO—SOS by weight, such as between about 32:1 to 30:1 water/SO—SOS by weight, between about 30:1 to 28:1 water/SO—SOS by weight, between about 28:1 to 26:1 water/SO—SOS by weight, between about 26:1 to 24:1 water/SO—SOS by weight, between about 24:1 to 22:1 water/SO—SOS by weight, between about 22:1 to 20:1 water/SO—SOS by weight, between about 20:1 to 18:1 water/SO—SOS by weight, between about 18:1 to 16:1 water/SO—SOS by weight, between about 16:1 to 14:1 water/SO—SOS by weight, between about 14:1 to 12:1 water/SO—SOS by weight, between about 12:1 to 10:1 water/SO—SOS by weight, between about 10:1 to 8:1 water/SO—SOS by weight, between about 8:1 to 6:1 water/SO—SOS by weight, between about 6:1 to 4:1 water/SO—SOS by weight, or between about 4:1 to 2:1 water/SO—SOS by weight. The water concentration of the hydrogel may be between about 16:1 and about 4:1 water/SO—SOS by weight.

Generally, the block copolymer hydrogel may have a liquid medium concentration between about 32:1 and 2:1 liquid medium/SO—SOS by weight, such as between about 32:1 to 30:1 liquid medium/SO—SOS by weight, between about 30:1 to 28:1 liquid medium/SO—SOS by weight, between about 28:1 to 26:1 liquid medium/SO—SOS by weight, between about 26:1 to 24:1 liquid medium/SO—

SOS by weight, between about 24:1 to 22:1 liquid medium/ SO—SOS by weight, between about 22:1 to 20:1 liquid medium/SO—SOS by weight, between about 20:1 to 18:1 liquid medium/SO—SOS by weight, between about 18:1 to 16:1 liquid medium/SO—SOS by weight, between about 16:1 to 14:1 liquid medium/SO—SOS by weight, between about 14:1 to 12:1 liquid medium/SO—SOS by weight, between about 12:1 to 10:1 liquid medium/SO—SOS by weight, between about 10:1 to 8:1 liquid medium/SO—SOS by weight, between about 8:1 to 6:1 liquid medium/SO—SOS by weight, between about 6:1 to 4:1 liquid medium/ SO—SOS by weight, or between about 4:1 to 2:1 liquid medium/SO—SOS by weight. The liquid medium concentration of the hydrogel may be between about 16:1 and about 4:1 liquid medium/SO—SOS by weight.

(b) Method of Making the Block Copolymer Material

The present disclosure provides a method for preparing a block copolymer hydrogel. The method comprises contacting polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS to form an SO—SOS dry blend. The SO—SOS dry blend is heated to form an SO—SOS melt. The SO—SOS melt is allowed to attain ambient temperature to form an SO—SOS glass. Then the SO—SOS glass is contacted with a liquid medium to form a block copolymer hydrogel. The resulting block copolymer hydrogel may have a fatigue resistance to at least 500,000 compression cycles.

(i) Blending of the SO—SOS Dry Blend

The SO—SOS dry blend may be formed by dissolving the SO and SOS in an organic solvent and removing the organic solvent. The organic solvent may be a polar protic solvent, a polar aprotic solvent, a non-polar solvent, or combinations thereof. Suitable examples of polar protic solvents include, but are not limited to alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methyl acetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In particular, the solvent may be benzene or toluene.

Before blending, the SOS may be formed by synthesis from SO starting material, and then isolated using iterative fractionation. The solvent used for iterative fractionation may be any organic solvent described herein. In some embodiments, the solvent used is chloroform or n-hexane. The purity of SOS after iterative fractionation may be greater than 95 mol %, such as greater than 98 mol %, or about 99 mol %.

In the SO—SOS dry blend, the molar ratio may be between about 95:5 and about 1:99 SO/SOS, such as between about 95:5 and about 90:10 SO/SOS, such as between about 90:10 and about 85:15 SO/SOS, such as between about 85:15 and about 80:20 SO/SOS, such as between about 80:20 and about 75:25 SO/SOS, such as between about 75:25 and about 70:30 SO/SOS, such as between about 70:30 and about 65:35 SO/SOS, between about 65:35 and about 60:40 SO/SOS, between about 60:40 and about 55:45 SO/SOS, between about 55:45 and about 50:50 SO/SOS, between about 50:50 and about 55:45 SO/SOS, between about 55:45 and about 45:65 SO/SOS, between about 45:65 and about 40:60 SO/SOS, between about 40:60 and about 35:65 SO/SOS, between about 35:65 and about 30:70 SO/SOS, between about 30:70 and about 25:75 SO/SOS between about 25:75 and about 20:80 SO/SOS, between about 20:80 and about 15:85 SO/SOS, between about 15:85 and about 10:90 SO/SOS, between about 10:90 and about 5:95 SO/SOS, or between about 5:95 and about 1:99 SO/SOS. In particular, the molar ratio may between about 70:30 and about 20:80 SO/SOS, between about 60:40 and about 30:70 SO/SOS, or at about 40:60 SO/SOS. The molar ratio may also be about 4:96 SO/SOS, about 3:97 SO/SOS, about 2:98 SO/SOS, or about 1:99 SO/SOS.

(ii) Heating of the SO—SOS Dry Blend

The SO—SOS dry blend is processed under a combination of pressure and heat for a period of time to form an SO—SOS glass. The SO—SOS dry blend may be heated to a temperature between about 100° C. and about 180° C., such as between about 100° C. and about 110° C., between about 110° C. and about 120° C., between about 120° C. and about 130° C., between about 130° C. and about 140° C., between about 140° C. and about 150° C., between about 150° C. and about 160° C., between about 160° C. and about 170° C., or between about 170° C. and about 180° C. The temperature may be between about 140° C. and about 160° C., such as about 150° C.

The SO—SOS dry blend may be heated without or without pressure. If heated under pressure, the SO—SOS dry blend may be heated under a pressure between about 50 psig and about 800 psig, such as between about 50 psig and about 100 psig, between about 100 psig and about 150 psig, between about 150 psig and about 200 psig, between about 200 psig and about 250 psig, between about 250 psig and about 300 psig, between about 300 psig and about 350 psig, between about 350 psig and about 400 psig, between about 400 psig and about 450 psig, between about 450 psig and about 500 psig, between about 500 psig and about 550 psig, between about 550 psig and about 600 psig, between about 600 psig and about 650 psig, between about 650 psig and about 700 psig, between about 700 psig and about 750 psig, or between about 750 psig and about 800 psig. In particular, the pressure may be between about 200 psig and about 600 psig, or at about 500 psig.

Additionally, pressure may be applied to samples of the SO—SOS dry blend placed in a vacuum bag, such that a dynamic reduced pressure of less than 20 Torr inside the bag is achieved during heating. That is, the sample may be placed into a vacuum bag during operation of the press used to heat and squeeze the sample. Doing so has been discovered herein to reduce the number of microbubbles, as well as grain boundary and particle sintering defects in the melt.

The SO—SOS dry blend may be heated for between about 5 minutes and about 50 minutes, such as between about 5 minutes and about 10 minutes, between about 10 minutes and about 15 minutes, between about 15 minutes and about 20 minutes, between about 20 minutes and about 25 minutes, between about 25 minutes and about 30 minutes, between about 30 minutes and about 35 minutes, between about 35 minutes and about 40 minutes, between about 40 minutes and about 45 minutes, or between about 5 minutes and about 50 minutes. In particular, the SO—SOS dry blend may be heated for about 25 minutes, or for about 5 minutes.

The heating may occur in heating-cooling cycles, wherein the dry blend is heated for a period of time and then allowed to cool to ambient temperature before re-heating. For example, the dry blend may be heated for a period of 5 minutes and then allowed to cool to ambient temperature before reheating. Generally, the dry blend may pass through 1 to 10 cycles. Any combination of these features may be used for processing the dry blend. For example, the dry blend may be heated at 150° C. at 500 psig in a vacuum bag for 4 heating-cooling cycles.

As used herein "ambient temperature" is the temperature of the environment surrounding the process or experimental apparatus.

(iii) Swelling and the Liquid Medium

The SO—SOS glass is contacted with a liquid medium to form a block copolymer hydrogel. The liquid medium may be an aqueous medium, a room-temperature ionic liquid (RTIL), a dialkylcarbonate, an alkylenecarbonate, or combinations thereof. For example, any liquid medium described herein may be used.

The SO—SOS glass may be contacted with the liquid medium at a temperature above 0° C. and below about 160° C., such as above 0° C. and below about 20° C., or at about 10° C. The temperature may be between about 0° C. and about 5° C., between about 5° C. and about 10° C., between about 10° C. and about 15° C., between about 15° C. and about 20° C., between about 20° C. and about 25° C., between about 25° C. and about 30° C., between about 30° C. and about 35° C., between about 35° C. and about 40° C., between about 40° C. and about 45° C., between about 45° C. and about 50° C., between about 50° C. and about 55° C., between about 55° C. and about 60° C., between about 60° C. and about 65° C., between about 65° C. and about 70° C., between about 70° C. and about 75° C., between about 75° C. and about 80° C., between about 80° C. and about 85° C., between about 85° C. and about 90° C., between about 90° C. and about 95° C., between about 95° C. and about 100° C., between about 100° C. and about 105° C., between about 105° C. and about 110° C., between about 110° C. and about 115° C., between about 115° C. and about 120° C., between about 120° C. and about 125° C., between about 125° C. and about 130° C., between about 130° C. and about 135° C., between about 135° C. and about 140° C., between about 140° C. and about 145° C., between about 145° C. and about 150° C., between about 150° C. and about 155° C., or between about 155° C. and about 160° C.

The SO—SOS glass may be contacted with the aqueous medium at a temperature above 0° C. and below about 100° C., such as above 0° C. and below about 20° C., at about 10° C. The temperature may be between about 0° C. and about 5° C., between about 5° C. and about 10° C., between about 10° C. and about 15° C., between about 15° C. and about 20° C., between about 20° C. and about 25° C., between about 25° C. and about 30° C., between about 30° C. and about 35° C., between about 35° C. and about 40° C., between about 40° C. and about 45° C., between about 45° C. and about 50° C., between about 50° C. and about 55° C., between about 55° C. and about 60° C., between about 60° C. and about 65° C., between about 65° C. and about 70° C., between about 70° C. and about 75° C., between about 75° C. and about 80° C., between about 80° C. and about 85° C., between about 85° C. and about 90° C., between about 90° C. and about 95° C., or between about 95° C. and about 100° C.

In some embodiments, after swelling, the block copolymer hydrogel may have a concentration of liquid medium between about 32:1 and 2:1 liquid medium/SO—SOS by weight, such as between about 32:1 to 30:1 liquid medium/SO—SOS by weight, between about 30:1 to 28:1 water/SO—SOS by weight, between about 28:1 to 26:1 liquid medium/SO—SOS by weight, between about 26:1 to 24:1 liquid medium/SO—SOS by weight, between about 24:1 to 22:1 liquid medium/SO—SOS by weight, between about 22:1 to 20:1 liquid medium/SO—SOS by weight, between about 20:1 to 18:1 liquid medium/SO—SOS by weight, between about 18:1 to 16:1 liquid medium/SO—SOS by weight, between about 16:1 to 14:1 liquid medium/SO—SOS by weight, between about 14:1 to 12:1 liquid medium/SO—SOS by weight, between about 12:1 to 10:1 liquid medium/SO—SOS by weight, between about 10:1 to 8:1 liquid medium/SO—SOS by weight, between about 8:1 to 6:1 liquid medium/SO—SOS by weight, between about 6:1 to 4:1 liquid medium/SO—SOS by weight, or between about 4:1 to 2:1 liquid medium/SO—SOS by weight. The liquid concentration of the hydrogel may be between about 16:1 and about 4:1 liquid medium/SO—SOS by weight.

In other embodiments, after swelling, the block copolymer hydrogel may have a concentration of water between about 32:1 and 2:1 water/SO—SOS by weight, such as between about 32:1 to 30:1 water/SO—SOS by weight, between about 30:1 to 28:1 water/SO—SOS by weight, between about 28:1 to 26:1 water/SO—SOS by weight, between about 26:1 to 24:1 water/SO—SOS by weight, between about 24:1 to 22:1 water/SO—SOS by weight, between about 22:1 to 20:1 water/SO—SOS by weight, between about 20:1 to 18:1 water/SO—SOS by weight, between about 18:1 to 16:1 water/SO—SOS by weight, between about 16:1 to 14:1 water/SO—SOS by weight, between about 14:1 to 12:1 water/SO—SOS by weight, between about 12:1 to 10:1 water/SO—SOS by weight, between about 10:1 to 8:1 water/SO—SOS by weight, between about 8:1 to 6:1 water/SO—SOS by weight, between about 6:1 to 4:1 water/SO—SOS by weight, or between about 4:1 to 2:1 water/SO—SOS by weight. The water concentration of the hydrogel may be between about 16:1 and about 4:1 water/SO—SOS by weight.

The block copolymer hydrogel may have a fatigue resistance to at least 500,000 compression cycles, such as at least 600,000 compression cycles, such as at least 700,000 compression cycles, such as at least 800,000 compression cycles, such as at least 900,000 compression cycles, such as at least 1,000,000 compression cycles, such as at least 1,500,000 compression cycles, such as at least 2,000,000 compression cycles, such as at least 2,500,000 compression cycles, such as at least 3,000,000 compression cycles, such as at least 3,500,000 compression cycles, such as at least 4,000,000 compression cycles, such as at least 4,500,000 compression cycles, such as at least 5,000,000 compression cycles, or such as at least 10,000,000 compression cycles. In counting the number of compression cycles, the cycles are preferably continuous, but need not be so, having a resting period between shorter runs of cycles.

The compression cycles may operate with at least 12% compression at a frequency of about 1 Hz, particularly wherein the compression cycles operate with at least 50% compression at least every eleventh cycle. The fatigue resistance is characterized by a modulus recoverable to at least 80% of its value before the compression cycles were run, such as to at least 90%, to at least 92%, to at least 95% or to at least 98% of its value before the compression cycles were run.

(c) Applications

The hydrogels may be used as hydrated adhesives, coating materials, elastic separation membranes such as for light gases, protein assemblies and biologics, and mechanical energy absorbers, such that found in footwear, sportswear, helmets and other protective gear, and sports equipment. The hydrogels may also be used as separators in battery cells or fuel cells.

(i) Gas Separation

The hydrogels may be used as elastic separation membranes for light gases, such as mixtures of carbon dioxide ($CO_2$), methane ($CH_4$), ethane, propane, butane, water, oxygen ($O_2$), nitrogen and argon. The mixture of light gases may be crude natural gas (such as that produced at a natural gas well), flue gas, or atmosphere. In particular, $CO_2$ is emitted from coal-fired power plants in "flue gas," which contains 10-15% $CO_2$ along with $N_2$ (70-80%), water, $O_2$, and other trace gases.

Existing technologies for the separation of $CO_2$ from flue gas include aqueous amine scrubbing, pressure swing absorption, and cryogenic distillation. Implementing these technologies requires about 30% of the energy produced by the power plant, making them economically unsustainable. Membrane-based alternatives are being investigated at the pilot plant scale as a superior solution for separating $CO_2$ from flue gas. Successful membrane technologies offer several advantages over traditional methods for lower operating energies, modular scalability, a reduced physical footprint, and elimination of volatile chemicals.

To successfully apply to flue gas separations, membranes must have high $CO_2$ permeance and reasonable $CO_2/N_2$ selectivities ($\geq 20:1$), be processable into substantially defect-free thin films, have long operating lifetimes, and have reasonable production costs. The range of $CO_2/N_2$ selectivities can and will vary. Generally, the selectivity may be between about 20:1 and about 60:1, such as about 20:1 to about 25:1, about 25:1 to about 30:1, about 30:1 to about 35:1, about 35:1 to about 40:1, about 40:1 to about 45:1, about 45:1 to about 50:1, about 50:1 to about 55:1, or about 55:1 to about 60:1. The selectivity may be greater than about 20:1. The selectivity may be less than about 60:1.

New membrane materials may be screened by measuring single-gas permeability and selectivity, which are compared with performance values of existing materials using a comprehensive Robeson Plot, which are used in membrane science to gauge the performance of a membrane relative other materials as well to measure progress in a particular separation over time. Many other critical properties, such as mechanical stability over time, processability into freestanding or stable thin films, and compatibility with current module configurations, may also be addressed.

The $CO_2/N_2$ separation performance of the RTIL-hydrogel membranes disclosed herein was characterized by transmembrane pressure differentials exceeding about 400 kPa. RTIL-hydrogel membranes disclosed herein exhibit figures of merit pushing the limits of the 2008 Robeson plot upper bound, while maintaining exceptional mechanical integrity as a free-standing film, even in the swollen state. Included in this disclosure (Example 21) is an evaluation of the unique tensile and compressive properties of these RTIL hydrogel membranes under cyclic loading conditions, and the extended $CO_2/N_2$ separation performance of these membranes over 28 days. No prior reports have been made of free-standing RTIL-hydrogel membranes prepared from melt-state processing of sphere-forming diblock/triblock copolymer blends swollen with RTIL and subsequently employed for light gas separations. Use of melt-state processing and self-assembly combined with diblock copolymer as a significant blend component, dramatically enhanced RTIL-hydrogel membranes to mechanically compete in $CO_2$/light gas separation.

(ii) Battery Separators

The hydrogels disclosed herein may also be used to make separators in battery cells or fuel cells. The battery separator is a critical component in liquid electrolyte batteries, and is placed between the positive electrode and the negative electrode to prevent physical contact of the electrodes while enabling free ionic transport and isolating electronic flow. Generally, a battery separator is a microporous layer consisting of either a polymeric membrane or a non-woven fabric mat. The battery separators described herein are chemically and electrochemically stable towards the electrolyte and electrode materials under ordinary battery operation. These battery separators are also mechanically strong enough to withstand the high tension during the battery assembly operation.

Structurally, the battery separator has sufficient porosity to absorb liquid electrolyte for the high ionic conductivity. One of skill in the art would recognize that the battery separator adds electrical resistance and takes up space inside the battery, which can adversely affect battery performance. Therefore, selection of an appropriate separator is critical to the battery performance, including energy density, power density, cycle life and safety. The battery separators described herein satisfy these performance criteria. Especially for high energy and power densities, the battery separator must be very thin and highly porous while still remaining mechanically strong. For battery safety, the battery separator may shut the battery down if overheated, such as the occasional short circuit, so that thermal runaway can be avoided. The shutdown function can be obtained through a multilayer design of the battery separator, in which at least one layer melts to close the pores below the thermal runaway temperature and the other layer provides mechanical strength to prevent physical contact of the electrodes.

The function of a battery separator described herein is to prevent physical contact of the positive and negative electrodes while permitting free ion flow. The battery separator itself does not participate in any cell reactions, but its structure and properties considerably affect the battery performance, including the energy and power densities, cycle life, and safety.

The battery separator materials described herein, namely the diblock copolymer hydrogels, are chemically stable against the electrolyte and electrode materials under ordinary battery operation, especially under the strongly reductive and oxidative environments when the battery is fully charged. Meanwhile, the battery separator does not degrade or lose mechanical strength during ordinary battery operation over the typical lifetime of a battery. A method for one of skill in the art to verify chemical stability is by calendar life testing.

The low thickness of the battery separators described herein permits high energy and power densities. Although a low thickness may adversely affect the mechanical strength and safety of the separator, the diblock copolymer hydrogels are strong enough for this application. A thickness of 25.4 μm (1 mil) is the standard for consumer rechargeable batteries. As such, battery separators described herein may have a thickness between about 10 μm and about 40 μm, such as between about 10 μm and about 20 μm, between about 20 μm and about 30 μm, or between about 30 μm and about 40 μm. The battery separators may have a uniform thickness across the area of the separators, thereby aiding long cycle life of the batteries in which it is used. The thickness can be measured using the T411 om-83 method developed under the auspices of the Technical Association of the Pulp and Paper Industry.

The battery separators have an appropriate porosity, which holds sufficient liquid electrolyte for the ionic conductivity between the electrodes. One of skill in the art would recognize that too high porosity may adversely impact the shutdown performance because the pores cannot be closed effectively and the membrane shrinks as it melts or softens. The porosity can be measured using liquid or gas absorption methods according to American Society for Testing and Materials (ASTM) D-2873. Typically, a Li-ion battery separator has a porosity of 40%. Generally, the battery separators described herein have a porosity between about 30% and about 85%, such as between about 30% and 35%, between about 35% and about 40%, between about 38% and 42%, between about 40% and 45%, between about 45% and 50%, between about 50% and 55%, between about 55% and 60%, between about 60% and 65%, between about 65% and 70%, between about 70% and 75%, between about 75% and 80%, or between about 80% and about 85%. In particular, the battery separators described herein may have a porosity of about 40%. The battery separator may have a porosity greater than about 55%. The battery separator may have a porosity less than about 85%.

Generally, the pore size must be smaller than the particle size of the electrode components, including the electrode active materials and the conducting additives. In practical cases, membranes with sub-micron pore sizes are adequate to block the penetration of particles, since the tortuous structure of the pores blocks the particles from reaching the opposite electrode. The distribution and structure of pores can be analyzed using a Capillary Flow Porometer (Porous Materials Inc.) or scanning electron microscopy based on ASTM 1294 standard. In particular, the battery separators described herein have uniform distribution and a tortuous structure of the pores. Without wishing to be bound by theory, these features are both highly desirable since the former ensures a uniform current distribution throughout the separator and the latter suppresses the growth of dendritic lithium.

The battery separators described herein should not limit the electrical performance of the battery. Typically, the battery separator increases the effective resistance of the electrolyte by about 4 to about 5, such as by a factor of at least about 4, or by a factor of at least about 5. The ratio of the resistance of the separator filled with electrolyte divided by the resistance of the electrolyte alone is the MacMullin number. MacMullin numbers as high as 8 have been used in high-power Li-ion batteries. For batteries in hybrid electric vehicles (HEV) and in power tools, the MacMullin number should be lower for the purpose of safety and a long cycle life. Air permeability can be used indirectly to estimate the MacMullin number. Air permeability is expressed by the Gurley value, which is defined as the time for an amount of air to pass through an area of the separator under pressure. The Gurley value can be measured per ASTM D726. When the porosity and thickness of the separators are fixed, the Gurley value reflects the tortuosity of the pores. The separator with uniform permeability aids long cycle life of a battery. Variations in permeability result in uneven current density distribution.

Mechanical strength is characterized by the tensile strength along the machine direction (MD) and the transverse direction (TD) (ASTM D-638), the tear resistance (ASTM D-1004), and the puncture strength (ASTM D-822). These parameters are described by Young's modulus. The separator must be mechanically strong, especially in the MD, and enough to withstand the tension of the winding operation during battery assembly. The puncture strength is defined as the maximum load for a needle to puncture a separator, as can be measured with a tensile tester.

The battery separators described herein may wet easily in the liquid medium and retain the liquid medium permanently (over the typical lifetime of a battery). The former facilitates the process of electrolyte filling in battery assembly and the latter increases cycle life of the battery. There is no generally accepted test for battery separator wettability. Placing a droplet of electrolyte on the separator and observing whether or not the droplet quickly wicks into the battery separator is an easy way to indicate sufficient wettability.

The battery separators lay flat and do not bow or skew when laid out and soaked with liquid medium. The battery separator remain stable in dimensions over a wide temperature range during the typical lifetime of a battery.

When the temperature rises to the softening temperature, the battery separator may shrink, even if the porosity is very low, because of the difference in the density between the crystalline and amorphous phases of polymeric materials. For example, a membrane comprising polyethylene can shrink as much as 10% when exposed to a temperature of 120° C. for only 10 minutes. Thermal shrinkage is minimized in the hydrogels described herein. For a prior art Li-ion battery, the shrinkage should be not more than 5% after 60 min at 90° C. The presently described hydrogels have the advantage of high fatigue resistance. They can be installed in a slightly compressed state, such that volume changes may be accommodated by the separator material expanding or compressing elastically. Thus, contact is maintained with the electrodes over a large range of conditions without damaging the battery separator or causing it to fail.

In a Li-ion battery, the battery separators described herein may be capable of battery shutdown at the temperature below that of thermal runaway, and the shutdown should not result in loss of mechanical integrity; otherwise, the electrodes could come into direct contact and the resulting chemical reactions would then cause thermal runaway. The shutdown characteristics can be examined by differential scanning calorimetry or by observing the resistance change of the electrolyte-soaked membrane with temperature increase. For the PE-PP bilayer separators used currently in current Li-ion batteries, they have ~130° C. shutdown temperature and ~165° C. melting temperature.

Most battery separator cost is in the manufacturing process. The process described herein is cost-effective, in that it reduces the battery separator cost. Many properties above are associated with each other and may be in a trade-off relationship. For example, reducing the separator thickness increases battery energy and power densities, but it may also lower the mechanical strength of the battery separator. In practical applications, one of skill in the art would understand to appropriately weight the requirements above among the performance, safety and cost.

Definitions

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight" and describes the concentration of a particular substance in a mixture or solution.

As used herein, the term "ml/kg" designates milliliters of composition per kilogram of formula weight.

As used herein, the term "monomer" refers to any chemical compound capable of forming a covalent bond with itself or a chemically different compound in a repetitive manner. The repetitive bond formation between monomers may lead to a linear, branched, super-branched, or three-dimensional product. Furthermore, monomers may themselves comprise repetitive building blocks, and when polymerized the polymers formed from such monomers are then termed "block polymers." Monomers may belong to various chemical classes of molecules including organic, organometallic or inorganic molecules. The molecular weight of monomers may vary greatly between about 40 Daltons and 20000 Daltons. However, especially when monomers comprise repetitive building blocks, monomers may have even higher molecular weights. Monomers may also include additional reactive groups.

Contemplated polymers may also comprise a wide range of functional or structural moieties, including aromatic systems, and halogenated groups. Furthermore, appropriate polymers may have many configurations, including a homopolymer, and a heteropolymer. Moreover, alternative polymers may have various forms, such as linear, branched, super-branched, or three-dimensional. The molecular weight of contemplated polymers spans a wide range, typically between 400 Daltons and 400,000 Daltons, and may be greater than 1,000,000 Daltons or more, in some embodiments.

"Wettability" refers to the ability of a liquid, such as water, to spread on a solid surface. "Hydrophilic" and "hygrophilic" refer to an intrinsic or average chemical property of a surface or bulk solid to allow a polar liquid, such as water, to spread on the surface, with typical water contact angles from about 0° to about 90°. "Hydrophobic" refers to an intrinsic or average chemical property of a surface or bulk solid that prevents a polar liquid, such as water, from spreading on the surface, with typical water contact angles from about 90° to about 180°, such as from about 100° to about 150°. When the surface roughness enhances or reduces the hydrophilic or hydrophobic properties of a surface or bulk solid, the effect is "parahydrophilic" or "parahydrophobic," respectively. For very rough surfaces, the enhancement or reduction in hydrophilic or hydrophobic properties of the surface or bulk solid may be very great; the effect is referred to as "superhydrophilic" or "superhydrophobic," respectively. Surface roughness is usually defined on the microscopic or molecular scales. For further definition of wettability and surface classifications, please refer to Marmur, "Hydro-hygro-oleo-omni-phobic? Terminology of wettability classification," *Soft Matter*, 8:6867 (2012), which is incorporated herein by reference in its entirety.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present disclosure or the preferred embodiments(s) thereof, the articles "a", "an", "the" and "said" are intended to mean that there are one or more of the elements. The terms "comprising," "including," and "having" are intended to be inclusive and mean that there may be additional elements other than the listed elements.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the embodiments disclosed herein. Accordingly, the above description should not be taken as limiting the scope of the document.

EXAMPLES

The following examples are included to demonstrate certain embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

Example 1—Synthesis of Hydroxy-Polystyrene ("S—OH")

Purified styrene monomer (120 g, 1.14 mol, 20° C.) was added to a stirring solution of sec-butyl lithium (10.23 mL, 1.3 M in cyclohexane) and dry, air-free cyclohexane (1 L, 20° C.) in a 2-L reaction vessel. The temperature was then raised to 40° C. and stirred continuously for 8 hours. At a reduced pressure of 1 psig, purified ethylene oxide (6.6 g, 0.15 mol, 0° C., liquid) was added to the reaction vessel. The reaction was held at 40° C. for an additional 24 hours, after which excess ethylene oxide was removed from the reactor under constant argon flow. The reaction was terminated by adding methanol (50 mL). The polymer was precipitated in methanol (5 L total), producing a fluffy white solid, and dried under vacuum at room temperature for 48 h (yield 116 g, 97%, $M_n$ 8064 g/mol, PDI=1.03).

Example 2—Synthesis of Polycyclohexylethylene ("PCHE")

Hydroxy-polystyrene (S—OH, 5.0 g) from Example 1 was dissolved in 180 mL of purified cyclohexane in a high-pressure vessel and degassed by bubbling argon through the solution for about 20 minutes. The catalyst was palladium on calcium carbonate ($CaCO_3$, Aldrich, 12.5 g, 2.5:1 catalyst to S—OH-by weight). The reaction mixture was sealed in a high-pressure reactor. The catalyst was placed under vacuum at 100° C. overnight, then activated with 100 psig hydrogen gas ($H_2$) for at least 1 hour at 100° C. The reactor was vented and backfilled three times with argon and left under a positive pressure of argon at 100° C. The S—OH solution was transferred to the sealed reactor, the pressure reduced, and the temperature increased to 120° C. while stirring at about 1500 rpm. The reactor was initially charged with 500 psig Hz, and recharged to 500 psig $H_2$ several times while the reaction proceeded overnight. The catalyst was removed by filtration. The polymer product was precipitated into 1 liter methanol, collected by vacuum filtration, and dried at elevated temperature at about 150° C. under a vacuum for 24 hours. The reaction produced polycyclohexylethylene (PCHE). Instead of $Pd/CaCO_3$, another hydrogenation catalyst may be selected, for example Dow Hydrogenation Catalyst (DHC, 5 wt % Pt supported on wide-pore silica).

Example 3—Synthesis of Hydroxy-polystyrene-b-poly(ethylene oxide) ("SO")

Figure 2:
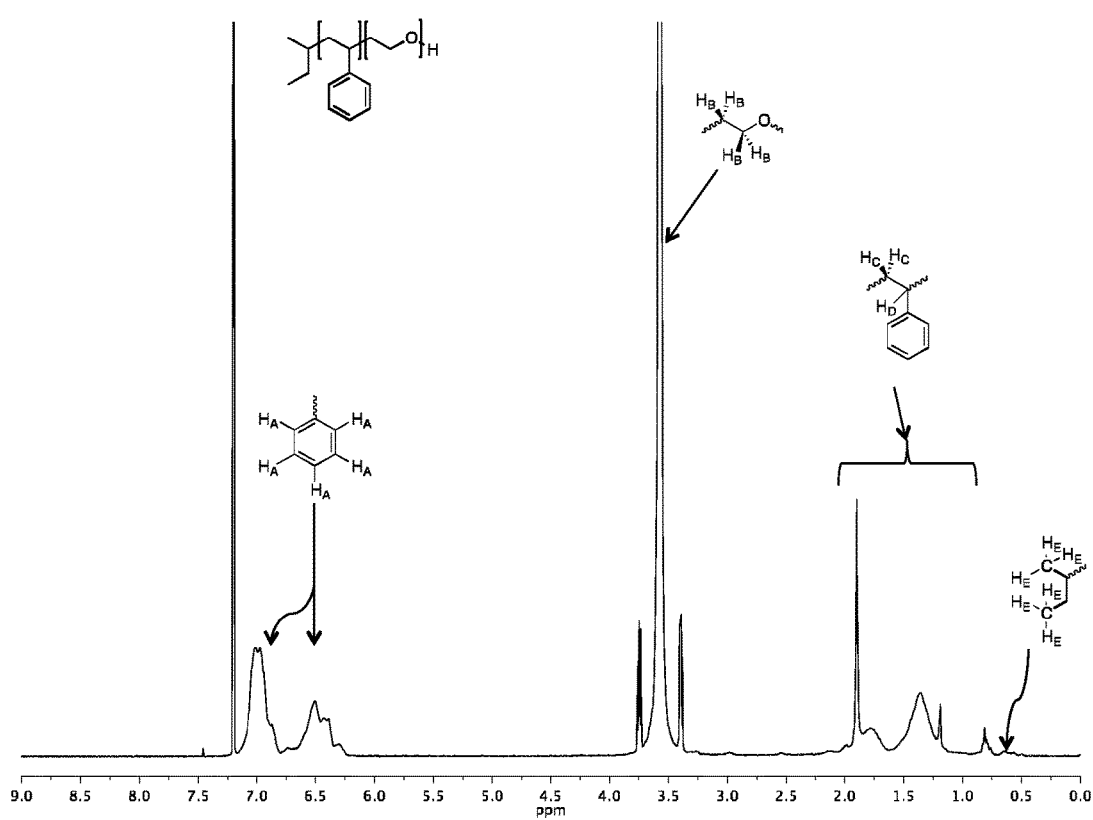
FIG. 2. $^1$H-NMR spectrum of PS—PEO—H diblock copolymer. The PS—PEO—PS triblock copolymer, PS—PEO-azide diblock copolymer, and PS—PEO-alkyne diblock copolymer were all generated from SO diblock copolymer molecule.

Hydroxy-polystyrene (S—OH, 7 g, 1.14 mol) from Example 1 was added to a 2-L reaction vessel containing a glass-coated magnetic stir bar. The reactor was evacuated and backfilled with purified argon (5×) before adding 1 L dry, air-free tetrahydrofuran (THF). Concentrated potassium naphthalenide in THF was added to the polymer solution via cannula until a light green color persisted for 30 minutes. The temperature of the reaction mixture was raised to 40° C. and purified ethylene oxide monomer (78.7 g, 1.78 mol, 0° C.) was added under argon (1 psi) to the stirring solution for 48 hours. The reaction was terminated by methanol (50 mL) and the polymer was precipitated in pentane (4 L), producing a fluffy white solid. The polymer was dried under vacuum at room temperature for 48 hours. The $^1$H-NMR spectrum of hydroxy-polystyrene-b-poly(ethylene oxide) ("PS—PEO diblock copolymer," "PS—PEO—H," or "SO") is shown at FIG. 2. 70,000 g/mol, PDI=1.04).

This reaction may also be performed with polycyclohexylethylene (PCHE) from Example 2.

Example 4—Synthesis of polystyrene-b-poly(ethylene oxide)-b-polystyrene ("PS—PEO—PS," "SOS") Triblock Copolymer Hydroxyl-terminated PS—PEO diblock copolymer (SO) is the parent molecule from which the remaining three block copolymers were derived. SO was prepared via the two-step anionic polymerization of styrene and ethylene oxide described about at Example 3. From this parent diblock copolymer the first of the three derivative molecules, an PS—PEO—PS (SOS) triblock copolymer was synthesized by re-activating the terminal alcohol on SO with potassium naphthalenide and adding α,α'-dibromo-p-xylene over several hours.

Specifically, SO diblock (29 g) from Example 3 was placed into a 2-L round-bottomed reactor. Atmospheric water and oxygen were removed through five successive argon-vacuum backfills with argon pressures reaching 5 psig and vacuum pressures reaching 8-10 mTorr. The SO diblock was allowed to dry under vacuum in the 2-L reactor overnight at 8-10 mTorr. The SO diblock was then dissolved in dry THF. A concentrated potassium naphthalenide solution in dry THF was titrated into the reactor until the solution maintained a green color for 30 minutes.

α,α'-Dibromo-p-xylene in THF (1.5 mL) at a 0.5 molar equivalent to the SO—OH was then injected into the reactor over 12 hours at 0.125 mL/hour using a syringe pump and a 2.5-mL glass syringe. Coupled polymer was precipitated in 5 L pentane followed by vacuum filtration. The precipitated polymer was dried overnight under vacuum to produce a fluffy white solid.

The coupled triblock copolymer product was found to be a 60:40 (mass %) mixture of SOS:SO via SEC peak integration. The SOS triblock copolymer was isolated from this mixture (98+%) via iterative fractionation with chloroform and n-hexane. The temperature was maintained above 40° C. to avoid (non)solvent-induced PEO crystallization. The SOS triblock copolymer ad a molecular weight and contour length essentially double that of the SO diblock copolymers, thereby ensuring domain size compatibility (lattice matching) between the SO and SOS block copolymers during self-assembly. $^1$H-NMR confirmed the targeted volume fraction of polystyrene ($f_S$=0.13), and SEC confirmed the narrow polydispersity of 1.04. A molecular weight ($M_{n,SO}$) of 70,000 kDa was determined using the SEC determined S—OH $M_n$ value of 8390 kDa (PS stds), in combination with the relative block compositions determined using the S—OH $^1$H-NMR peak integrations. SEC: (THF, PS stds): S—OH: $M_{n,S-OH}$=8390 g mol$^{-1}$, $M_w/M_n$=1.03; S—OH: $M_{n,SO}$=70,000 g mol$^{-1}$ (calculated using $M_{n,S-OH}$ (SEC) and S—OH $^1$H NMR), $M_w/M_n$=1.04; SOS: $M_{n,SOS}$=140,000 g mol$^{-1}$ (determined from $2M_{n,SO}$), $M_w/M_n$=1.06; $^1$H NMR (S—OH, SOS): $\delta_H$ (300 MHz; CDCl$_3$): 6.20-7.26 (b, —C$_6$H$_5$,—OCH$_2$(C$_6$H$_4$)CH$_2$O—), 4.55 (s, —OCH$_2$(C$_6$H$_4$) CH$_2$O—), 3.1-4.0 (b, —CH$_2$CH$_2$O—, —CH(C$_6$H$_5$) CH$_2$CH$_2$O—), 1.0-2.30 (b, —CH$_2$CH(C$_6$H$_5$)—, CH$_3$CH (CH$_2$CH$_3$)—, —CH(C$_6$H$_5$)CH$_2$CH$_2$O—), 0.5-0.78 (m, CH$_3$CH(CH$_2$CH$_3$)—).

This reaction may also be performed with SO diblock copolymer from Example 3 using polycyclohexylethylene (PCHE).

Example 5—Fractionation of the SO/SOS Crude Product

SO/SOS polymer recovered from the coupling reaction described at Example 4 produced a coupling efficiency of 52 mol %. Fractionation achieved higher SOS triblock copolymer content (52-87 mol %).

Dry SO/SOS polymer (4 g) was dissolved in chloroform (400 ml) and heated to 45° C. n-hexane (920 ml) was added slowly, keeping the temperature above 40° C. The SOS triblock copolymer precipitated and the solution turned cloudy. Upon cooling to room temperature, the solution turned transparent. The solution contained the majority of the SO diblock copolymer while the SOS triblock copolymer existed as a precipitate, which was vacuum filtered. The SOS triblock precipitate was recovered and allowed to dry under vacuum overnight, while the SO diblock in solution was recovered through rotary evaporation. Different SOS mol % triblock copolymers were achieved through successive fractionations of precipitated SOS copolymers to achieve increasing mol % SOS triblock copolymers.

Example 6—SOS Triblock Copolymer Mol % Calculations from GPC Plots

Figure 3:
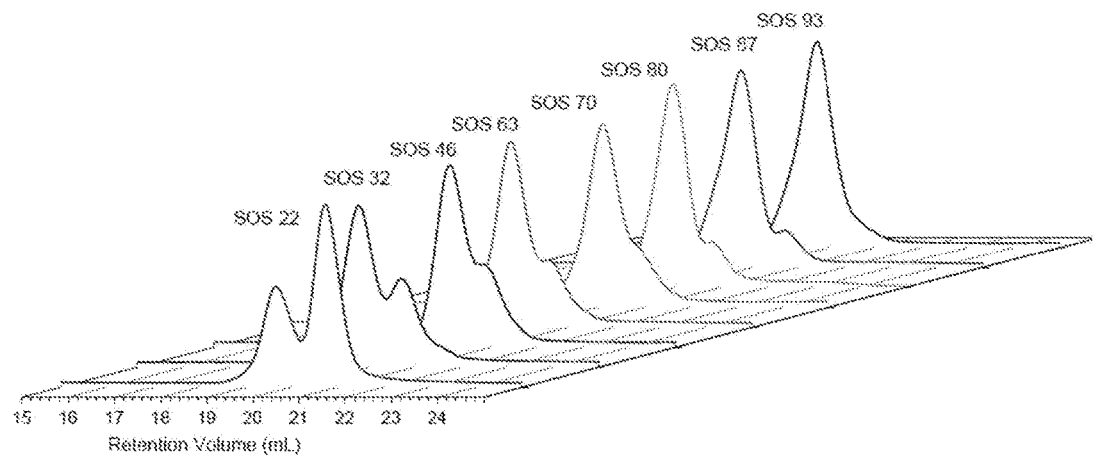
FIG. 3. Size Exclusion Chromatography (SEC) of dry polymer blends of polystyrene-poly(ethylene oxide) diblock copolymer ("SO") and polystyrene-poly(ethylene oxide)-polystyrene ("SOS") triblock copolymer. SEC confirmed the ability to produce various mol % blends of SOS and SO block copolymers from 22 mol % SOS to 93 mol % SOS. All runs were normalized by total area to compare relative mass % of SOS and SO. The peak positions of the retention volume corresponded to SOS (left) and SO (right).

The fractionated SOS triblock copolymer product of Example 5 was separated using gel permeation chromatography (GPC) was performed with three columns in series with THF as a solvent. The SO and SOS peaks were merged (FIG. 3); therefore, the mol % values were calculated using the multiple peak fit function on Origin 9.1. The integrations for each peak showed the relative mass percent of each component. Using the known molecular weights of the SO diblock and SOS triblock copolymers, from $^1$H-NMR, the mol % were calculated (Equation 1).

$$\text{Mol \% } SOS = \frac{\dfrac{\int Peak_1}{2}}{\dfrac{\int Peak_1}{2} + \int Peak_2} \qquad \text{(Equation 1)}$$

Example 7—Polymer Disk Formation and Characterization (a) Preparation of Dry SOS Triblock/SO Diblock Copolymer Disks Dry polymer for the five different SOS triblock copolymer content blends (22-87 mol %) were placed into a steel circular washer (8 mm×0.83 mm thick) and sandwiched between two sheets of Teflon™. Or uniform disks (8 mm diameter, 0.24-0.28 mm thickness, 0.015-0.016 g) at each SOS composition were prepared via melt pressing at 150° C. for five minutes using a washer between Teflon™ covered Kapton™ sheets on a Carver press. Melt pressing molded the powders into a homogeneous solid and provides the chain mobility needed for self-assembly into the sphere-based morphology. Samples were removed and allowed to cool to room temperature for swelling.

Adding "lattice matched" SOS triblock copolymer produced a primary scattering peak at a nearly identical principal wave vector, although the regularity of the body-centered cubic (BCC) lattice devolved into a liquid-like packing (LLP) of spheres. Retaining the BCC lattice was not needed for hydrogel formation.

(b) SAXS Data

SAXS data were collected on a Rigaku S-Max 3000 High Brilliance 3 Pinhole SAXS system outfitted with a Micro-Max-007HFM Rotating Anode (CuKα), Confocal Max-Flux™ Optic, Gabriel Multiwire Area Detector and a Linkham thermal stage. Polymer disks were mounted on the thermal stage and heated to 120° C., then cooled down to 100° C. and kept in vacuum for 120 minutes before exposure.

SAXS data for systems adopting a LLP of spheres can be fit to a Percus-Yevick hard sphere model adapted for polydisperse systems. From those fits, PS core diameters and aggregation numbers for an average spherical domain can be determined, corresponding to a system that has about 340 chains and a PS core diameter of 21 nm. As such, the scattering data were consistent with PS core diameters of about 19 nm with about 230 block copolymer chains per sphere. These extracted values approximate those in the BBC lattice of the neat S—OH. That is, adding triblock copolymer, while disruptive to the BCC lattice, does not significantly influence the structure of spherical PS aggregates themselves. SEC analysis of samples before and after melt pressing showed no observable sample degradation or change in SOS content.

(c) Swelling Analysis of High SOS Triblock Copolymer Content Hydrogels

Dry polymer disks were all massed prior to swelling and were then allowed to equilibrate in DI water for 24 hours. Once swollen, the gels were removed from the water and gently patted dry with a Kimwipe™ to remove excess water. Water content within gels was determined gravimetrically (g water/g polymer) at three temperatures (10, 22, and 37° C.).

The solutions for swelling were brought to the appropriate temperature using a temperature controlled water bath or oil bath for cooling and heating respectively. Water absorption was calculated by the difference of the mass of the swollen gel and dry polymer disk divided by the mass of the dry polymer.

Figure 4:
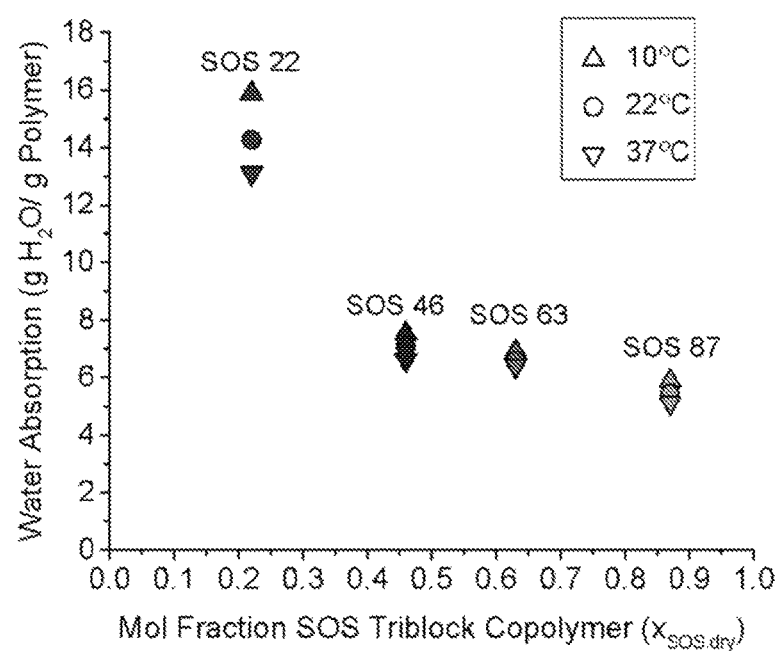
FIG. 4. Water absorption versus mol fraction SOS.

Cooler temperatures (10° C.) resulted in higher swelling ratios, whereas warmer temperatures (37° C.) resulted in a lower swelling ratio. As triblock copolymer content increased, the swelling ratio decreased, with little effect after 46 mol % as seen in FIG. 4.

Two competing forces determined the swelling dimensions of the hydrogel: the osmotic driving force of the water, and the entropic restoring force of the tethering PEO midblock. As temperature increased, the osmotic driving force diminished, resulting in lower water absorption. Higher temperatures also reduced the solubility of the PEO matrix in water. Triblock copolymer content affected swelling by increasing tethers between spheres, resulting in the hydrogel's restricted ability to imbibe water. Overall, the hydrogels swelled isotropically.

Figure 41:
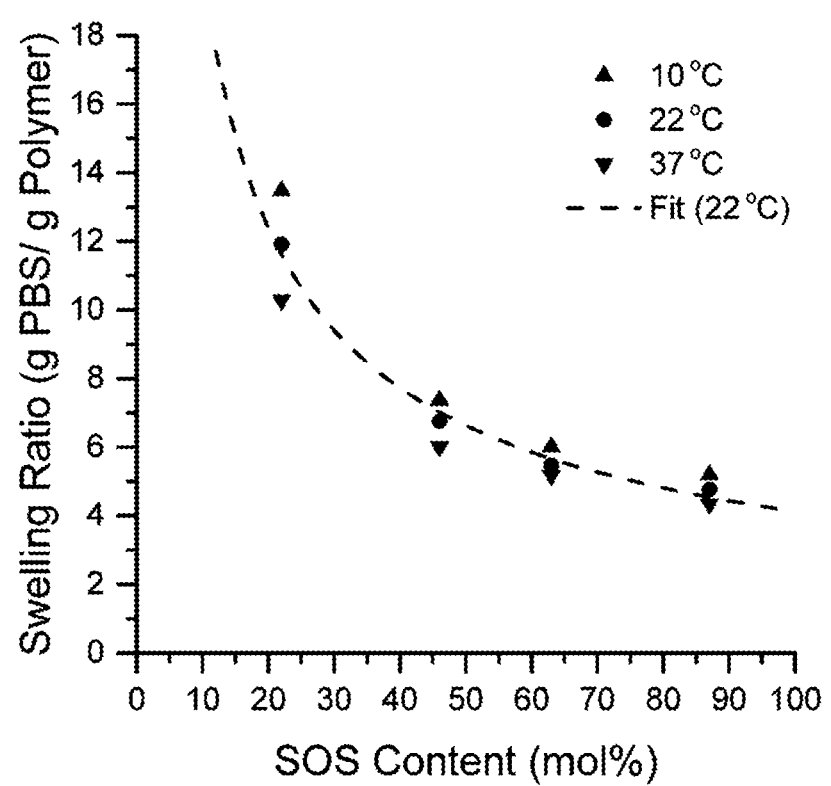
FIG. 41. Gravimetrically determined swelling ratio data in phosphate-buffered saline (PBS) for SOS22, SOS46, SOS63, and SOS87 at 10° C., 22° C., and 37° C. with an approximate power fit (95.6(SOS mol %)$^{-0.682}$, $R^2$=0.99).

The swelling measurements were repeated for hydrogels prepared in phosphate-buffered saline (PBS). FIG. 41 shows gravimetrically determined swelling ratio data in PBS for SOS22, SOS46, SOS63, and SOS87 at 10° C., 22° C., and 37° C. with an approximate power fit (95.6(SOS mol %)$^{-0.682}$, $R^2$=0.99). As SOS content increased, the swelling ratio decreased accordingly. This effect may be partially due to an increase in the number of connections between spherical domains as SOS content increased. The higher SOS content increased the number of trapped topological entanglements produced in the melt, resulting in a restricted ability of the hydrogel to imbibe PBS. The lower swelling ratio at higher temperatures may be due to the reduced solubility of the PEO matrix as temperature increased.

Example 8—Indentation Relaxation Testing of Swollen Hydrogels

Specimens were prepared according to Example 7 and were kept hydrated in DI water before and during indentation relaxation tests, which were run on a servo hydraulic test system (Bionic Model 370.02 MTS Corp, Eden Prairie, Minn.). The water bath containing the sample was attached to a multi-degree of freedom camera mount, and an x-y plate fixture allowing for the indentation surface to be oriented normal to the indenter and centered on the specimen, respectively. A spherical tip with a diameter of 1.59 mm was an indenter, and loads were recorded using a 908 g load cell (Futek™ LSB200, Irvine, Calif.). Because compressive properties are time dependent, both equilibrium and instantaneous moduli were computed.

All samples were preloaded to 2 g, and preliminary tests determined a relaxation time of 300 seconds resulted in equilibrium conditions. Specimens were indented to a strain of 12%/sec. Hertzian contact (Equation 2) was applied and used to determine both the instantaneous and equilibrium moduli. The contact equation assumed contact between an elastic half space and a sphere where F is the force, R is the radius of the indenter, d is the indentation depth, $E_1$ and $\upsilon_1$ are the elastic modulus and Poisson's ratio of the hydrogel respectively, and likewise $E_2$ and $\upsilon_2$ are the elastic modulus and Poisson's ratio of the indenter. The indenter tip had an elastic modulus and a Poisson's ratio of 210 GPa and 0.3, respectively. The elastic modulus of the hydrogel was calculated from unconfined compression testing while the Poisson's ratio of the hydrogel was approximated to be 0.5 in this small strain regime.

$$E_1 = \frac{(1-\upsilon_1)^2}{\left(\frac{3F}{4R^{\frac{1}{2}}d^{\frac{3}{2}}}\right) - \left(\frac{(1-\upsilon_2)^2}{E_2}\right)} \quad \text{(Equation 2)}$$

Figure 5:
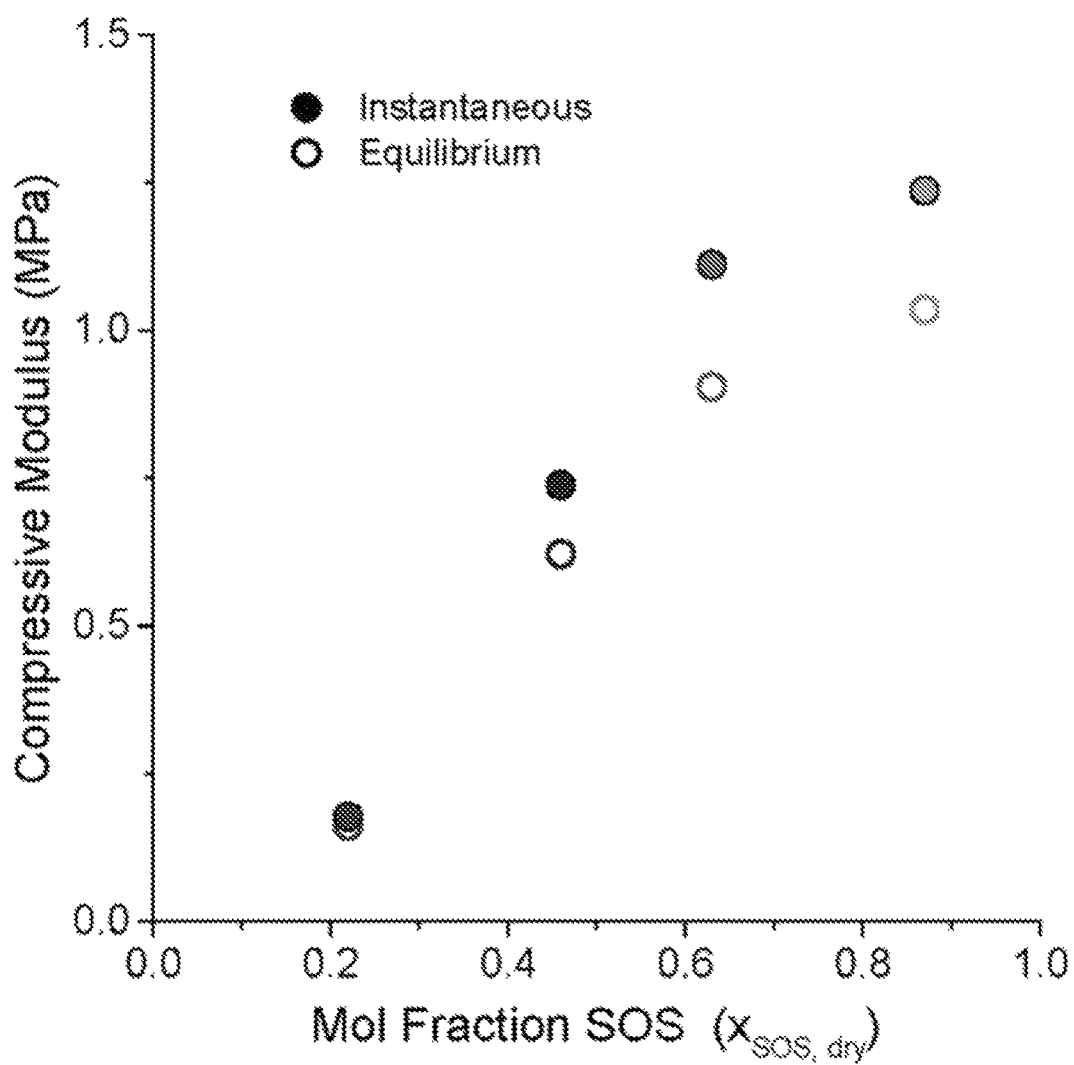
FIG. 5. Indentation relaxation testing of hydrogels swollen in deionized (DI) water showing the dependence of both instantaneous and equilibrium compressive modulus on SOS content of four distinct SOS blends. (Filled circles: instantaneous compressive modulus, unfilled circles: equilibrium compressive modulus).

Indentation testing was performed on four hydrogel blends to develop a complete picture of osmotic movement during compression and its effect on mechanical properties, as seen at FIG. 5. In indentation testing of hydrated materials, this was an effect of instantaneous modulus—attributed to trapped water generating a reactionary force—followed by an equilibrium modulus after the material "relaxes," or water has sufficient time to move from the indentation site.

The equilibrium moduli were 14.9±5.3% lower than the instantaneous moduli, implying a significant effect of water movement on modulus. Testing showed increasing SOS content increased both the instantaneous and equilibrium modulus in indentation. This increase in compressive modulus in higher triblock systems was largely due to more coronal overlap of the micelles. As the triblock copolymer content increased, the physical crosslinks between micelles increased, which increased topological entanglements, limited micellar separation, increased coronal overlap, and stiffened the material. The increased topological entanglements in higher SOS content hydrogels yielded a greater relaxation in modulus due to an increased restriction to fluid flow producing a higher relative instantaneous force, as seen at FIG. 6.

Figure 42:
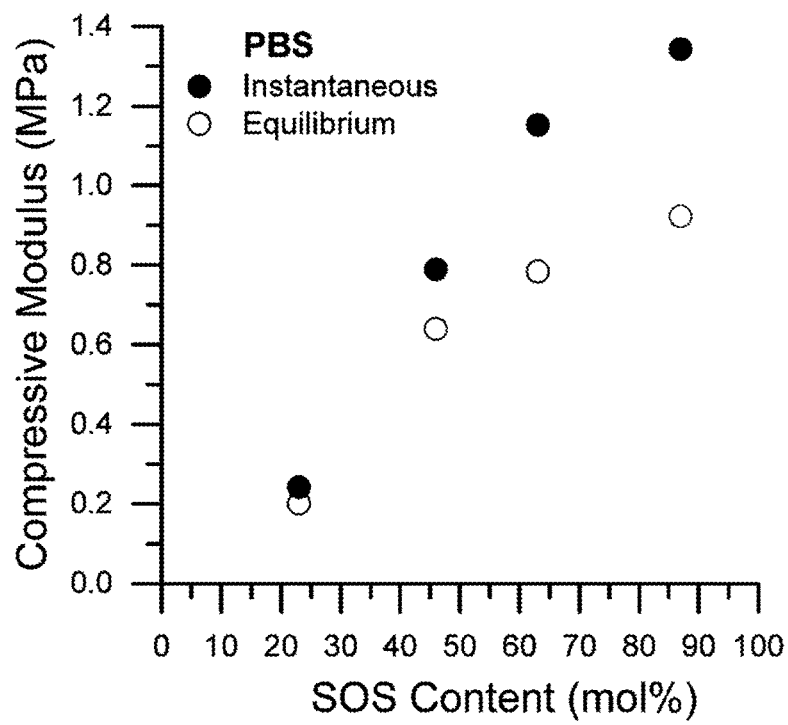
FIG. 42. Indentation relaxation data for SOS22, SOS46, SOS63, and SOS87 in phosphate-buffered saline (PBS) at room temperature.

Indentation measurements were also taken for hydrogels prepared in phosphate-buffered saline (PBS). FIG. 42 shows indentation relaxation data for SOS22, SOS46, SOS63, and SOS87 in PBS at room temperature. All samples were strained to 12% in 1 second and allowed to relax for 300 seconds. Hertzian contact was applied to determine the instantaneous and equilibrium moduli. As SOS content increased, the instantaneous and equilibrium moduli increased, largely due to increased coronal overlap between adjacent micelles. As the SOS content increased, the chain density also increased, leading to a higher resistance to mechanically-induced flow. Thus, the initial modulus temporarily increased under a constant load but eventually relaxed once mechanically induced flow was initiated.

Example 9—Tensile Testing of Swollen Hydrogels

Tensile testing was performed on specimens from Example 7 on an ARES-rheometer (TA instruments, DE) at room temperature. Gels were swollen as disks and cut into strips for tensile testing. The strips were 3 mm wide, 8 mm long, and 0.8 mm thick. The strips were placed into torsion rectangular grips (TA Instruments, DE) with a layer of sandpaper between the grip and the gel to reduce slippage. The gels were clamped and pulled at a force of 5 g to ensure the gel was taut. The gel was then extended to a midsubstance failure at a strain rate of 2%/sec. Once the mean strain at break ($\lambda_f$) was determined, new samples of the same size were strained in intervals of 20% to $\lambda_f$. Samples were strained then returned to unstrained conditions (i.e. 0-20-0-40-0-60 . . . % $\lambda_f$, etc.) at a strain rate of 2%/sec.

Figure 7:
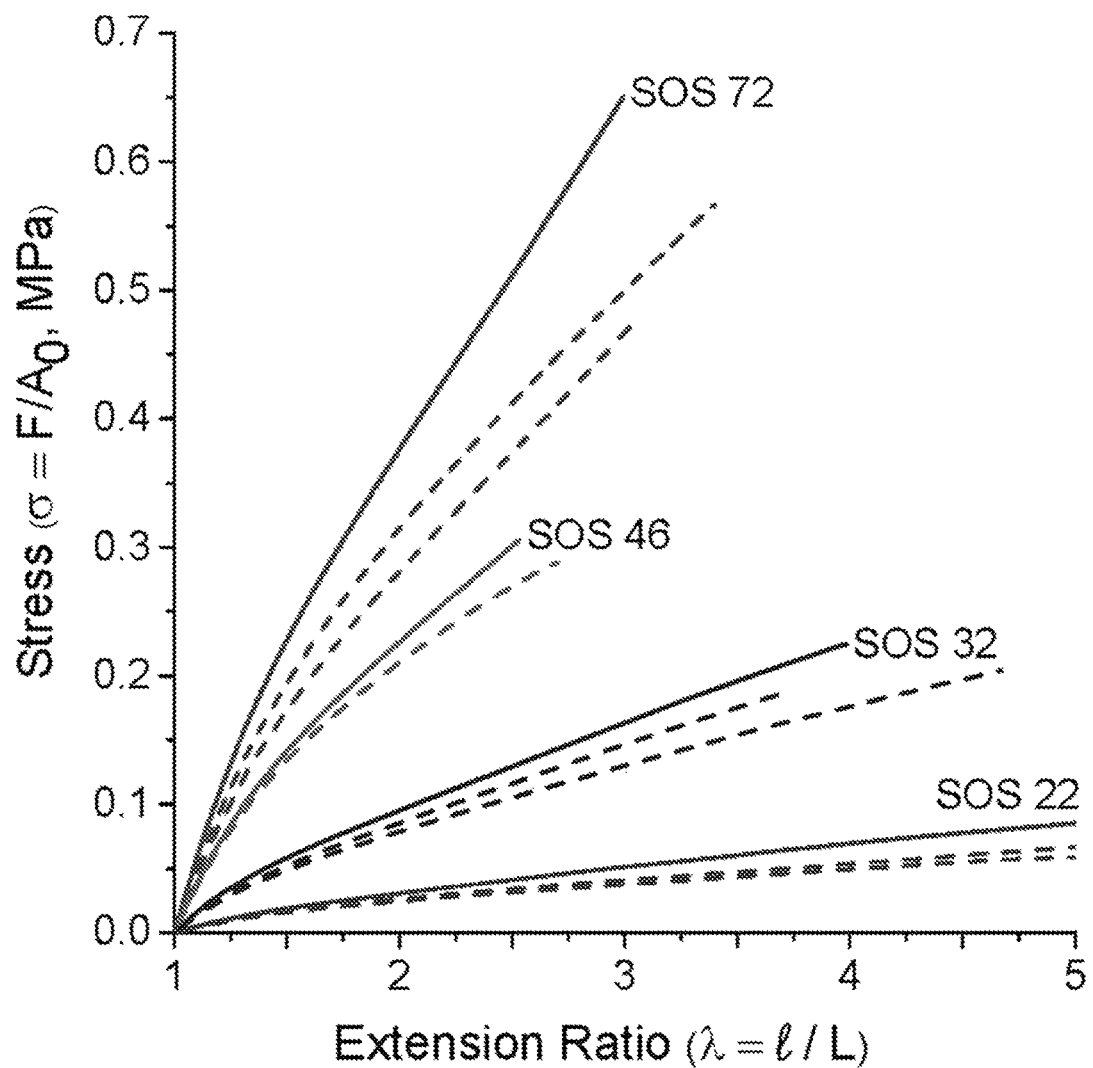
FIG. 7. Ultimate tensile testing showing the relationship of tensile stress (kPa) and Extension ratio of various SOS blends. All samples were pulled to failure at a strain rate of 2%/sec. (Solid line indicates highest modulus run for clarity of the effect of SOS on modulus).

As the SOS content increased, the hydrogels demonstrated a higher tensile modulus and a lower strain at break (FIG. 7). The fixed junction points increased, shifting from dynamic entanglements to greater topological entanglements and increased coronal overlap. The extension ratio no longer decreases after 46 mol % SOS as SOS content increases, but the modulus continues to increase with increased triblock. The very slight increase in extension ratio between 46 and 72 mol % suggested that the distance between styrene spheres have reached a set distance between one another while topological entanglements increase. Further proof of this shift from dynamic to topological entanglements is supported by the swelling ratios being very similar in hydrogels higher than 46 mol %.

Figure 8:
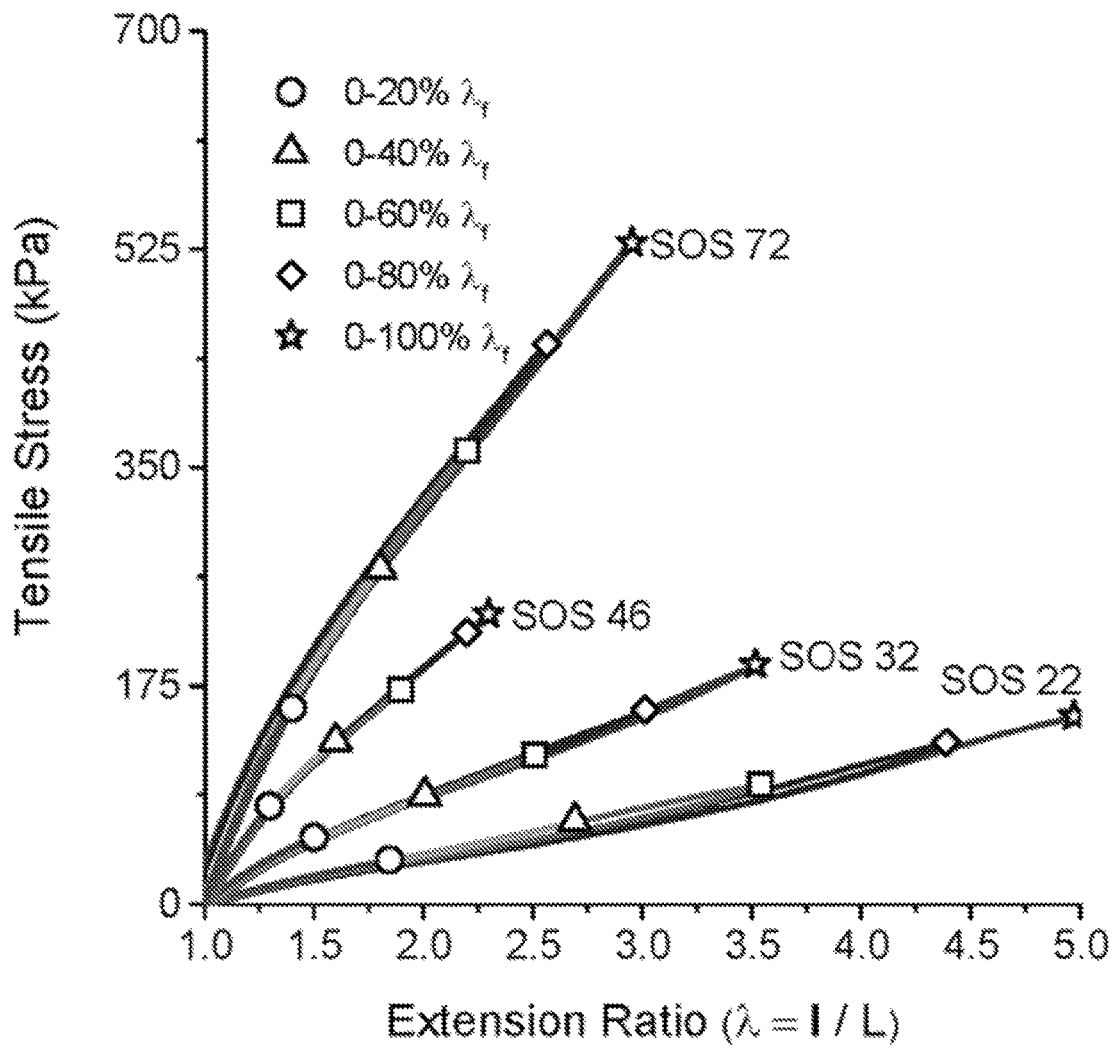
FIG. 8. Loading in interval of mean extension at break in tension showing the relationship of tensile stress (kPa) and extension ratio and hysteresis of swollen hydrogels of different SOS mol %. All samples were pulled in intervals of 20% of the mean extension at failure ($\lambda_f$) at a strain rate of 2%/sec to the full mean extension at failure (i.e. 0-20-0-40-0-60- . . . % of mean extension at failure).

The stress-strain profile of these same samples loaded in successive intervals of 20% up to the mean break at failure (4) revealed virtually no observable hysteresis or fatigue from one loading interval to the next (FIG. 8). This result suggested recoverable modulus and fatigue resistance, unlike the permanent fractures to the primary network in DN hydrogels and the permanent hysteresis in DN hydrogels seen even at low strain rates.

Without wishing to be bound by theory, the hydrogels disclosed herein performed as they do because of how they absorb energy. The topological and dynamic entanglements—as opposed to the highly concentrated fixed entanglements in DN primary networks—allowed for recoverable energy absorption through repeated SO free chain ends and sliding topological entanglements of SOS chains. This testing revealed a high degree of tunability and elasticity. Generally, failure under tensile loading strongly correlated to fracture initiated at local defects, just like in many elastic polymers, including biological tissues.

Example 10—Shear Testing of Swollen Hydrogels

Hydrogels were prepared according to Example 7 and were shear tested on an ARES-rheometer (TA Instruments, DE) using an 8-mm diameter compression tip at room temperature (~22° C.). Swollen hydrogels were removed from water and excess water was blotted away. Hydrogels were centered on a 50-mm stainless steel flat plate and compressed until 2 g of normal force was measured on the instrument to ensure contact of the force transducer with the gels. Dynamic frequency sweeps (oscillatory shear) were performed for each sample using 0.5% shear strain over a frequency range of 0.1-10 radians/sec. Slip was minimized by placing each sample under a fixed 10% compressive strain throughout the experiment.

Figure 9:
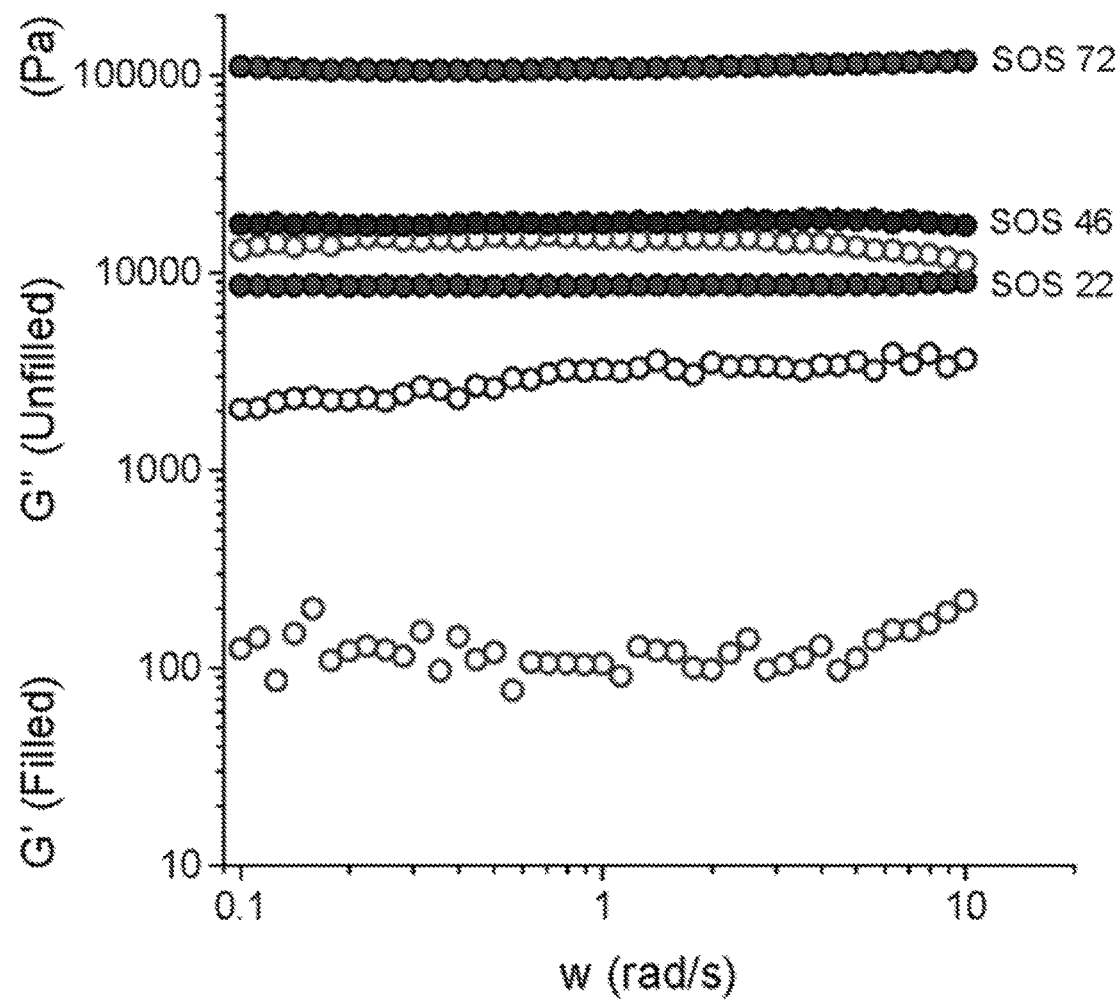
FIG. 9. Frequency sweep of 22, 46, and 72 mol % SOS hydrogels under oscillatory shear at 0.7% strain. All samples were measured at a strain rate in the linear viscoelastic regime that produced behavior typical of an elastic solid.

The dynamic mechanical response of each hydrogel blend at 20° C. under oscillatory shear is given in FIG. 9. The data portray both the elastic (G') and loss (G") moduli of each hydrogel as a function of angular frequency under 0.4-0.5% strain. The observed plateau behaviors in G' and G", combined with consistent ratios of G'/G" of 20-100 for the entire frequency range, are characteristics typical of elastic materials.

The mechanical properties were a function of the SOS content of the hydrogels as demonstrated in the indentation (Example 8) and tension (Example 9) studies. The near order of magnitude difference between the storage and loss modulus demonstrates the high elasticity of these materials even with their high water content.

Example 11—Unconfined Compression Testing

Hydrogels prepared according to Example 7 were also subjected to unconfined compression testing on an ARES-rheometer (TA Instruments, DE) using an 8-mm diameter compression tip (TA Instruments, DE) at room temperature (~22° C.). Swollen hydrogels were removed from water and excess water was blotted away. Hydrogels were centered on a 50-mm stainless steel flat plate and compressed until 2 g of normal force was measured on the instrument to ensure contact of the transducer with the gels. The hydrogels were then compressed to 40% strain at a strain rate of 2%/s while the force transducer measured the normal force response. This was performed for two cycles on each gel to check for mechanical hysteresis.

For compressive cyclical testing, previously swollen samples were cut into 8-mm cylindrical disks with a biopsy punch and tested in DI water at room temperature to maintain hydration. Samples were mounted to a polished aluminum flat plate and compressed with a secondary aluminum plate attached to a 908 g load cell (Futek LSB200, Irvine, Calif.). A preload of 20 g was applied to the sample to ensure contact and the samples were compressed for 1,000 cycles using a servo hydraulic testing system (Bionic Model 370.02 MTS Corp, Eden Prairie, Minn.). Samples were compressed 12%/sec at a frequency of 1 Hz. Following the first 1,000 cycles the sample was unloaded and allowed to rest for 1 hour before being retested under the same conditions for four additional sets of 1,000 cycles.

MATLAB (Mathworks, Natick, Mass.) was used to analyze the resulting data. Peak compressive force and displacement for each cycle were used to ascertain the compressive modulus. Initial modulus was determined from the first cycle, while the modulus at 500 cycles and 1,000 cycles averaged from the ten cycles nearest those numbers. The initial and final modulus values and the percent decay were assessed over the first 500 and final 500 cycles.

Figure 10A:
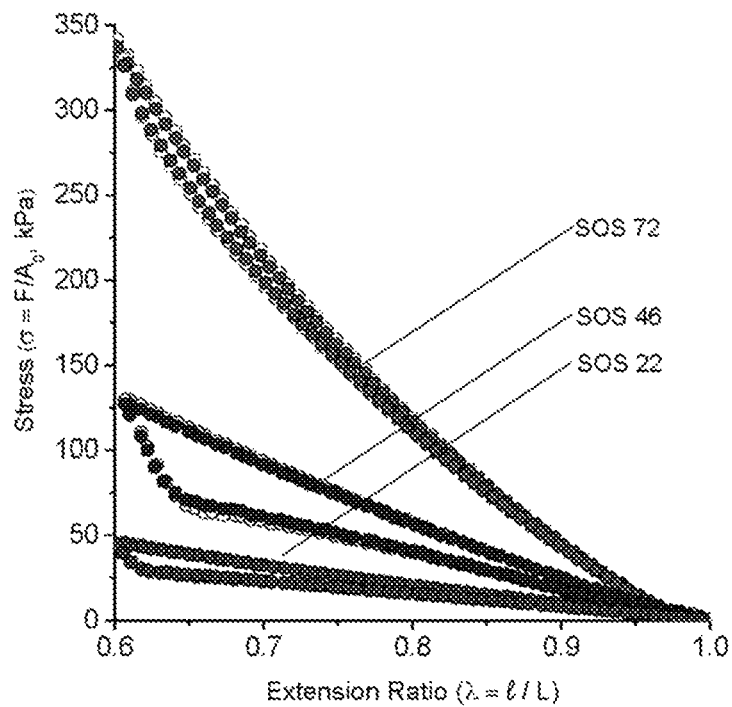
FIG. 10A All samples were compressed for 2 cycles to 40% strain at a strain rate of 2%/sec (filled circle: cycle 1, unfilled circle: cycle 2).

Two-cycle compression testing showed very little damage to the underlying polymer network of the gel, as each run traced the last. Each hydrogel recovered with little hysteresis (FIG. 10). Without wishing to be bound by theory, the varying hysteresis may be rooted in the degree to which the entanglements slowed recovery, which directly related to osmotic forces which redistributed water molecules throughout the sample.

Figure 10B:
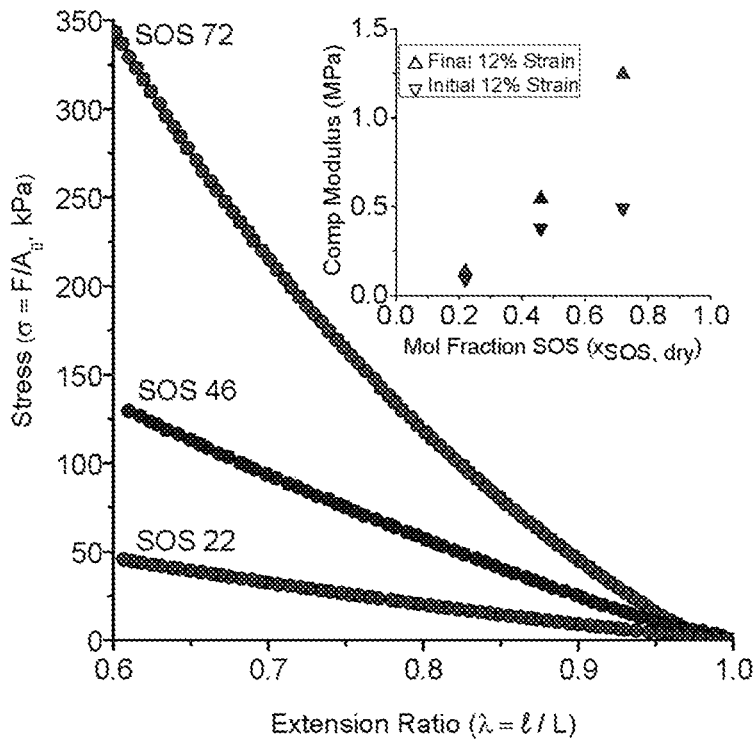
FIG. 10B Stress (kPa) vs. extension ratio of the initial compression of each of the three blends to 40% strain. (Upper right) Compressive modulus versus molar fraction SOS for the initial 12% strain and the final 12% strain (0-12% and 28-40%).

FIG. 10 showed the same dependence of SOS content increasing the modulus of the samples in compression. The trend carried not only at low strains of 12% as seen in indentation (Example 8), but also at higher strains of 40%. In the subset of FIG. 10B, the SOS content displayed an exponential relationship with the compressive modulus in these higher strains compared to decaying role in the lower strains. At higher strains, more topological entanglements and physical crosslinks from higher SOS content are engaged, producing a greater effective modulus.

Figure 11A:
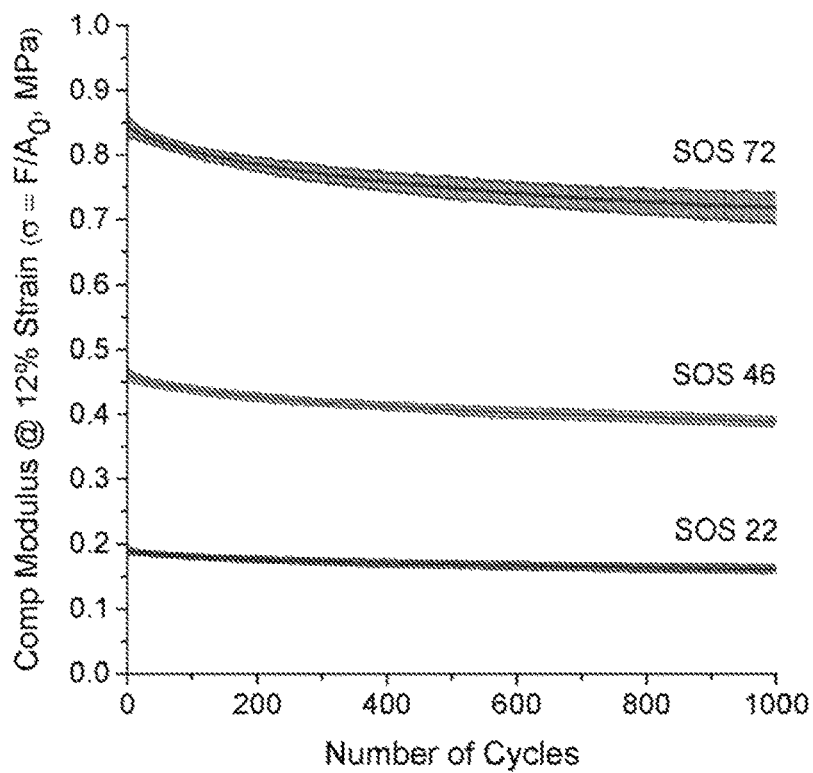
FIG. 11A Compressive fatigue testing of swollen hydrogels showing the recoverable loss in modulus for 5000 cycles on 22, 46, and 72 mol % SOS and the increasing modulus with increasing SOS content. All samples were compressed at a 12%/sec strain rate and a frequency of 1 Hz for 1000 cycles while fully submerged in a phosphate-buffered saline (PBS) bath, allowed to rest unloaded for 1 hour, and reloaded for four additional 1000 cycle runs.
Figure 11B:
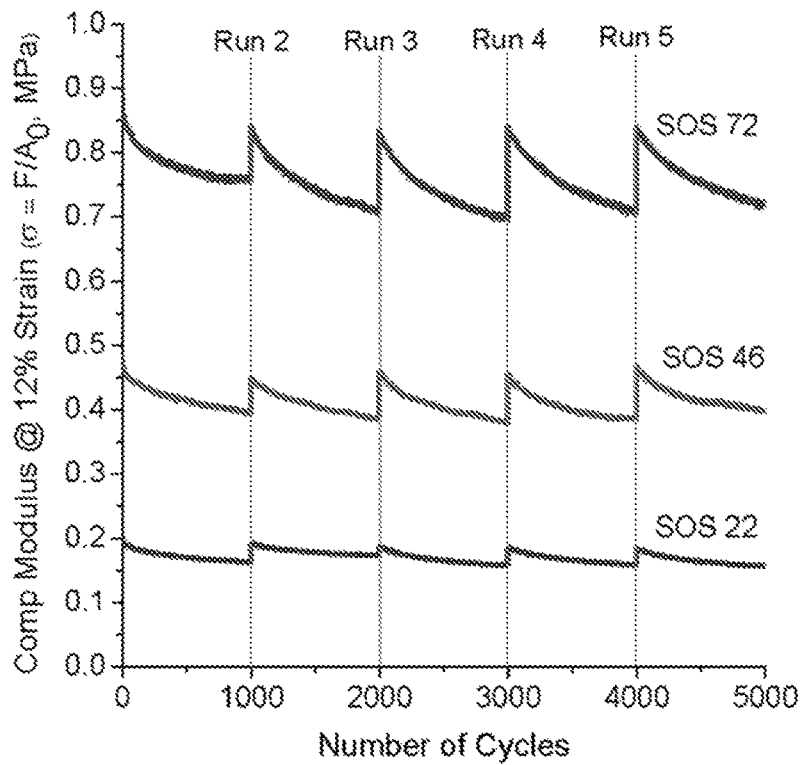
FIG. 11B The average of these 5 runs with standard deviation.

To better understand the materials' fatigue resistance, the three SOS content hydrogels were strained to 12% at a strain rate of 12%/sec for 5 consecutive 1000 cycle runs (FIGS. 11A & 11B). The average steady relaxation was 14.7±0.5% in the modulus throughout each 1000 cycles. Nonetheless, the original modulus of the prior run was recovered (98±4.5%), following one hour of no loading for the SOS-containing hydrogels. This result implied very little to no damage to the underlying polymer network upon these loading cycles. As evinced through video analysis, the shape fully recovers. This recoverable decay was likely from water moving within the hydrogel.

Table 2 shows the average modulus results and decay results across the 5 runs. The decay across the various SOS content was nearly identical for the full 1,000 cycles as well as the final 500 cycles, suggesting a similar mechanism. Traditionally, in high cycle fatigue testing, damage from cycle to cycle is due to stress concentrations leading to microcrack formations and mechanical failure of the material. Due to the minimal amount of fixed juncture points in the hydrogel system, there was a large amount of chain mobility. Recoverable energy absorption allowed the system to minimize stress concentrations and microcrack formations and to increase the mechanical longevity of the material. After each run, the hydrogel regained its original configuration, producing a narrowly-distributed pooled mean modulus over the first ten cycles (0.614±0.012 MPa).

TABLE 2

Average initial modulus (MPa), Average modulus over full 100 cycle run (MPa), Average decay in modulus throughout full run (%), and average decay over the second half of the 1000 cycle run (%) for three SOS content hydrogels (22, 46, and 72).

| Sample | Initial Modulus (MPa) | Mean Run Modulus (Mpa) | Full Run Decay (%) | Second Half Run Decay (%) |
|---|---|---|---|---|
| Average SOS 22 | 0.19 ± 0.008 | 0.17 ± 0.009 | 14.4 ± 4.3 | 4.2 ± 1.2 |
| Average SOS 46 | 0.46 ± 0.01 | 0.41 ± 0.007 | 15.2 ± 1.9 | 4.4 ± 1.1 |
| Average SOS 72 | 0.85 ± 0.015 | 0.76 ± 0.024 | 14.6 ± 2.0 | 4.2 ± 2.0 |

Figure 12:
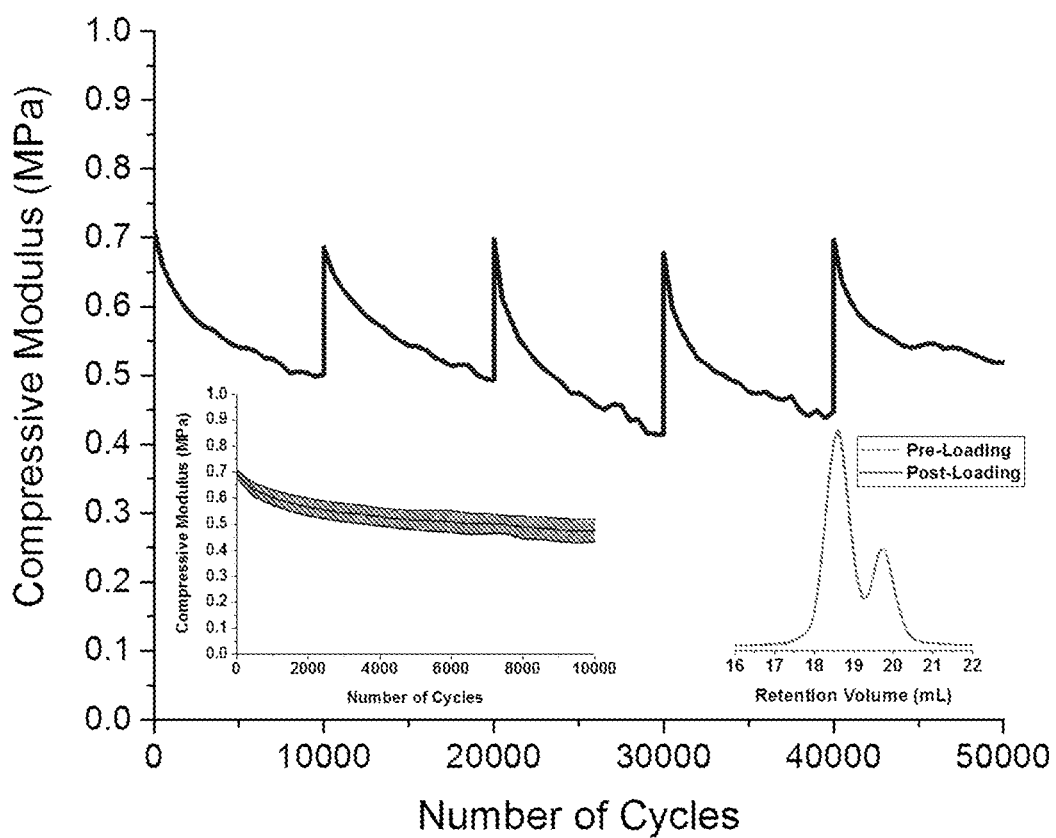
FIG. 12. Example of an SO/SOS hydrogel composed of 61 mol % SOS subjected to five successive runs of 10,000 cycles each, in which 12% compression was applied at a frequency of 1 Hz.

FIG. 12 exemplifies an SO/SOS hydrogel composed of 61 mol % SOS subjected to five successive runs of 10,000 cycles each, in which 12% compression was applied at a frequency of 1 Hz. The hydrogel was allowed to rest under no applied strain for the balance of 24 hours before the next run. The modulus represented the mean value over the entire 12% compression, calculated as maximum stress over strain. The left inset shows the average mean modulus for all five 10,000-cycle runs. The right inset shows the SEC data for the two-component blend before and after the full 50,000-cycle experiment.

Figure 13:
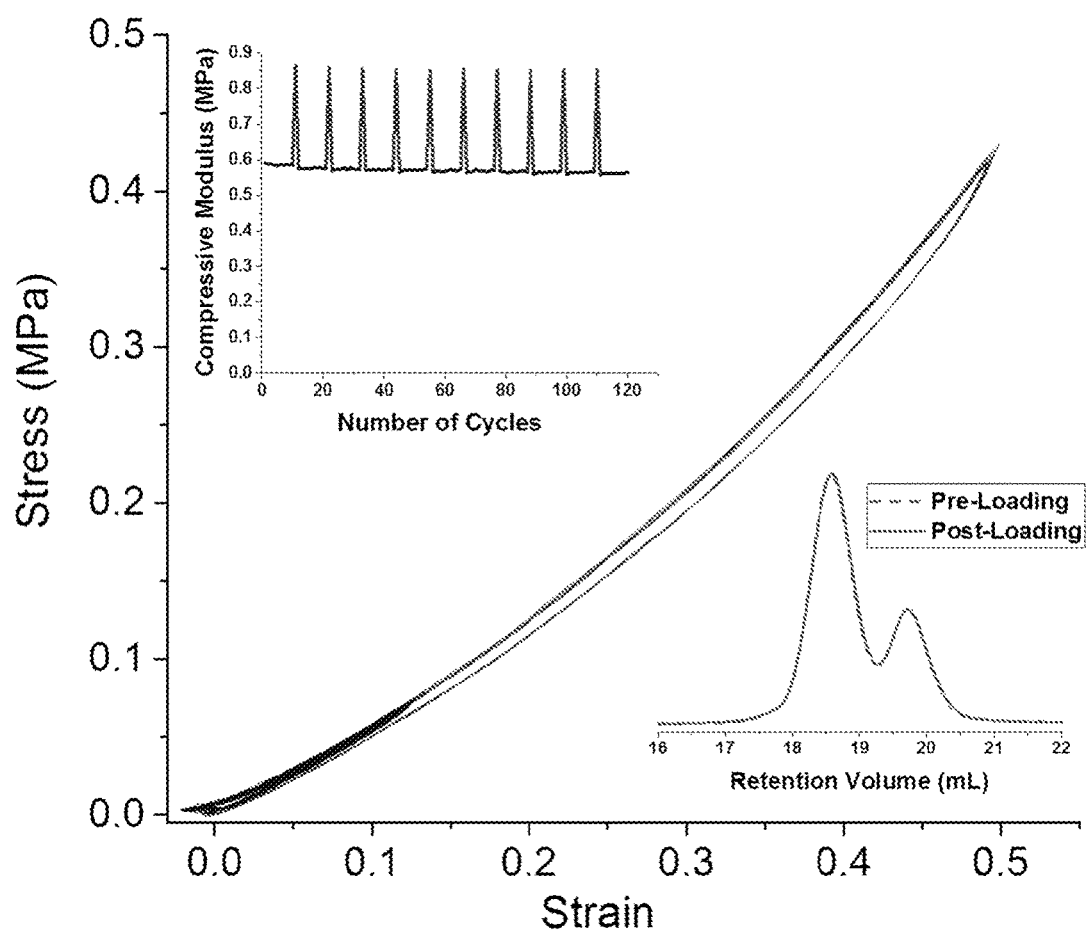
FIG. 13. Example of an SO/SOS hydrogel composed of 61 mol % SOS subjected to a compression overloading experiment, in which 12% compression was applied at a frequency of 1 Hz, with 50% compression applied every 11$^{th}$ cycle.

FIG. 13 exemplifies an SO/SOS hydrogel composed of 61 mol % SOS subjected to a compression overloading experiment, in which 12% compression was applied at a frequency of 1 Hz, with 50% compression applied every 11$^{th}$ cycle. The stress strain behavior for all 120 cycles is shown. The upper inset shows the mean modulus calculated over the entire 12 or 50% compression, calculated as maximum stress over strain. The lower inset shows the SEC data for the two-component blend before and after the full 120-cycle experiment. Each cycle showed very little hysteresis between the loading and unloading legs, indicating that minimal energy dissipated. Without wishing to be bound by theory, the reduced hysteresis and relaxation in the modulus may result from deformation in the fluid structure and poroelastic flow.

Figures 14A, 14B:
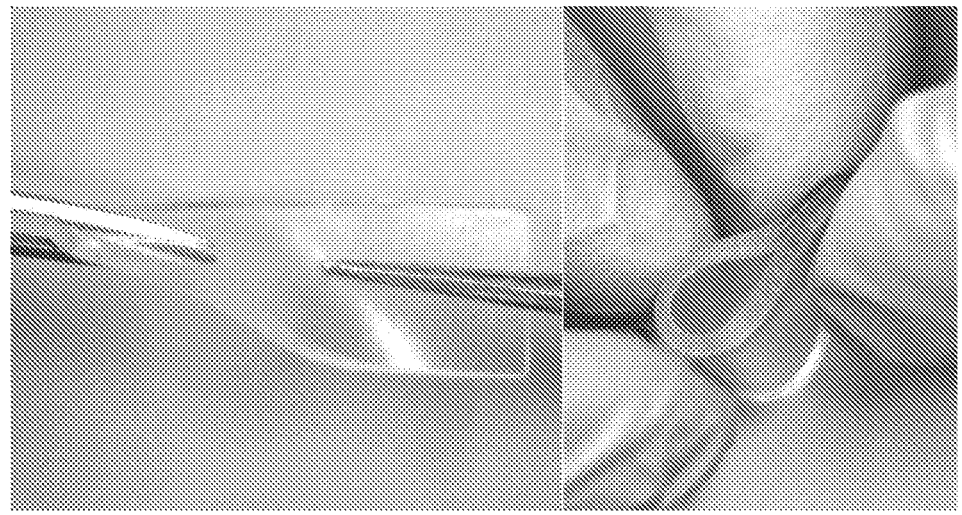
FIGS. 14A and 14B. Examples showing the handling ability of the TPE hydrogels.
Figures 14C, 14D, 14E, 14F:
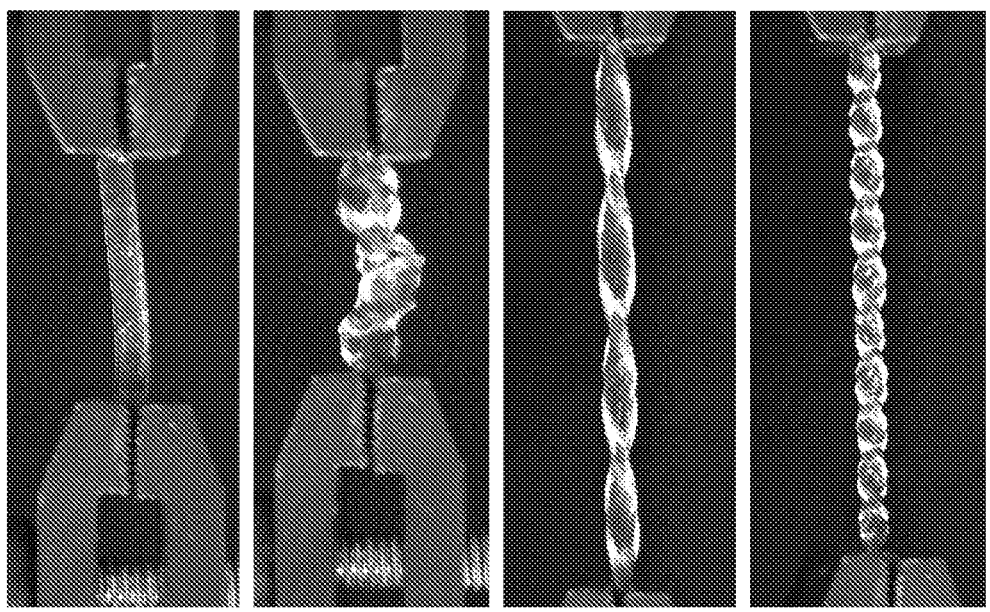
FIG. 14C $\lambda$=1, $\phi$=0.
FIG. 14D $\lambda$=1, $\phi$=4$\pi$.
FIG. 14E $\lambda$=2.5, $\phi$=4$\pi$.
FIG. 14F $\lambda$=2.5, $\phi$=10$\pi$.

FIGS. 14A and 14B show the handling ability of the TPE hydrogels. (C-F) SOS61 held with tweezers. Elastomer-like bending (SOS61). Twisting ability (SOS30) from left to right: (C) $\lambda=1$, $\phi=0$; (D) $\lambda=1$, $\phi=4\pi$; (E) $\lambda=2.5$, $\phi=4\pi$; and (F) $\lambda=2.5$, $\phi=10\pi$.

Figure 15:
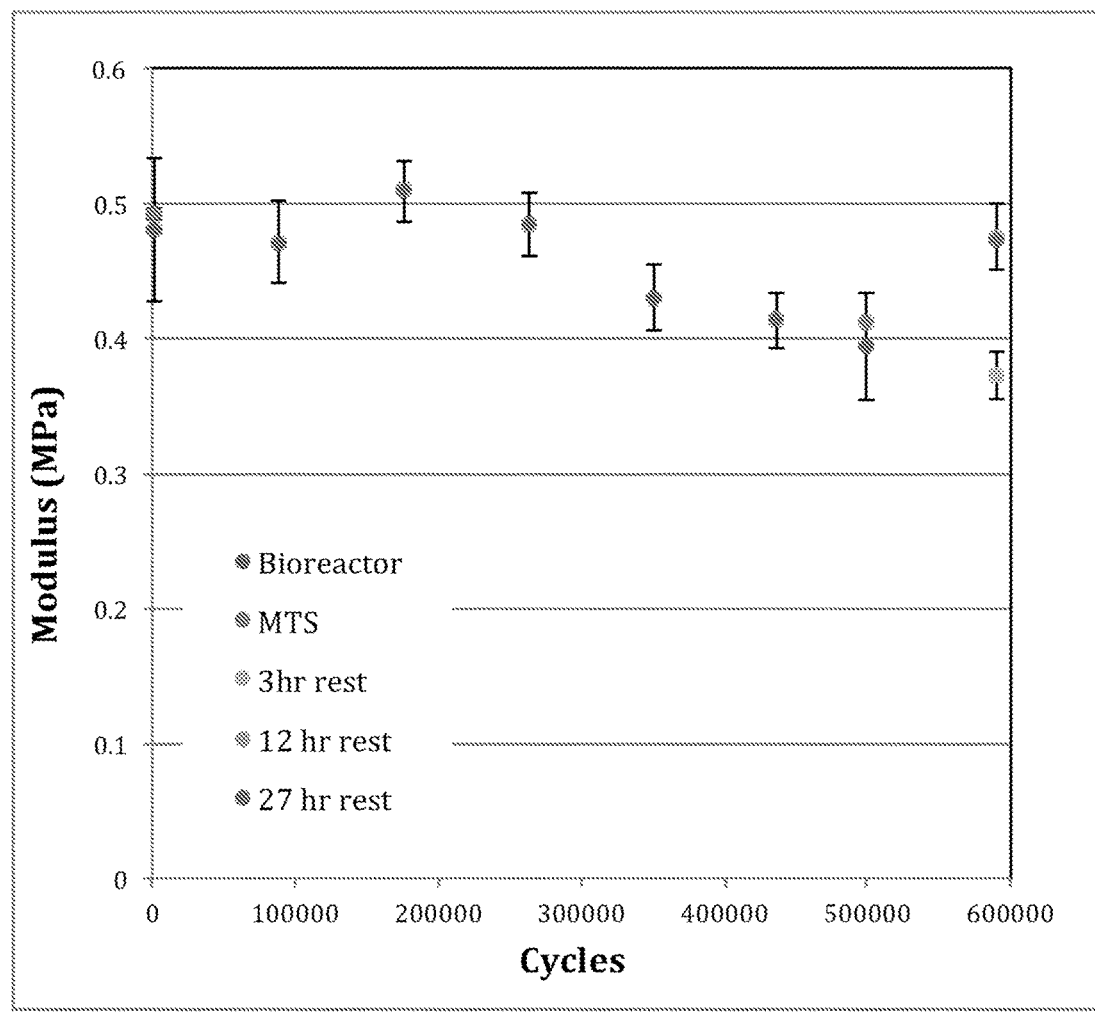
FIG. 15. Example of an SO/SOS hydrogel composed of 61 mol % SOS subjected to 500,000 continuous compression cycles, in which 12% compression was applied at a frequency of 1 Hz.

FIG. 15 exemplifies an SO/SOS hydrogel composed of 61 mol % SOS subjected to 500,000 continuous compression cycles, in which 12% compression was applied at a frequency of 1 Hz. Each data point plotted was derived from the 1000 cycle average of the mean modulus for a given cycle, calculated as maximum stress over strain. The data at 600,000 cycles showed the recovery of the average mean modulus (taken over 1000 cycles) as a function of rest time following the 500,000-cycle test. Comparing moduli as a function of cycle number suggests that the cycled samples may have a faster rate of relaxation once extensively cycled with no observed changes in molecular weight distribution.

Example 12—Synthesis of azido-polystyrene-b-polyethylene(oxide) ("SO-azide").

Various fractions of the parent hydroxyl-functional SO diblock copolymer from Example 5 were substituted with click functionality (SO-azide in this example and SO-alkyne below at Example 13). The SOS triblock copolymer continued to serve as the component forming the primary network in the hydrogel. The azide and alkyne functional SO diblock copolymers provided a latent ability to generate more triblock copolymer at a future time; that is, once the SOS—SO glass had been hydrated and the primary network of triblock copolymer tethers had been established and mechanically engaged as a hydrogel.

SO-azide was prepared via substitution after converting the terminal alcohol groups on the parent SO diblock copolymer to their corresponding sodium or potassium alkoxides. To generate SO-azide, the terminal alkoxide was first converted to a mesyl leaving group before displacement in the presence of sodium azide.

Figure 16:
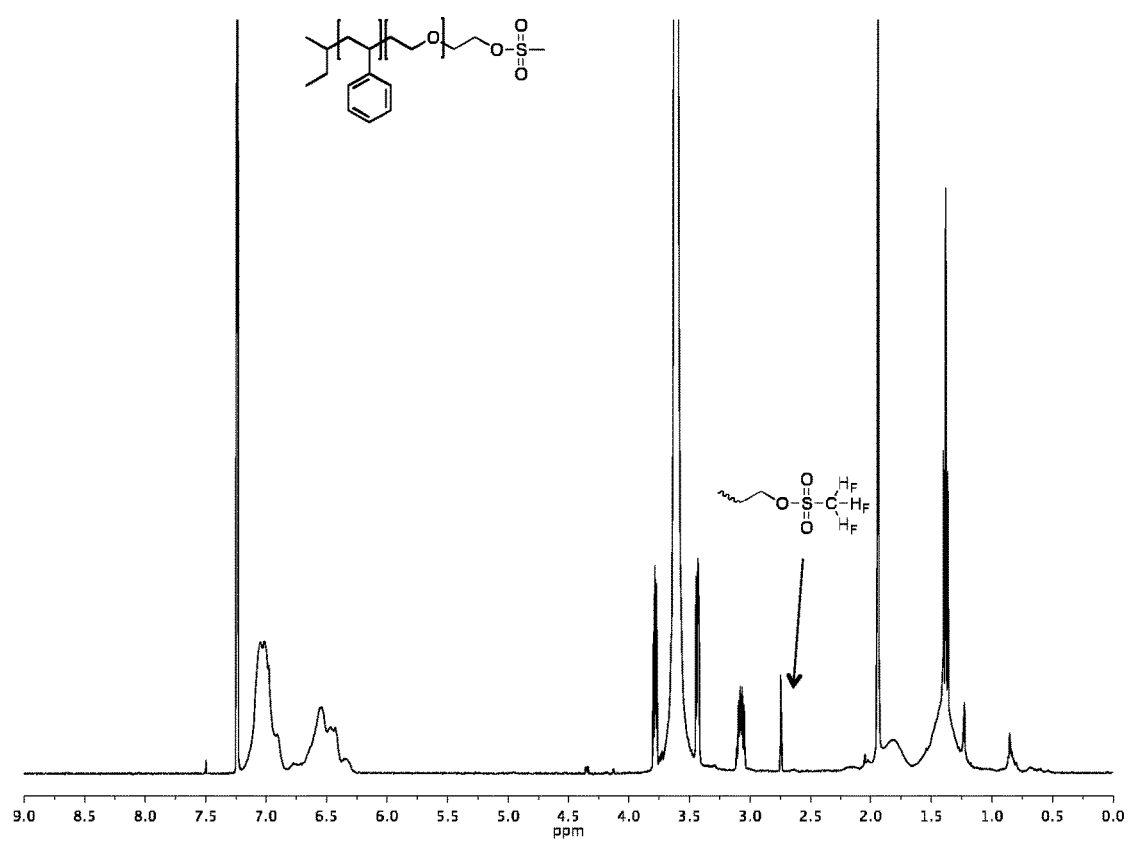
FIG. 16. $^1$H-NMR spectrum of methanesulfonyl-polystyrene-poly(ethylene oxide) ("PS—PEO-Ms," "SO-Ms")). This compound was the precursor of PS—PEO-azide.

To do this, S—OH (5.42 g, 7.8×10$^{-5}$ mol) from Example 1 was added to a 300-mL flask, which was thrice evacuated and backfilled with Ar. Distilled methylene chloride (100 mL) was added to dissolve the polymer. The flask was placed to a 45° C. oil bath at before adding methanesulfonyl chloride (MsCl, 0.12 mL, 20 equiv.) and triethylamine (0.2 mL, 20 equiv.). The reaction stirred overnight and the crude product was filtered then precipitated into pentane (1 L). The solid was collected via vacuum filtration and dried under vacuum overnight to produce a white solid. Yield 5.25 g, 95+%. SEC: (THF, PS stds): M$_{n,SO\text{-}azide}$=70,000 g mol$^{-1}$ (Calculated using M$_{n,S\text{—}OH}$ (SEC) and SO-azide $^1$H NMR. Changes in molecular weights due to end group conversions fall below the accuracy of the calculated values and were therefore neglected), M$_w$/M$_n$=1.05; $^1$H-NMR: $\delta_H$ (400 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$)CH$_2$O—), 4.2-4.4 (t, —CH$_2$—SO$_3$—CH$_3$), 3.1-4.0 (b, —CH$_2$CH$_2$O—, —CH(C$_6$H$_5$) CH$_2$CH$_2$O—), 2.7 (s, —CH$_2$—SO$_3$—CH$_3$), 1.0-2.30 (b, —CH$_2$CH(C$_6$H$_5$)—, CH$_3$CH(CH$_2$CH$_3$)—, —CH(C$_6$H$_5$) CH$_2$CH$_2$O—), 0.5-0.78 (m, CH$_3$CH(CH$_2$CH$_3$)—). See FIG. 16.

Figure 17:
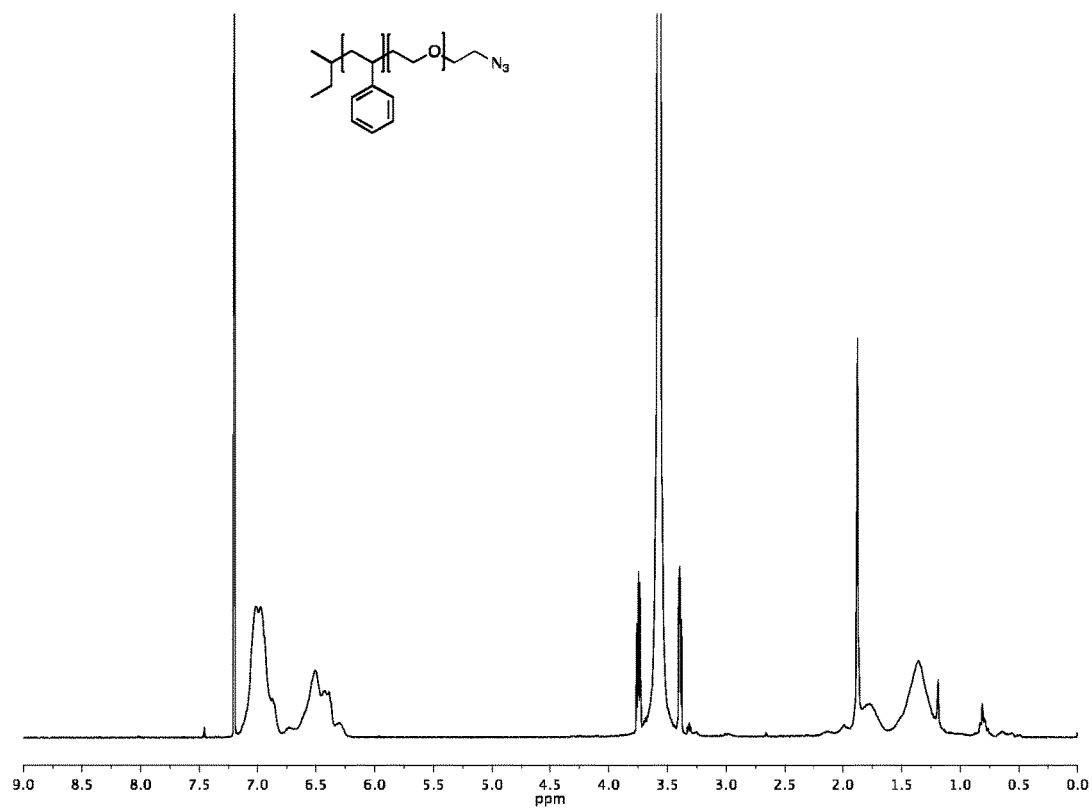
FIG. 17. $^1$H-NMR spectrum of azido-polystyrene-poly(ethylene oxide) ("PS—PEO-azide," "SO-azide"). The terminal methylene protons adjacent to the azide end group overlap with the methylene protons of the PEO backbone (4.0-3.2 ppm). Confirmation of azide group functionality is shown in the FTIR spectrum in FIG. 18.

Methansulfonyl polystyrene-b-polyethylene(oxide) ("SO-Ms," 4.75 g, 6.9×10$^{-5}$ mol) was placed in a 300-mL round bottom flask containing purified DMF under argon in an bath at 60° C. After the polymer was completely dissolved, sodium azide (NaN$_3$, 0.089 g, 20 equiv.) was added to the reaction mixture with vigorous stirring. The crude reaction mixture was filtered after an overnight reaction and then precipitated into ethyl ether. The collected powder was then dissolved in chloroform and washed with DI water. The polymer solution in chloroform was dried over magnesium sulfate and filtered. White powder was collected though filtration under vacuum after the precipitation into pentane. The polymer was then dried under vacuum at room temperature overnight. Yield 4.2 g, 88%. SEC: (THF, PS stds): M$_{n,SO\text{-}Ms}$=70,000 g mol$^{-1}$ (Calculated using M$_{n,S\text{—}OH}$ (SEC) and SO-Ms $^1$H NMR. Changes in molecular weights due to end group conversions fall below the accuracy of the calculated values and were therefore neglected), M$_w$/M$_n$=1.05; $^1$H-NMR: $\delta_H$ (400 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$) CH$_2$O—), 3.1-4.0 (b, —CH$_2$CH$_2$O—, —CH(C$_6$H$_5$) CH$_2$CH$_2$O—), 1.0-2.30 (b, —CH$_2$CH(C$_6$H$_5$)—, CH$_3$CH (CH$_2$CH$_3$)—, —CH(C$_6$H$_5$)CH$_2$CH$_2$O—), 0.5-0.78 (m, CH$_3$CH(CH$_2$CH$_3$)—). See FIG. 17.

Figure 18:
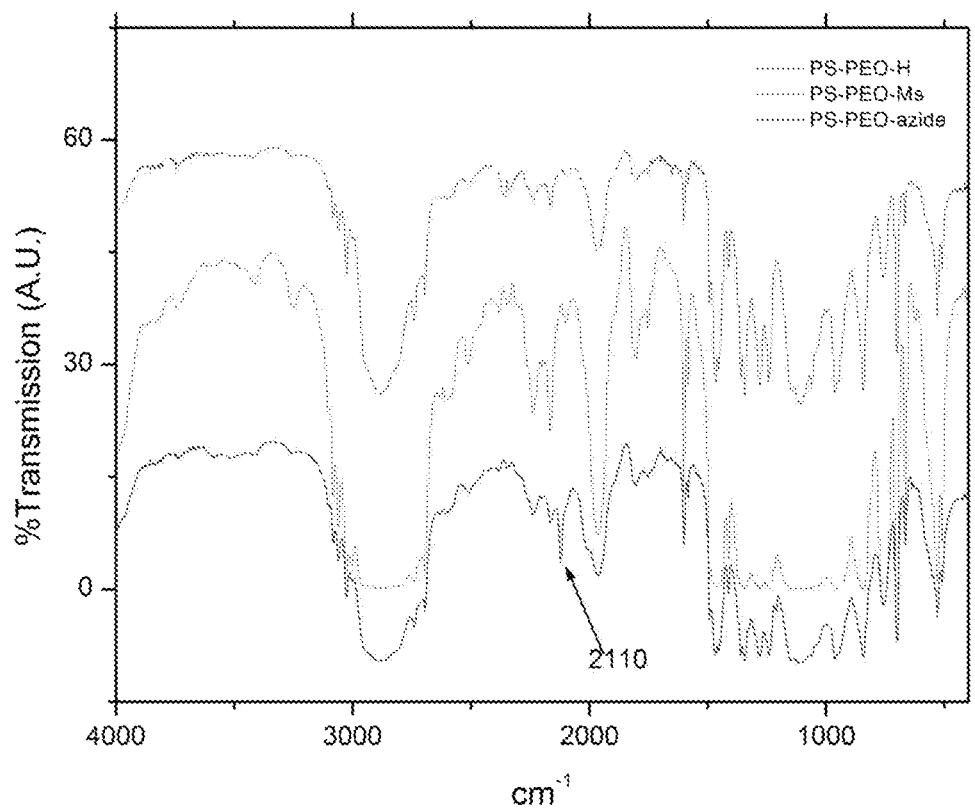
FIG. 18. FTIR spectra of PS—PEO—H ("SO"), PS—PEO-Ms and PS—PEO-azide. The characteristic vibration for the azide group was shown at 2110 cm$^{-1}$.

The methylene protons adjacent to the azide group overlapped with the ethylene oxide backbone and could not be resolved. Complete disappearance of the methyl protons of the mesyl group indicated a successful substitution. FTIR confirmed the presence of an azide vibration (2110 cm$^{-1}$) (FIG. 18). While complete functionalization of the SO-azide could not be confirmed, blends involving SO-azide and SO-alkyne were assembled assuming functionalization of both block copolymers was quantitative.

Example 13—Synthesis of polystyrene-b-polyethylene(oxide)-alkyne ("SO-alkyne")

The polystyrene-b-polyethylene(oxide)-alkyne ("SO-alkyne") was achieved by treating the SO alkoxide with propargyl bromide. S—OH (Example 1, 6.31 g, 9.1×10-5 mol) was placed into a 500-mL two-neck round bottom flask. Dry THF (250 mL) was added to the flask. The solution was heated in a 50° C. oil bath under argon. Once the S—OH was completely dissolved, sodium hydride (0.23 g, 100 equiv.) was added to the solution and stirred for 20 minutes. Propargyl bromide solution in toluene (80 wt %, 0.31 mL, 20 equiv.) was injected to the reaction mixture via an air-free syringe. The temperature was increased to 65° C. to reflux overnight. The reaction mixture was filtered and precipitated three times into pentane (1 L). The suspension was filtered and dried under vacuum overnight to give pale yellow powder.

Figure 19:
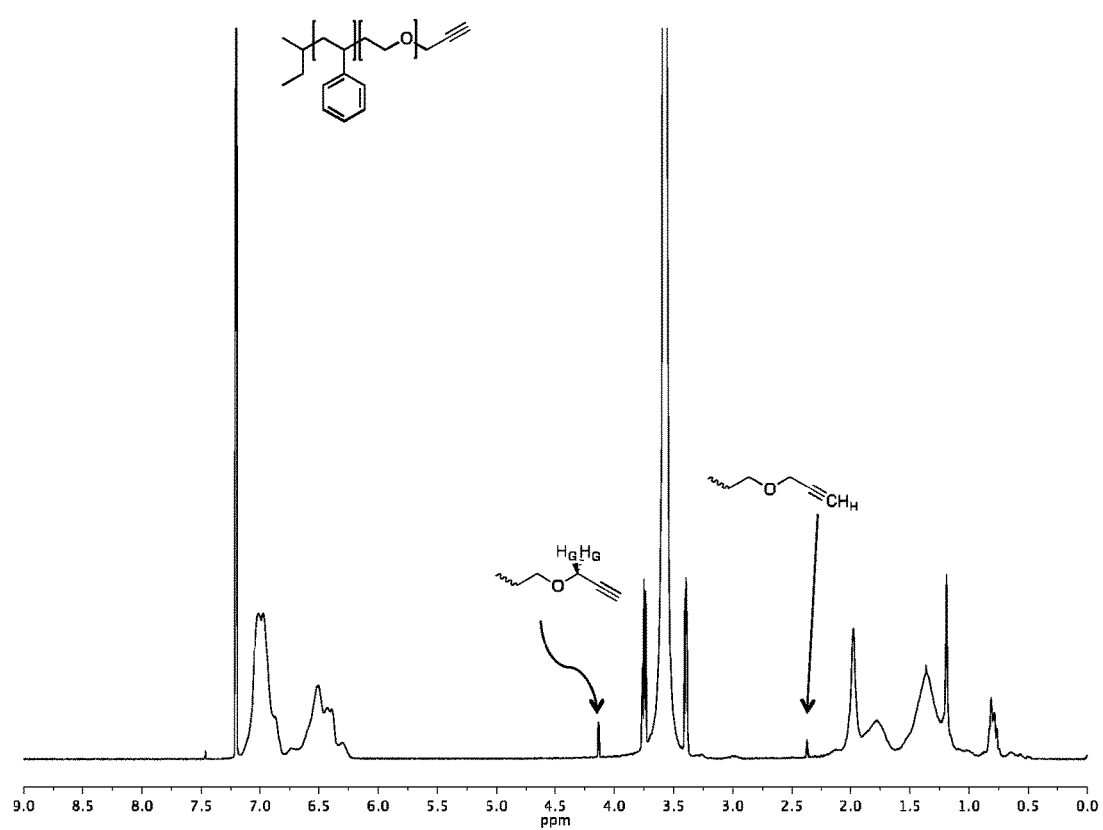
FIG. 19. $^1$H-NMR spectrum of PS—PEO-alkyne.

$^1$H-NMR confirmed transformation of the hydroxyl groups to alkyne groups to be essentially quantitative, given the uncertainty associated with end-group analysis of large polymer molecules by $^1$H-NMR. Yield 5.65 g, 89%. SEC (THF, PS stds): $M_{n,SO-alkyne}$=70,000 g mol$^{-1}$ (Calculated using $M_{n,S-OH}$ (SEC) and SO-alkyne $^1$H-NMR. Changes in molecular weights due to end group conversions fall below the accuracy of the calculated values and were therefore neglected), $M_w/M_n$=1.05; $^1$H-NMR: $\delta_H$ (400 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$)CH$_2$O—), 4.2 (d, —OCH$_2$C≡C), 3.1-4.0 (b, —CH$_2$CH$_2$O—, —CH(C$_6$H$_5$)CH$_2$CH$_2$O—), 2.46 (t, —C≡CH), 1.0-2.30 (b, —CH$_2$CH(C$_6$H$_5$)—, CH$_3$CH(CH$_2$CH$_3$)—, —CH(C$_6$H$_5$)CH$_2$CH$_2$O—), 0.5-0.78 (m, CH$_3$CH(CH$_2$CH$_3$)—). The $^1$H-NMR spectrum of PS—PEO-alkyne is shown at FIG. 19.

Example 14—Preparation of SO/SO-alkyne/SO-azide/SOS Blends

Polymer blends containing between about 8.5 mol % and about 10 mol % SOS and varying, equimolar amounts of SO-azide (Example 12) and SO-alkyne (Example 13) were prepared via solution blending (with freeze-drying) from benzene. The SO-azide: SO-alkyne ratio was held constant at 1:1 and the blend was diluted with reactively inert SO, producing four distinct blends ($A_{pre}$-$D_{pre}$) with varying SO-azide/SO-alkyne content as shown in Table 3.

TABLE 3

Hydrogel composition and post-swelling click chemistry reaction conversion

| Sample | $SOS_{pre}$ (mol %)$^a$ | $SO-X_{pre}$ (mol %)$^a$ | SO-azide:SO-alkyne:S—OH$^a$ | $SOS_{max}$ (mol %)$^b$ | $SOS_{post}$ (mol %)$^a$ | Coupling conversion (%)$^c$ |
|---|---|---|---|---|---|---|
| A1 | 9.3 | 90.7 | 1:1:4 | 28.8 | 20.2 | 60.0 |
| A2 | | | | | 18.4 | 50.8 |
| A3 | | | | | 21.2 | 65.0 |
| A4 | | | | | 20.3 | 60.0 |
| B1 | 9.8 | 90.2 | 1:1:8/5 | 46.5 | 29.0 | 59.4 |
| B2 | | | | | 30.7 | 63.8 |
| B3 | | | | | 29.8 | 61.4 |
| B4 | | | | | 22.7 | 41.9 |
| C1 | 10.4 | 89.6 | 1:1:4/7 | 69.4 | 39.7 | 60.2 |
| C2 | | | | | 42.9 | 65.3 |
| C3 | | | | | 37.5 | 56.6 |
| C4 | | | | | 32.4 | 47.7 |
| D1 | 8.9 | 91.1 | 1:1:0 | 100 | 48.0 | 58.0 |
| D2 | | | | | 48.4 | 58.4 |
| D3 | | | | | 52.0 | 62.3 |
| D4 | | | | | 52.1 | 62.3 |
| D5 | | | | | 45.1 | 54.8 |

$^a$Molar percentages calculated based on GPC peak integrations.
$^b$Sum of $SOS_{pre}$ and maximum theoretical increase in SOS possible assuming quantitative coupling between all added azide- and alkyne-functional SO diblock copolymer in the blend. This increase assumed azide and alkyne functionalization was quantitative following modification.
$^c$Coupling conversions were calculated as the ratio of the measured SOS increase ($SOS_{post}$-$SOS_{pre}$) to the maximum theoretical increase ($SOS_{max}$-$SOS_{pre}$) with quantitative coupling.

Figure 20A:
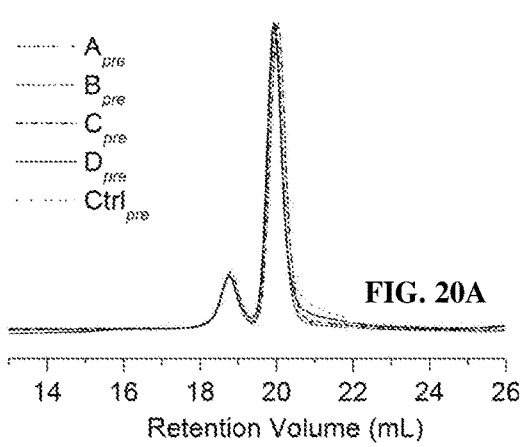
FIG. 20. Representative SEC data for hydrogels formed from blends A through D FIG. 20A before (pre) and FIG. 20B after (post) exposure to the Cu(I) catalyst. All SEC traces were normalized to a constant area under the SO—X diblock copolymer peak (right) to show the relative amounts of SOS triblock copolymer (left peak) more clearly. Control samples contained only SO and SOS.
Figure 20B:
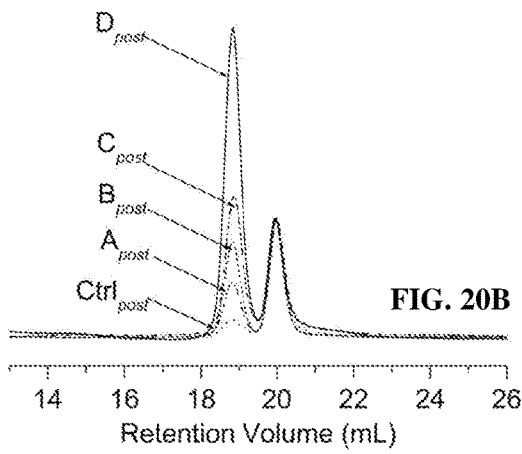

SOS triblock copolymer compositions are based on integration of SEC traces following solution blending (FIG. 20, left). The amount of pre-blended SOS triblock unintentionally varies somewhat (8.9-10.4 mol %) across the four blends, which is attributable to massing error, SEC peak integration, and local variations in blend composition.

Uniform disks (8 mm diameter, 0.24-0.28 mm thickness, 0.015-0.016 g) of samples A through D were prepared via melt pressing at 150° C. for five minutes. Azide-alkyne Huigsen cycloadditions (click reactions) can occur at high temperatures without metal catalyst. Several control experiments were run before and after melt pressing azide-alkyne functional SO and no thermally-induced coupling was indicated in the SEC traces. Molecular weight degradation was also not observed. Functional group integrity during melt pressing proved difficult to accurately assess (via $^1$H-NMR, e.g.) given the reduced concentration of end groups in the blends. However, independent melt processing of neat SO-alkyne showed no change in chain end functionality occurred during heating for such short times.

Each blend sample was prepared by solution blending (1 g total polymer in 20 mL benzene) the appropriate amounts of SO (Example 3), SO-alkyne (Example 12), SO-azide (Example 13), and SOS (Example 4, 10 mol % for all blends) to produce blends containing the specified amount of the "clickable" SO moieties. Solutions were frozen using an ethanol/liquid nitrogen slush bath and then dried under vacuum at room temperature overnight.

Example 15—Swelling and In-Situ Coupling Protocols (DN Formation)

Dry polymer disks of four blends prepared accordingly to Example 14 were placed into a 300-mL round-bottom flasks containing degassed DI water (100 mL) until the equilibrium swelling (~1 hr.) at room temperature. Equilibrated hydrogels were removed the degassed DI water and placed onto a Teflon™ surface. After excess water was blotted, the hydrogels were weighed and returned to the flasks with freshly degassed water (100 mL) and degassed for another 10 minutes. Copper sulfate solution (0.25 mL, 0.007 M, in degassed DI water) and sodium ascorbate solution (1 mL, 0.009 M, in degassed DI water) were injected into the flasks via air-free syringes. The reaction mixture was kept at room temperature overnight. Finally, the hydrogels were left in the degassed DI water for one hour to remove the catalyst before any characterization was performed.

The four blends prepared according Example 14 (A through D) each contained about (1) 8.9 mol % to 10.4 mol % SOS triblock copolymer, (2) varying, equimolar amounts of SO-azide and SO alkyne diblock copolymer, and (3) a balance of reactively inert SO diblock copolymer. The concentration of SO-azide and SO-alkyne were chosen such that the baseline values of 8.9-10.4 mol % SOS in each sample before swelling could be theoretically increased to values ranging from 28.8 mol % (blend A) to 100 mol % (blend D) aggregate SOS triblock copolymer in the final hydrogel network (Table 3).

Figure 21:
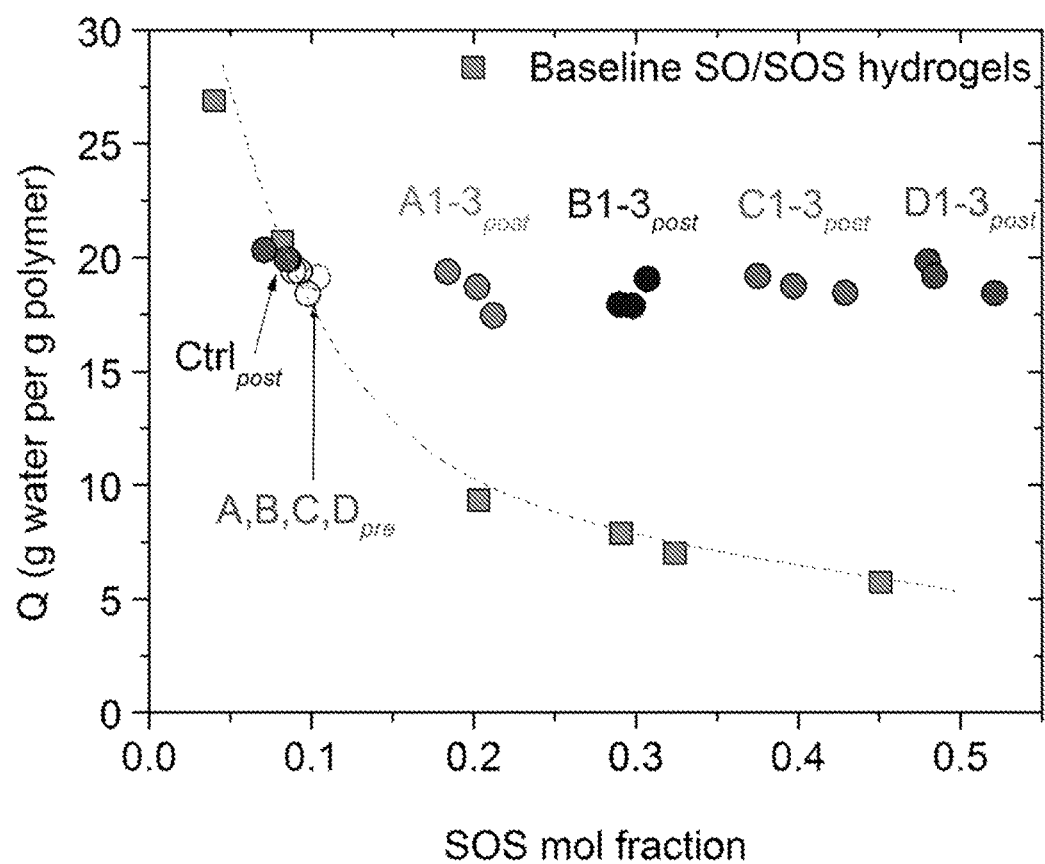
FIG. 21. Hydrogel swelling ratio (Q) as a function of SOS triblock copolymer composition.

Multiple polymer disks were melt-pressed from each of the blends A through D (Table 3). The disks were individually swollen in excess DI water until reaching equilibrium dimensions (about one hour evident by constant mass and size). The Q values for hydrogel disks formed from each blends A through D prior to exposure to Cu(I) catalyst are shown in FIG. 21. The inclusion of SO diblock copolymer that contained terminal azide or alkyne functionality had no particular influence on the equilibrium swelling dimensions compared to that expected from baseline SO/SOS type hydrogels with similar SOS triblock copolymer compositions. That is, all hydrogels from the blends exhibited pre-click Q values in the 18-20 g $H_2O$/g polymer range, consistent with an SOS tether content of 8.9-10.4 mol %. This behavior confirmed the hypothesis that the integration of chain end functionality other than the native hydroxyl at the PEO chain end could be done without disruption of the basic network swelling behavior.

Each hydrogel solution (hydrogel in excess DI water) was degassed with argon before adding sodium ascorbate and copper (II) sulfate. The combination of copper sulfate and sodium ascorbate produces the Cu(I) catalyst in-situ to facilitate the Huisgen cycloaddition reaction between terminal azide and alkyne functional groups of the hydrated PEO blocks. Absent oxygen removal from the hydrogel solutions before adding catalyst, PEO degraded significantly, as verified with SEC. Hydrogel samples were left in the catalyst solution for 24 hours before removal, followed by sequential self-dialysis (osmotic driving force provided by concentration gradient between the hydrogel interior and exterior) against fresh DI solutions to remove residual catalyst. Preliminary kinetic experiments confirmed the 24-hour reaction time was sufficient to reach maximum conversion. Coupling efficiencies were calculated based on the percent of azide (or alkyne) functional groups reacted as quantified through SEC, using the observed SOS triblock copolymer added to the system following exposure to the Cu(I) catalyst. Representative SEC data is shown in FIG. 20 for each of the blends with the results of all coupling reactions summarized in Table 3. Beyond the molecular weight distributions captured in these SEC traces, the data demonstrates the unique ability to deconstruct these TPE hydrogels back into their constituent block copolymer species through removal of water and dissolution in an organic solvent. Even after introducing the secondary network, the hydrogel remained a physically cross-linked mixture of diblock and triblock copolymer, which can be recovered and reprocessed.

A control sample composed of only SO diblock and SOS triblock copolymer, absent azide/alkyne functionality, was also run in parallel to determine the effect of sodium ascorbate and copper (II) sulfate solution on the constituent polymer species. The SEC traces of the control sample before and after exposure to the catalyst system for 24 hours showed no significant change, suggesting neither degradation nor significant side-reactions (FIG. 20). To ensure that coupling in the sample was macroscopically uniform across the bulk dimensions of the sample and not influenced by diffusion limitations in either copper sulfate or sodium ascorbate, SEC was also performed on sections taken from both inner and outer regions of a disk. No significant differences in regional coupling were detected in any samples tested.

SEC analysis of the total SOS triblock copolymer after the post-swelling click chemistry varied from 18.4-52.0 mol %, depending on blend. These values reflected a coupling efficiency that remained almost constant (58.1%±6.3%) across all samples despite variation in the azide/alkyne functional polymer. This likely indicated some degree of non-quantitative functionality in the initial materials (e.g. PS—PEO-azide at <100% functionality). Post-reaction $^1$H NMR and FTIR indicated both azide and alkyne groups were still present in small amounts, although the size of the block copolymers have made quantification unreliable.

In addition to non-quantitative functionality in SO-azide (or SO-alkyne), performing the reaction within the context of a fixed morphology also determined coupling efficiency. The self-assembled sphere morphology placed PEO chains of the corona close to those belonging to adjacent spherical domains. This structure spatially directed or concentrated terminal azide and alkyne groups into defined regions, which should enhance coupling efficiencies when the number of functional chain ends in the region was high (as it was at low conversions). The reaction volume available to each functional group was constrained by the limited travel available to each PEO chain end, given the opposing end was anchored to a fixed junction point (spherical domain) in the network. As the conversion proceeds to higher values, and residual functional group concentrations diminished, the occurrence of orphaned chain ends was likely.

The post-click Q values for three hydrogels from each blend type are given in FIG. 21 as a function of their new total SOS triblock copolymer compositions. Installing additional SOS triblock copolymer through click coupling under equilibrium swelling conditions had no significant influence on the water content of the hydrogel. That is, the Q values still reflected the SOS triblock copolymer composition before swelling. Q values for the baseline SO/SOS hydrogels are included in FIG. 21 and provide a direct comparison between hydrogels of similar total SOS triblock copolymer compositions, differing only in how the triblock copolymer were introduced into the system.

To summarize, one can predetermine water content by selecting the percentage of SOS triblock copolymer used during melt-state self-assembly. The post-swelling click chemistry then provided an additional, secondary network of SOS tethers while preserving the original Q values.

Example 16—Dynamic Shear and Unconfined Compression Testing

The rheology and unconfined compression test results for the samples of Example 15 were collected on a TA Instruments ARES rheometer at room temperature using parallel plate geometry with an infinite lower plate and an 8-mm upper plate. The bottom plate was the bottom of an integrated glass cup outfitted with a humidified cover. The swollen hydrogels were placed onto the bottom plate with excess water blotted away. The hydrogel thicknesses were measured on the rheometer and determined by the gap value between the parallel plates when the normal force on the upper plate reached 2 grams force. Since all unstrained hydrogels exceeded 8-mm diameters, the stresses were calculated from the fixed upper plate dimensions. To eliminate slip between the upper plate and the hydrogel samples during the rheological property measurements, 10% compressive strain was applied on each hydrogel sample. Dynamic frequency sweeps were performed on each sample using a shear strain in the range of 0.15-3% (linear viscoelastic region) over a frequency of 0.1 to 100 rad/s. For unconfined compression tests, the gels were compressed to 40% using a rate of 20%/minutes Two compression-decompression cycles were performed to study the possible hysteresis also using the rate of 20%/min during decompression.

Figure 22:
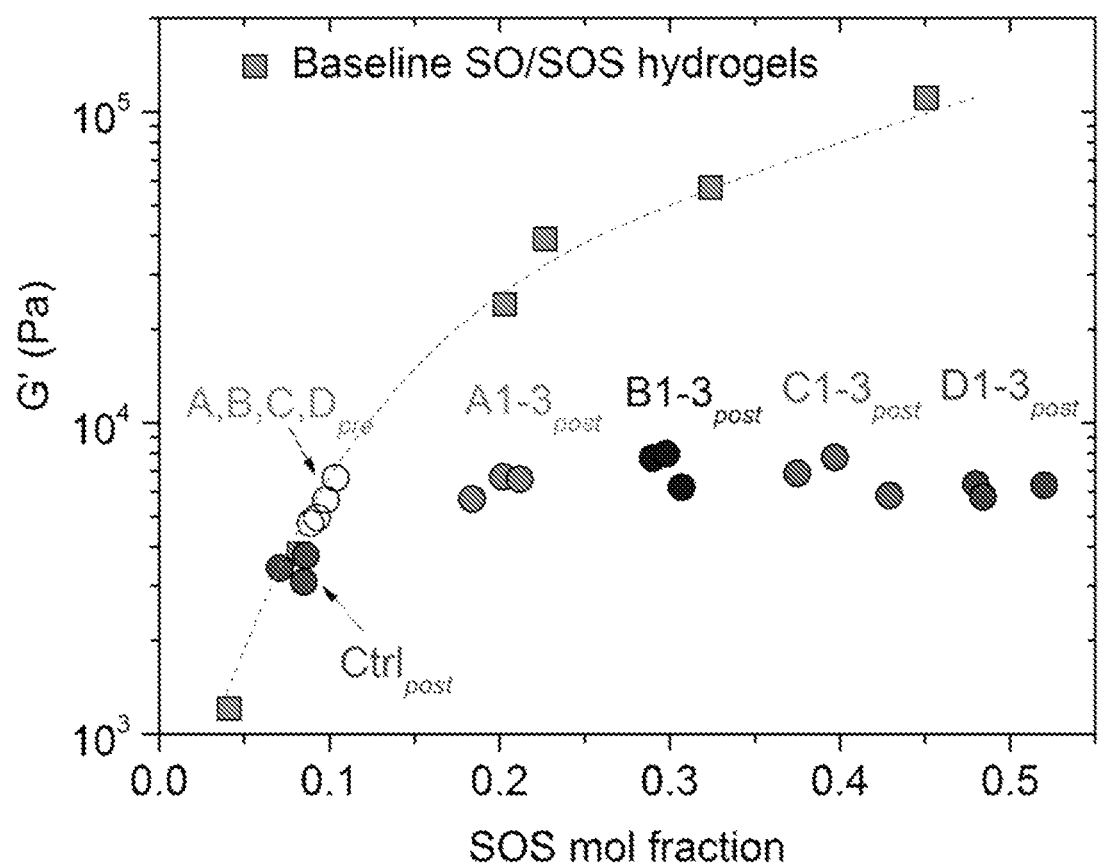
FIG. 22. Elastic moduli under dynamic shear ($\omega$=1 Hz) as a function of total SOS triblock copolymer composition.

FIG. 22 shows the pre-click and post-click elastic moduli of hydrogels formed from the four blends A through D. The elastic moduli of the six SO/SOS TPE hydrogels were also included for direct comparison of the post-click DN hydrogels with baseline hydrogels of similar SOS content. As a control experiment, baseline SO/SOS hydrogels (no azide or alkyne functionality present) with approximately 8.5 mol % SOS triblock copolymer were soaked in argon-degassed catalyst solutions for the standard 24-hour reaction time. Their elastic moduli were also included in FIG. 22. The control samples established the effect of the catalyst solution on the mechanical properties of the hydrogel independent from the SOS tethers. As shown in FIG. 22, the elastic moduli after catalyst solution exposure remained very similar to that of the unexposed 8.5 mol % baseline hydrogel (original frequency sweep data is provided in the supplementary information). Thus, the impact of the catalyst solution exposure on elastic modulus was regarded to be negligible.

The effect of adding azide and alkyne chain end functionality (unreacted) towards the elastic modulus of the hydrogel appears to be largely minimal. Examples of the elastic moduli of the four blends before adding catalyst solution fell along the trajectory for the baseline SO/SOS hydrogel systems. That is, the chain end functionality in its uncoupled state has not limited the elastic properties of the hydrogels under dynamic shear.

A comparison of the elastic moduli of hydrogels under dynamic shear, containing azide/alkyne functional groups both pre- and post-click reveals an apparent increase in elastic modulus (20 to 40%) upon installation of additional SOS triblock copolymer. Compared with baseline TPE hydrogels of similar total SOS triblock copolymer compositions, these increases in modulus (from introducing the second network of tethers) were modest. For example, adding tethers post-swelling to get from 8.9 mol % SOS to 48 mol % SOS triblock copolymer (sample D1) increased the elastic modulus from 4.7 to 6.3. By comparison, baseline SO/SOS hydrogels with 45.1 mol % SOS triblock copolymer in which the entire population of tethers were introduced during melt-state self-assembly exhibits an elastic modulus of just over 100 kPa. This comparison underscored the very limited impact the secondary network, installed post-swelling, had on the small strain shear response of these hydrogels. At small oscillatory strains (<3%), the secondary network, containing almost four times the number of tethers as the primary network, remained largely passive. This is a direct reflection of the stress free environment under which these tethers are installed. The elasticity of these hydrogel networks was governed predominately by PEO coronal overlap with adjacent spherical domains. The small improvement in elastic modulus was likely a product of the changes in how adjacent coronal layers are connected, without a pronounced difference in coronal layer overlap, the changes detected remain quite modest.

Figure 23A:
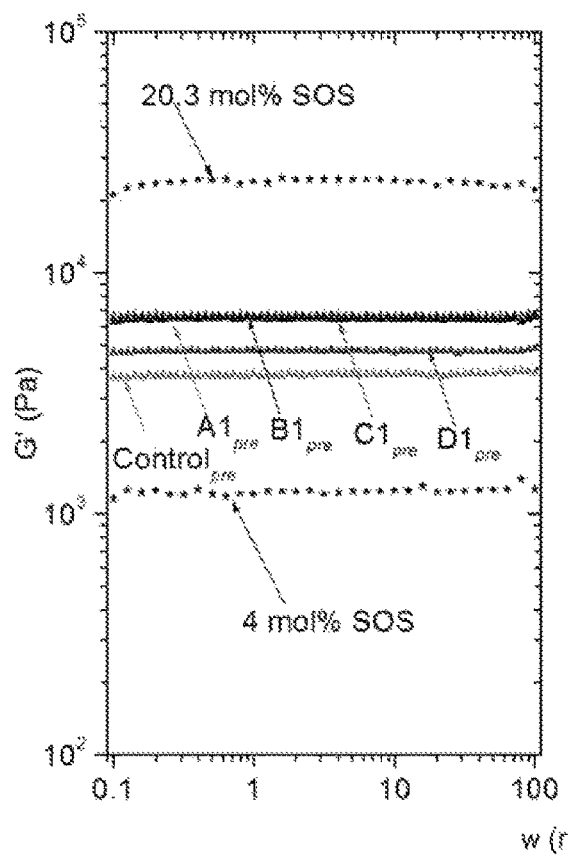
FIG. 23. Representative dynamic frequency sweep results showing the elastic moduli for samples A1-D1 before testing (FIG. 23A) and after testing (FIG. 23B), two baseline SO/SOS hydrogels of 4.1 and 20.3 mol % SOS, and a baseline SO/SOS hydrogel soaked in catalyst solution for 24 hours (control).
Figure 23B:
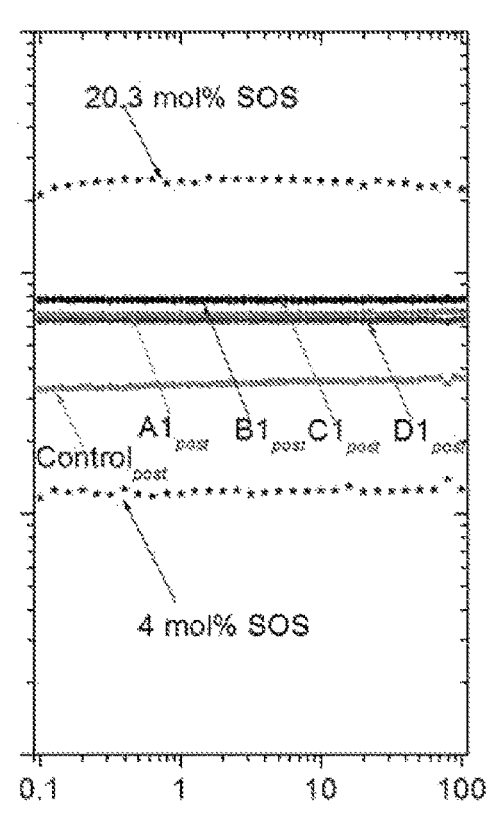
Figure 24:
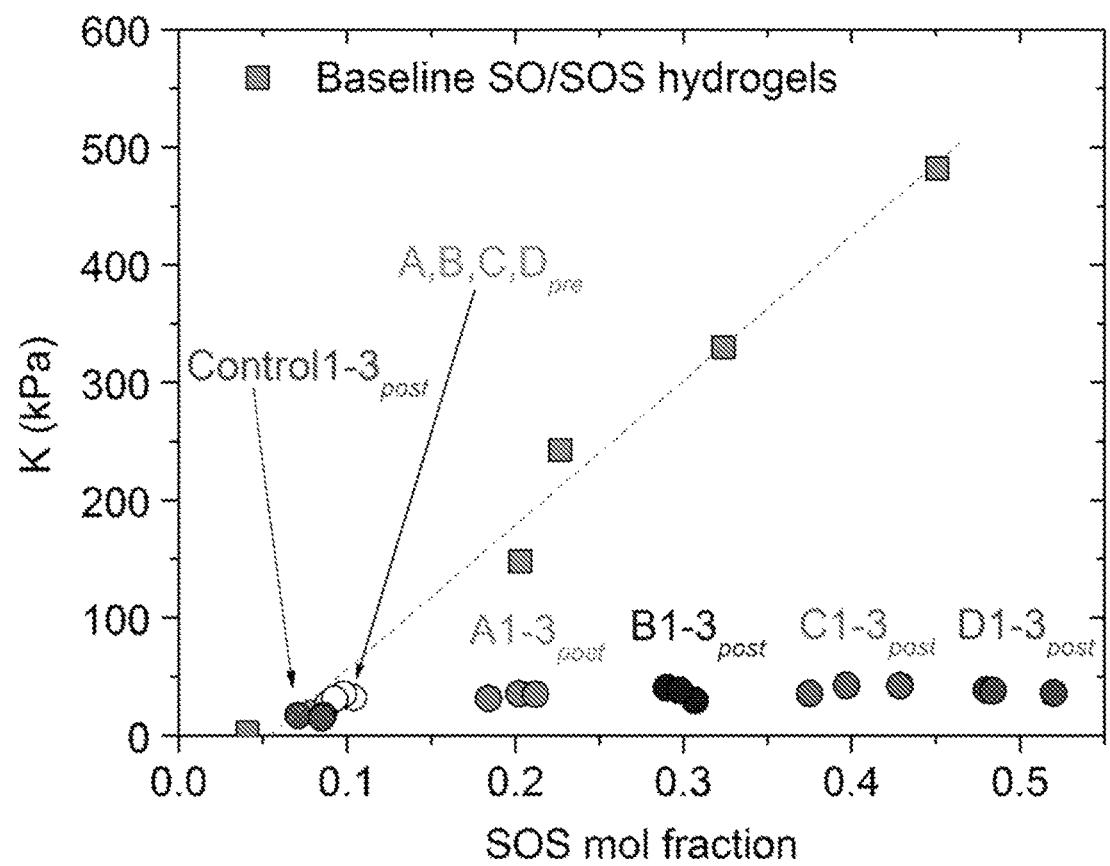
FIG. 24. Compressive moduli in unconfined compression (strain rate=20% $min^{-1}$) as a function of the total SOS triblock copolymer composition.

The behavior of the post-click DN hydrogels in unconfined compression (to 40% strain) produced similar conclusions (FIGS. 23 and 24). As with the baseline SO/SOS hydrogels, all samples, regardless of treatment, produced linear stress-strain relationships to 40% strain (strain rates at 20% $min^{-1}$) and exhibited some hysteresis during decompression, but ultimately showed complete elastic recovery with second compression/decompression cycles coinciding the first cycle. Baseline SO/SOS control samples exposed to catalyst solutions for the 24-hour reaction time performed similarly to unexposed baseline hydrogels. Pre-click samples gave compressive moduli consistent with those produced by baseline SO/SOS hydrogels of similar SOS triblock copolymer compositions. The installing additional SOS triblock copolymer post-swelling resulted in small increases in compressive modulus across samples compared with their pre-click counterparts, but as with elastic modulus, the increase was very modest when compared with baseline SO/SOS hydrogels of similar total SOS content.

Figure 25A:
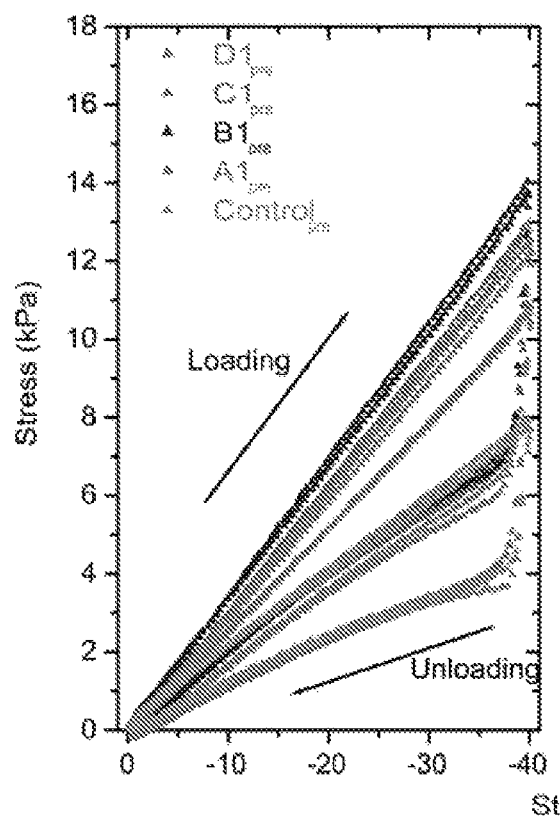
FIG. 25. Representative unconfined compression results showing the stress-strain relationships for samples A1-D1 before testing (FIG. 25A) and post-testing (FIG. 25B), and a baseline SO/SOS control hydrogel soaked in catalyst solution for 24 hours (control).
Figure 25B:
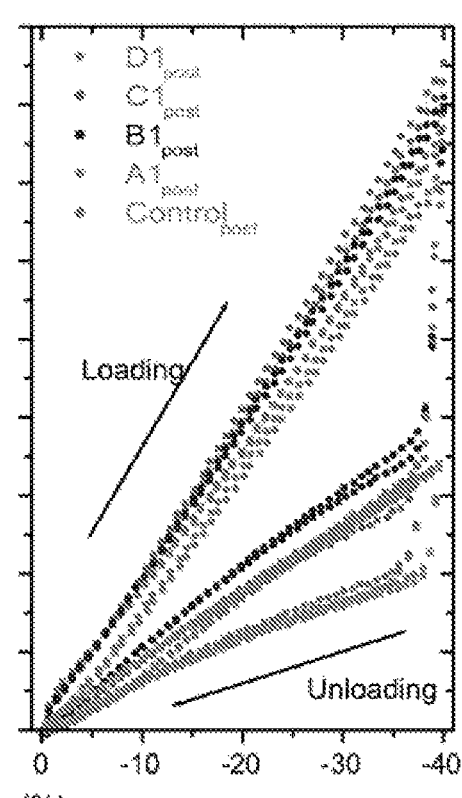

Using sample D1 as an example, the pre-click (8.9 mol % SOS) and post-click (48.0 mol % SOS) compressive moduli were 27 kPa and 38 kPa respectively, demonstrating the marginal effect of the secondary SOS network on compression response of the hydrogel. By comparison, the baseline SO/SOS hydrogel of 45.1 mol % SOS exhibited a compressive modulus of 482 kPa. The post-click DN data suggested that even at 40% compression, the secondary network of SOS tethers still failed to engage to an extent that allowed it to contribute significantly to the mechanical response of the hydrogel, even with four times as many tethers as the primary network. The SOS triblock copolymer of the primary network introduced during melt-state self-assembly was still the dominant factor determining compressive properties. Original compression data for the baseline SO/SOS control samples, as well as the pre- and post-click samples A1-D1 are included in FIG. 25.

Example 17—Tensile Testing of Swollen Hydrogels

Tensile tests were carried out on rectangular pieces of hydrogel samples prepared according to Example 15 cut to about 14-mm width with thickness that varied from 0.442 mm to 0.875 mm. Multiple test coupons were cut from each hydrogel disk to maximize sample size within a letter group (e.g., disks B1, B2 and B3 produced six viable test coupons). All tensile tests were run at room temperature using the normal force transducer of a TA ARES rheometer. TA rectangular torsion geometry test fixtures were used as tensile test grips with added 600 grit sand paper. A strain rate of 5 mm/s was applied until complete hydrogel fracture. The strain rate was chosen to minimize slip while ensuring the maximum travel distance could be covered in less than 0.5 minutes, such that surface evaporation during testing could be minimized. Stress was calculated as the force normalized by the initial cross sectional area of each sample (engineering stress).

Figure 26:
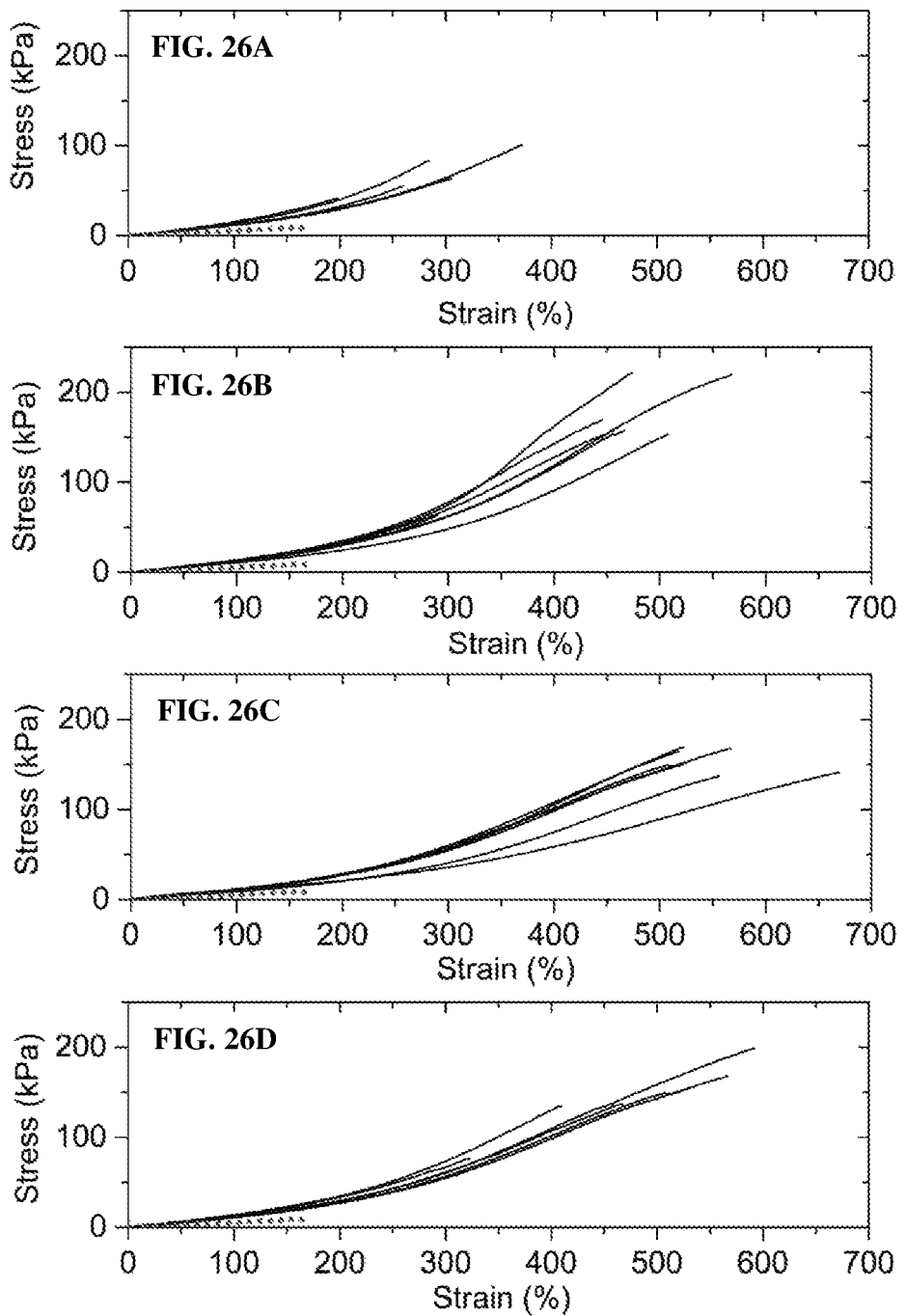
FIGS. 26A-D. Tensile test results for hydrogels formed from blend A (FIG. 26A), blend B (FIG. 26B), blend C (FIG. 26C), or blend D (FIG. 26D), evaluated after installation of the secondary network of SOS triblock copolymer. Total SOS triblock copolymer compositions can be found in Table 3.

The secondary network of SOS tethers provided a stunning enhancement in hydrogel fatigue resistance possible while maintaining very high Q values. FIG. 26 shows the tensile tests from a series of post-click DN samples A through D. Multiple test coupons could be tested from each sample disk (i.e. disks B1, B2 and B3 produced six viable test coupons) and combined to produce the four plots of FIG. 26. Similar control experiments on baseline SO/SOS hydrogels exposed to the catalyst solution for 24 hours, as well as pre-click blends A through D, showed tensile behavior similar to that expected for baseline SO/SOS hydrogels of similar SOS content. The post-click blends A through D showed dramatic improvements in virtually all tensile property categories. Tensile test results for the unmodified baseline 8.5 mol % SOS hydrogel of similar Q, but without the clicked functional groups underscore the dramatic improvements to fatigue resistance possible.

Table 4 summarizes the basic tensile properties for each of the hydrogel blends A through D, with analogous data for the performance of the baseline SO/SOS hydrogels. Each hydrogel formed from blends A through D has a swelling ratio in the range of 18-20 g $H_2O$/g polymer, and was therefore comparable with the 8.5 mol % SOS baseline hydrogel.

(2- to 3-fold) and Young's modulus (2-fold) compared with the 8.5 mol % SOS baseline hydrogel of equivalent Q value. Incredibly, the secondary network, even at the moderate levels produced in the B blends, provides hydrogels with Q values of 18-20 g $H_2O$/g polymer the tensile properties typically available only to hydrogels of much lower water content.

Without wishing to be bound by theory, the dramatic impact of the secondary SOS network under tension (compared to small strain shear or unconfined compression) was a product of its ability to reinforce the primary network at higher strains. Because it is largely formed in an unperturbed state, the topological entanglements of the secondary network required much higher strains to become mechanically engaged. As such, they provided the hydrogel network an improved range over which strain energy can be absorbed. That is, as the primary network approached its mechanical limit, it gradually transferred load to the secondary network, extending the strain and stress to break. Consequently, the additional tethers improved the elongation capacity of the hydrogels. Overall, the post swelling click chemistry provided a means of adjusting the tensile properties of these tethered micelle based hydrogels largely independent of other mechanical properties.

Figure 27:
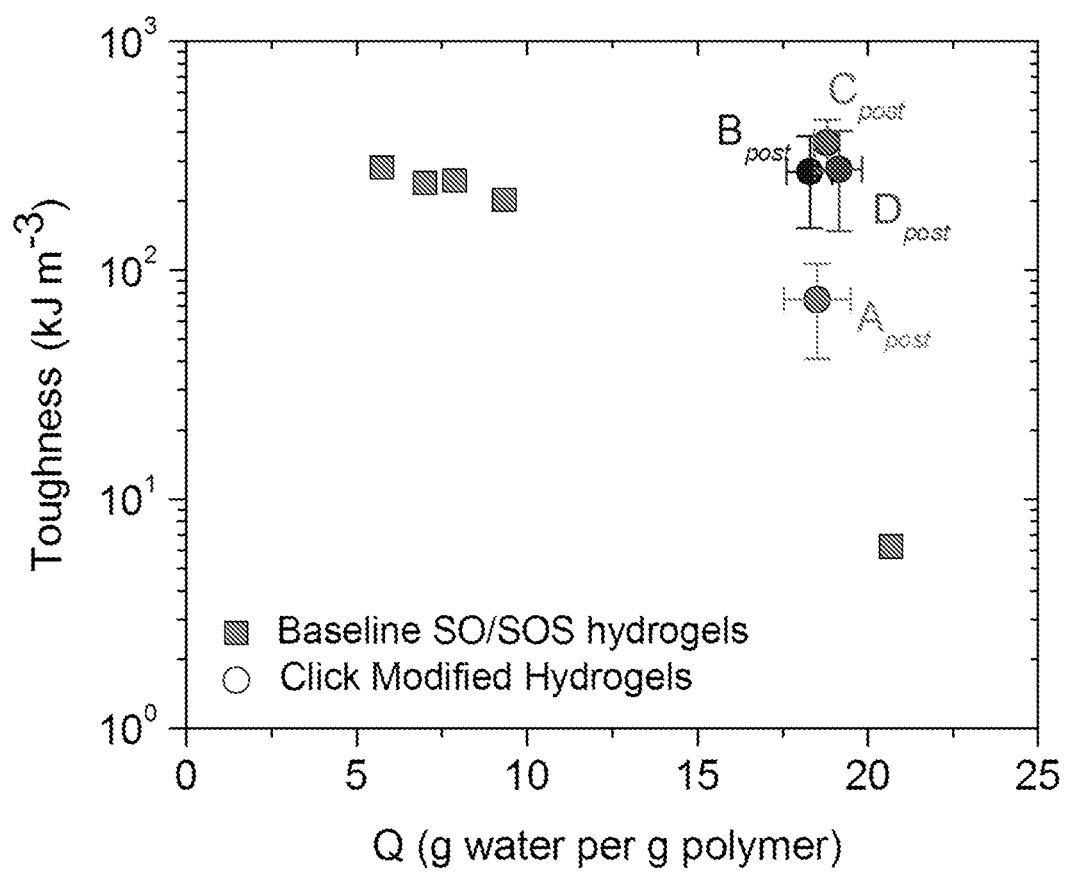
FIG. 27. Hydrogel fatigue resistance as a function of Q. The fatigue resistance and Q data can be found in Table 4.

The stress-strain plots in FIG. 27 gave a sense of the scatter in the tensile response typical given simple melt-pressing under atmospheric conditions. Thus, the measured tensile properties were likely influenced by bubble, grain boundary and edge defects present before and after swelling. As a consequence, the vast improvements in tensile properties were likely understated.

Unlike traditional DN hydrogels, the first and second networks in this diblock-triblock system derived from the same molecular constructs, with the elements of the second network intrinsically present, yet dormant until activated. The strategy preserves the chemical composition of the hydrogel while employing a stepwise installation process to form two chemically identical tethering populations, each under a different degree of mechanical (osmotic) stress. With

TABLE 4

Mechanical properties of baseline TPE hydrogels and post-click DN hydrogels.

| Sample | $SOS_{post}$ (mol %) | Q (g water/g polymer) | Strain to break (%) | Stress to break (kPa) | Young's modulus (kPa) | Fatigue Resistance (kJ/m$^3$) |
|---|---|---|---|---|---|---|
| Baseline | 4.1 | 26.9 | — | — | — | — |
| SO/SOS | 8.5 | 20.7 | 154 | 8.7 | 5.3 | 6.2 |
| Hydrogels | 20.3 | 9.3 | 375 | 107 | 38 | 203 |
|  | 29.2 | 7.9 | 293 | 150 | 82 | 246 |
|  | 32.4 | 7.0 | 254 | 160 | 110 | 240 |
|  | 45.1 | 5.7 | 195 | 237 | 209 | 280 |
| A | 20.0 ± 1.2 | 18.5 ± 1.0 | 287 ± 58 | 68 ± 21 | 12.0 ± 1.5 | 74 ± 33 |
| B | 28.1 ± 3.6 | 18.3 ± 0.7 | 458 ± 85 | 163 ± 53 | 12.5 ± 1.2 | 269 ± 116 |
| C | 38.1 ± 4.4 | 18.8 ± 0.4 | 567 ± 56 | 169 ± 34 | 11.2 ± 1.5 | 361 ± 93 |
| D | 49.1 ± 3.0 | 19.2 ± 0.7 | 479 ± 103 | 135 ± 30 | 13.1 ± 1.2 | 276 ± 127 |

Table 4 and FIG. 27 show that adding the secondary network vastly improved both fatigue resistance and stress to break. With only a single, primary network of SOS tethers, the 8.5 mol % SOS hydrogel (~95% $H_2O$ by mass) could absorb 6.2 kJ m$^{-3}$ before fracture at stresses as low at 8.7 kPa. With the secondary network of tethers, both the fatigue resistance and stress at break could be improved dramatically, with samples from blend C reaching mean values of 361 kJ m$^{-3}$ (a 58-fold increase) and 169 kPa (a 19-fold increase), respectively. Similarly, the secondary network of SOS tethers significantly improved strain to break the exception of the Cu(I) catalyst here, forming secondary network by this route could potentially eliminate concerns associated with leaching in traditional DN hydrogel systems.

Example 18—General Procedure for Forming Hydrogel Membranes

The press was set to 150° C. A mixture of PS—PEO (SO, Example 3) and PS—PEO—PS (SOS, Example 4) was placed into a mold between two Kapton™ sheets and pressed at 500 psig for 5 minutes, at which point the SO—SOS melt was removed.

To reduce bubbling and cracking, the assembly was placed it into a vacuum bag and repressed at the same pressure, temperature, and time while applying vacuum using a membrane pump. This process was repeated until no bubbles were visible, typically requiring 2 to 4 cycles of removing the sample, letting the sample cool to room temperature, and placing it back into the press for another run under vacuum. Once the process was completed, the sample was removed from the mold, excess material was trimmed, and the sample was swelled in water or aqueous buffer for at least 24 hours.

Using a processing temperature 100° C. or cooler took longer, but the same effect was obtained. The higher pressure (500 psig) seemed to speed up the process on the removal of bubbles. Without wishing to be bound by theory, the repeated cycling process may concentrate the polymer into a smaller volume.

Example 19—Hydrogel Membrane Fabrication and Characterization

Membranes were fabricated by sandwiching 0.05 g of the desired diblock/triblock SO—SOS copolymer blend (see e.g. Example 7 above) between two Kapton™ sheets and pressed in a Carver, Inc. manual heating press at 1,000 lbs. force and 125° C. for 10 minutes. The Kapton™-sandwiched membrane was then placed in a vacuum bag and re-pressed at the same pressure and temperature (22-24° C.) conditions for another 15 minutes under vacuum of 5 torr. The membrane was allowed to cool to room temperature for 15 minutes This procedure was repeated three times for each membrane, during which the pressure was increased by 5000 lbs. force in each successive press. After three vacuum-press cycles, defect-free polymer films ranging from 55-190 μm in thickness were obtained. (For comparison, please refer to Examples 6 and 17 above.)

The dry films were swollen in excess vacuum-dried 1-ethyl-3-methylimidazolium bis(trifluoromethanesulfonyl) imide ([EMIM][TFSI]) for 20 hour under vacuum at ambient temperature. The resulting RTIL-hydrogel membranes were allowed to reach equilibrium swelling dimensions (about 20 hour swelling time) before being removed from the RTIL and lightly patted dry with Kimwipes™ to remove excess [EMIM][TFSI]. Membranes were cut to 47-mm diameter discs using a punch and were mount in a Millipore™ membrane testing unit.

Thicknesses of the dry and swollen RTIL composite membranes were measured on a ZeScope™ optical profilometer (Zygo, Middlefield, Conn.). Attenuated total reflectance infrared (ATR-IR) measurements were performed on a Nicolet™ iS50 FTIR (16 scans, 2 cm$^{-1}$ resolution). Small Angle X-ray Scattering (SAXS) was used to characterize the melt-state morphology of the SOS22 and SOS46 blends. SAXS data were collected on a Rigaku S-Max 3000 High Brilliance 3 Pinhole SAXS system outfitted with a Micro-Max-007HFM Rotating Anode (CuKα), Confocal Max-Flux™ Optic, Gabriel Multiwire Area Detector and a Linkham thermal stage, as in Example 7B above. Pressed membrane samples were mounted on the thermal stage and heated to 170° C., then cooled to 120° C. before data collection. Three-hour exposure times maximized signal-to-noise ratios for Percus-Yevick data fits.

Single-gas $CO_2$ and $N_2$ permeability measurements were performed using a time-lag apparatus. Experiments were performed across a range of pressures on three SOS22 and four SOS46 membrane samples. Experiments were performed at ambient temperature (22-24° C.). Between experiments the apparatus and membrane were evacuated for at least 6 hours using an Edwards RV8 vacuum pump. Data from the steady-state region was used to calculate the flux (J), permeability (P), and gas diffusivity ($D_i$) from Equations 3, 4, and 5.

$$J_i = \left(\frac{\Delta p_i}{\Delta t} - \frac{\Delta p_{leak}}{\Delta t}\right) \cdot \frac{V}{A \cdot T} \cdot \frac{273.15}{14.504} = \frac{\Delta V_i(stp)}{A \cdot \Delta t} \quad \text{(Equation 3)}$$

Equation 3 determined steady-state flux ($J_i$) ($cm^3$ (STP)·$cm^{-2}$·$s^{-1}$), where $\Delta p_i$ was the change in permeate pressure (psi); $\Delta t$ was the change in time (s); $\Delta p_{leak}$ was the change in the permeate pressure when system was evacuated then sealed (psi); i.e., the 'leak rate'; V was the permeate volume ($cm^3$); A is the membrane area ($cm^2$); T was the temperature (K); and $\Delta V_i$ was the volume of gas accumulated in the permeate volume at standard temperature and pressure.

$$P_i = \frac{J_i}{\Delta P_i} \cdot l \quad \text{(Equation 4)}$$

Equation 4 determined the permeability ($P_i$) (barrers), where $J_i$ was the flux ($cm^3$ (STP)·$cm^{-2}$·$s^{-1}$); l was the membrane thickness (cm); and $\Delta P_i$ was the trans-membrane pressure difference (cm Hg).

$$D_i = \frac{l^2}{6\theta} \quad \text{(Equation 5)}$$

Equation 5 determined the diffusion coefficient ($D_i$) (($cm^2$·$s^{-1}$), where l was the membrane thickness (cm) and θ was the time-lag (s). The time lag (θ) was determined from the x-axis intercept from a plot of the steady-state flow rate ($V_i$ (STP)) against time (t).

The solution-diffusion model extracted the permeability, diffusivity, and solubility from the raw experimental data (flux) using Equations 3-6. The ideal selectivity ($\alpha_{i/j}$) between the two gases (i and j) was calculated using Equation 6. The membranes reported herein are free-standing, dense films, so no tortuosity and porosity corrections were applied.

$$P_i = D_i \cdot S_i \quad \text{(Equation 6)}$$

Equation 6 calculated the $P_i$, the permeability of gas i (barrers), where $D_i$ was the diffusion coefficient of gas i ($cm^2$/s) and $S_i$ was the solubility coefficient of gas i ($cm^3$ of i at STP·$cm^{-3}$ of polymer·$atm^{-1}$).

$$\alpha_{i/j} = \frac{P_i}{P_j} \quad \text{(Equation 7)}$$

Equation 7 calculated $\alpha_{i/j}$, the ideal selectivity, where $P_i$ was the permeability of the faster gas 'i' (barrers) and $P_j$ was the permeability of the slower gas (barrers).

Example 20—Mechanical Testing of the Membranes

Tensile tests on rectangular samples prepared according to Example 19 were run on a TA Instruments ARES rheometer with rectangular geometry test fixtures. Dimensions of the samples were about 6-mm wide and between about 0.2-mm and about 0.3-mm thick. All tensile tests were run at room temperature using the normal force transducer. The surfaces of the transducer grips were modified with 600-grit sandpaper to eliminate the slip on the sample. An initial force of 1 g was applied to the sample and strain rate of 2% s$^{-1}$ from the initial length was applied until mid-sample failure occurred. Stress was calculated as the force normalized by the initial cross sectional area of each sample (engineering stress). Strain at failure ($\lambda_f$) was used for calculating the cyclic loading intervals for the cyclic load testing. A strain rate of 2% s$^{-1}$ from the initial length was maintained for loading cycles. (FIG. 30.)

Multiple extension mode strain controlled transient compression tests were performed on a TA instrument ARES rheometer with parallel plate fixtures using the integrated normal force transducer. An upper plate (25 mm in diameter) was used with an infinite diameter lower plate (63 mm). The sample diameter was 20 mm and 2.2 mm thick. The sample was placed in the center of the lower plate stage and initial normal force of 10 g was applied. A strain rate of 10% s$^{-1}$ from the initial thickness per second was applied on the sample up to 40% strain. Multiple cycles of normal compressive force loading and unloading were measured.

All membranes were formed using pre-blended SO diblock and SOS triblock copolymer as described in Table 5 and FIG. 31.

TABLE 5

Characterization of membrane composition and mechanical properties.

| Blend | SOS Loading (mol %)[a] | RTIL Loading (wt %)[b] | Q[c] | $\lambda_f$[d] | UTS (kPa)[e] | Compressive Modulus (kPa)[f] |
|---|---|---|---|---|---|---|
| SOS22 | 22 | 94.8 | 18.4 | 3.8 | 80 | 71 |
| SOS46 | 46 | 94.0 | 16.5 | 3.8 | 250 | 348 |

[a]Composition of un-swollen BCP membranes;
[b]RTIL weight percent in a swollen membrane;
[c]Equilibrium swelling ratio of the membranes defined as the grams of liquid/gram of polymer;
[d]Extension ratio at break (failure) under tensile loading;
[e]Ultimate tensile strength;
[f]Compressive modulus at 40% strain.

FIG. 31 illustrates membrane fabrication. FIG. 31A is cartoon representation of polystyrene-b-poly(ethylene oxide)-polystyrene triblock (SOS) and polystyrene-b-poly(ethylene oxide) diblock (SO). FIG. 31B shows chemical structure of SOS and SO. FIG. 31C shows the melt state self-assembly of SO/SOS blend with heat; polystyrene blocks in spherical domains with poly(ethylene oxide) coronas and tethers (highlighted in bold). FIG. 31D shows a melt-pressed film before RTIL loading. FIG. 31E shows the swelling of self-assembled film in RTIL with preservation of tethered spherical morphology. FIG. 31F is an example of an elastic free-standing membrane of SOS46 loaded with 94 wt % RTIL.

The naming convention used is based on designating the mol % triblock copolymer in the sample following the SOS label. For example, the SOS22 membrane comprises a blend of 22 mol % SOS triblock copolymer and 78 mol % SO diblock copolymer prior to RTIL loading (FIG. 31B).

The desired nanostructure of the SO/SOS blends was achieved by designing the volume fraction of PS ($f_{PS}$=0.079) to fall into the sphere-forming regime of the typical AB diblock copolymer phase diagram. Simultaneously, the ultimate mechanical performance of the SO/SOS blends was achieved by maintaining a PS molecular weight (8320 g·mol$^{-1}$) capable of vitrification (a glass transition) above the PEO crystallization temperature of 65° C. The latter ensured trapping the spherical domain structure before PEO crystallization and guarantee the mechanical integrity of those domains, even at elevated temperatures. Melt state self-assembly facilitated forming a homogeneous periodic domain structure as suggested by FIG. 31B. SAXS confirmed the targeted spherical morphology and coincident principal domain spacing of 32 nm for both the dry SOS22 and SOS46 melt blends.

Figure 32:
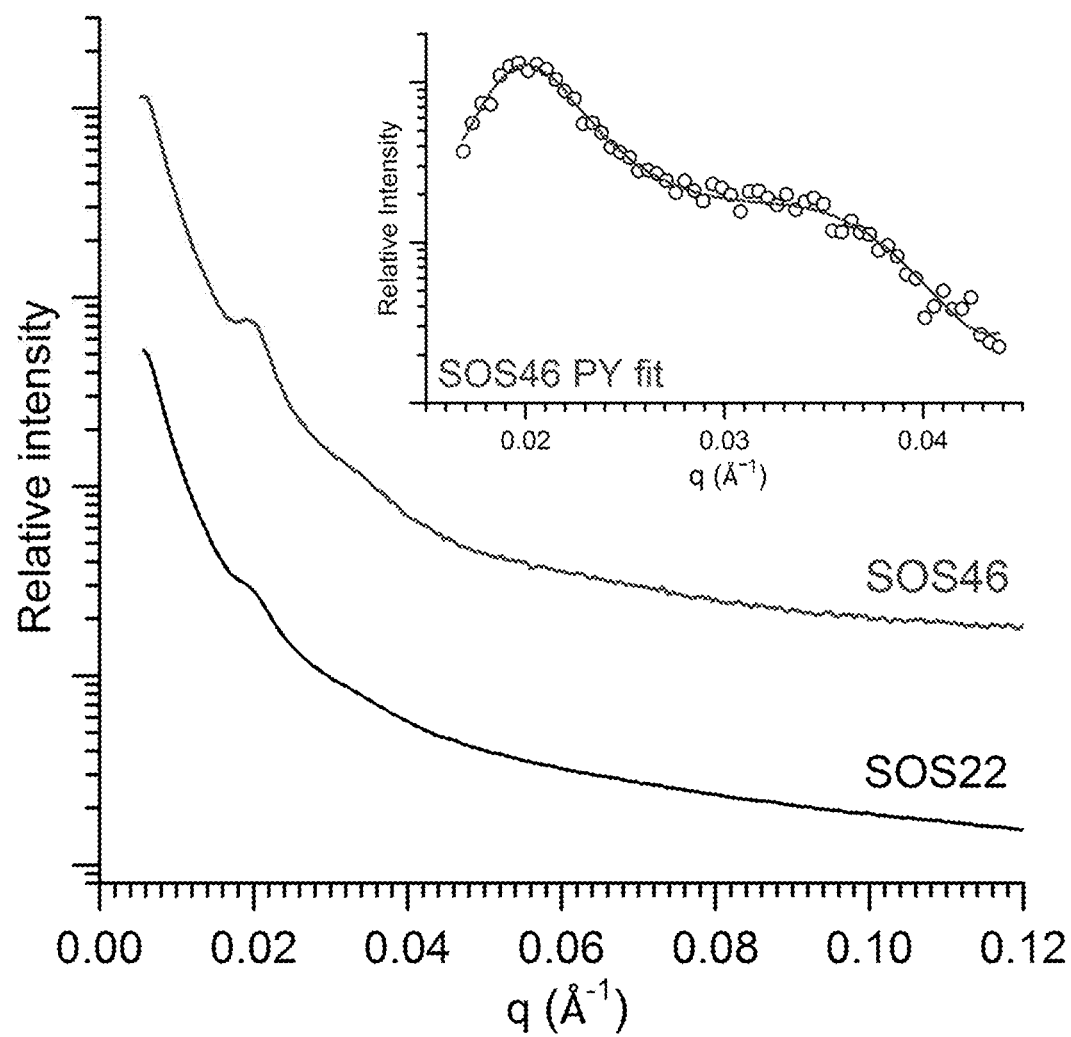
FIG. 32. 1D azimuthally integrated SAXS data for SOS22 and SOS46 in the melt at 120° C. just before vitrification.

FIG. 32 shows the one-dimensional 1D azimuthally integrated SAXS data for SOS22 and SOS46 in the melt at 120° C. just before vitrification. The primary peak and adjacent broad shoulder were typical scattering signatures for SOS blends exhibiting a liquid-like packing of spheres. Fits of the SOS46 data (inset) to a Percus-Yevick hard sphere model for polydisperse spheres confirmed a polystyrene core radius of about 10.5 nm, with a principal domain spacing of about 32 nm. While the signal contrast in the SOS22 scattering data was too weak to perform a reliable Percus-Yevick fit, the coincidence of the principal scattering peak position (q*=0.020 Å$^{-1}$) and similarity of the scattering profiles strong indicated the structural similarity in these two SOS blends. (See also Example 7 above.)

Structural characteristics of the pre-swollen networks were extracted from SOS46 data fitted with a modified Percus-Yevick hard sphere model. These fits confirmed a liquid-like packing of the spherical domains, an aggregation number of approximately 340 chains per sphere, and PS core radii of 10.5 nm. (See Table 6.)

TABLE 6

Chemical and melt-state morphological characterization data of block copolymer blends

| | Tether added | | | | Percus-Yevick hard sphere model | | | |
|---|---|---|---|---|---|---|---|---|
| Sample | (mol %) | q*/Å$^{-1}$ | d*/nm | $f_{PS}$ | $R_c^a$/nm | $\varnothing_c^b$ | $\theta_{PS}^c$ | $R_{hs}^d$/nm | $\varnothing_{hs}^e$ |
| SOS22 | 22.0 | 0.0197 | 31.9 | 0.079 | — | — | — | — | — |
| SOS46 | 46.0 | 0.0196 | 32.0 | 0.079 | 10.5 | 0.108 | 340 | 17.0 | 0.46 |

[a]Micelle core radius,
[b]Micelle core overall volume fraction, $\varnothing_c = (R_c/R_{hs})^3 \varnothing_{hs}$, based on the PY parameters,
[c]Mean aggregation number (i.e., PS chains per sphere), based on the PY parameters,
[d]apparent hard sphere radius,
[e]hard sphere volume fraction.

These data corresponded to trillions of spherical domains per milligram of dry polymer blend, which when tethered together by SOS triblock copolymer produced an extremely efficient network which distributed stress across the sample. When the polymer film was loaded with RTIL, the dense PEO matrix formed by the coronal layers surrounding each sphere were selectively swollen, forming a continuous RTIL/PEO domain structure that traversed the entire expanse of the membrane. Analysis of swelling in analogous tethered sphere systems showed the increase in average spacing between spherical domains measured by SAXS is identical to that predicted by macroscopic expansion in membrane dimensions upon swelling. This continuous domain structure could easily absorb both tensile and compressive strains, while excellently transporting gas through the membrane. The vitrified PS cores remained impervious to the RTIL and provided solid multifunctional junction points anchoring the tethered network in-place. Even with RTIL loadings approaching 95 wt %, this framework granted the membrane solid-like mechanical properties. Without wishing to be bound by theory, the PS molecular weight of 8320 g mol$^{-1}$ guaranteed the cores remain vitrified at temperatures up to 80° C.

A single melt-processing step (molding under a hot press) was used to self-assemble the SO/SOS blends into the desired nanostructured free-standing film (FIG. 31B). The thickness of each film was reduced by repeating the melt-pressing process under vacuum while step-increasing the applied pressure. Typical dry film thicknesses ranged between about 55 μm and about 190 SO/SOS films containing two different SO/SOS ratios were swollen with excess [EMIM][TFSI] to produce the desired composite membranes (FIG. 31C and Table 5). The equilibrium swelling ratios (Q) were calculated based on gravimetric analysis of the membranes before and after swelling with RTIL, producing final membrane thicknesses falling between 135 μm and 430 μm. The thickness of each membrane was measured using an optical profilometer.

The concentration of SOS triblock copolymer in the blend dramatically influenced the swelling ratio and mechanical properties when water was the swelling medium ($Q_{H2O,\,22\,mol\,\%}$=14.2, $Q_{H2O,\,46\,mol\,\%}$=7.1). Thus, SOS concentrations were selected to produce membranes with different RTIL compositions under equilibrium swelling, based on the hypothesis that higher RTIL loadings would produce greater $CO_2$ permeability. Unexpectedly, the selected SOS concentrations of about 22 mol % and about 46 mol % produced much smaller differences in RTIL swelling ratios (18.4 vs. 16.5), with mass concentrations of RTIL both reaching or exceeding 94 wt %.

Based on these results, the RTIL was a better solvent for PEO than water, with a much higher swelling capacity regardless of SOS content. Without wishing to be bound by theory, the exceptional compatibility of [EMIM][TFSI] with the PEO matrix may involve coordination of the polyether backbone with the cationic imidazolium, and potential hydrogen bonding of the oxygen species in the PEO backbone with the C(2)-H of the imidazolium heterocycle.

Example 21—Gas Separation Performance Using the Membranes

Figure 33:
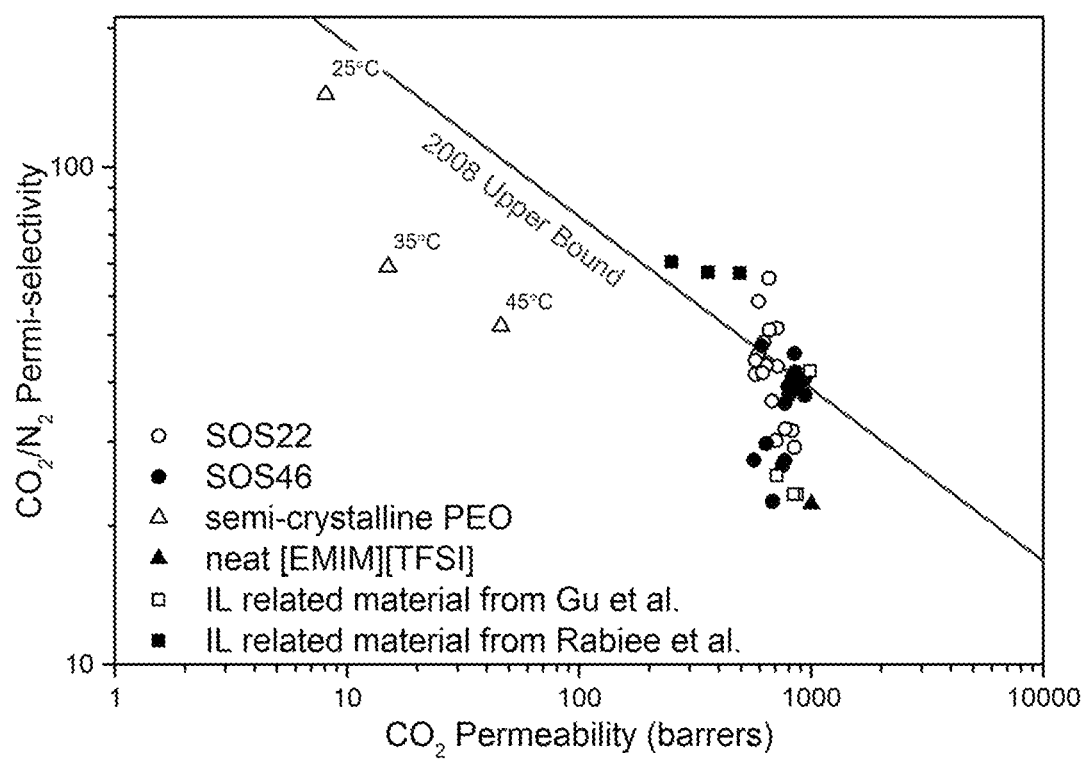
FIG. 33. Robeson plot showing the single-gas $CO_2/N_2$ separation performance of SOS22 and SOS46 saturated with [EMIM][TFSI].

The $CO_2/N_2$ selectivity and $CO_2$ permeation performance of multiple SOS46 and SOS22 membranes (Example 19) were measured and assessed against the 2008 Robeson plot upper bound, as presented in FIG. 33. The measured values represented a total of three different SOS22 and three different SOS46 membranes measured over transmembrane pressures from between about 26 kPa and about 413 kPa, as shown below at Tables 7-12.

TABLE 7

Permeability, diffusivity, and solubility coefficients of $CO_2$ for SOS22/[EMIM][TFSI] membranes.

| Feed Pressure (kPa) | $CO_2$ Permeability (barrers) | $CO_2$ Diffusivity ($10^{-6}$ cm$^2$/s) | $CO_2$ Solubility (cm$^3$ of $CO_2$ at STP) |
|---|---|---|---|
| 37 [1] | 847 | 1.7 | 3.7 |
| 52 [1] | 826 | 1.6 | 3.8 |
| 84 [1] | 774 | 1.4 | 4.1 |
| 112 [1] | 716 | 1.6 | 3.2 |
| 345 [1] | 575 | 1.1 | 3.8 |
| 413 [1] | 589 | 1.2 | 3.6 |
| 27 [2] | 678 | 1.6 | 3.2 |
| 42 [2] | 705 | 1.6 | 3.4 |
| 61 [2] | 640 | 1.6 | 3.0 |
| 76 [2] | 618 | 1.6 | 2.9 |
| 26 [3] | 712 | 1.2 | 4.7 |
| 27 [3] | 659 | 1.2 | 4.3 |
| 52 [3] | 658 | 1.1 | 4.6 |
| 53 [3] | 624 | 1.2 | 4.0 |
| 54 [3] | 573 | 1.1 | 4.0 |
| 85 [3] | 591 | 1.0 | 4.3 |

[1] First membrane tested (280 μm).
[2] Second membrane tested (175 μm).
[3] Third membrane tested (135 μm).

TABLE 8

Permeability of $N_2$ for SOS22/[EMIM][TFSI] membranes.

| Feed Pressure (kPa) | $N_2$ Permeability (barrers) |
|---|---|
| 27 [1] | 31 |
| 55 [1] | 28 |
| 84 [1] | 26 |
| 123 [1] | 18 |
| 385 [1] | 15 |
| 393 [1] | 14 |
| 27 [2] | 20 |
| 42 [2] | 25 |
| 61 [2] | 16 |
| 76 [2] | 16 |
| 29 [3] | 15 |
| 53 [3] | 14 |
| 85 [3] | 11 |

[1] First membrane tested (280 μm).
[2] Second membrane tested (175 μm).
[3] Third membrane tested (135 μm).

TABLE 9

Permeability, diffusivity, and solubility coefficients of $CH_4$ for SOS22/[EMIM][TFSI] membranes having an average thickness of about 280 μm.

| Feed Pressure (kPa) | $CH_4$ Permeability (barrers) | $CO_2$ Diffusivity ($10^{-6}$ cm$^2$/s) | $CH_4$ Solubility (cm$^3$ of $CO_2$ at STP) |
|---|---|---|---|
| 108 | 41 | 0.9 | 0.3 |
| 398 | 33 | 0.4 | 0.6 |
| 391 | 34 | 0.4 | 0.5 |
| 398 | 32 | 0.5 | 0.5 |

TABLE 10

Permeability, diffusivity, and solubility coefficients of $CO_2$ for SOS46/[EMIM][TFSI] membranes.

| Feed Pressure (kPa) | $CO_2$ Permeability (barrers) | $CO_2$ Diffusivity ($10^{-6}$ cm$^2$/s) | $CO_2$ Solubility (cm$^3$ of $CO_2$ at STP) |
|---|---|---|---|
| 28 [1] | 845 | 2.0 | 3.2 |
| 56 [1] | 807 | 1.9 | 3.3 |
| 86 [1] | 770 | 1.7 | 3.4 |
| 118 [1] | 796 | 1.8 | 3.3 |
| 132 [1] | 800 | 1.7 | 3.7 |
| 26 [2] | 940 | 1.7 | 4.1 |
| 57 [2] | 936 | 1.6 | 4.4 |
| 89 [2] | 872 | 1.4 | 4.6 |
| 109 [2] | 853 | 1.7 | 3.9 |
| 154 [2] | 827 | 1.6 | 3.8 |
| 212 [2] | 844 | 1.5 | 4.1 |
| 58 [3] | 771 | N/A | N/A |
| 81 [3] | 754 | N/A | N/A |
| 401 [4] | 612 | 1.5 | 3.1 |
| 404 [4] | 639 | 1.7 | 2.8 |
| 409 [4] | 567 | 1.3 | 3.2 |

[1] First membrane tested (200 μm).
[2] Second membrane tested (185 μm).
[3] Third membrane tested (185 μm).
[4] Fourth membrane tested (430 μm).

TABLE 11

Permeability, diffusivity, and solubility coefficients of $N_2$ for SOS46/[EMIM][TFSI] membranes.

| Feed Pressure (kPa) | $N_2$ Permeability (barrers) |
|---|---|
| 27 [1] | 20 |
| 63 [1] | 23 |
| 88 [1] | 23 |
| 111 [1] | 22 |
| 175 [1] | 23 |
| 27 [2] | 27 |
| 52 [2] | 25 |
| 76 [2] | 24 |
| 104 [2] | 22 |
| 150 [2] | 22 |
| 182 [2] | 22 |
| 27 [3] | 32 |
| 53 [3] | 30 |
| 82 [3] | 30 |
| 112 [4] | 14 |
| 337 [4] | 23 |
| 387 [4] | 22 |

[1] First membrane tested (200 μm).
[2] Second membrane tested (185 μm).
[3] Third membrane tested (185 μm).
[4] Fourth membrane tested (430 μm).

TABLE 12

The measured permeability, diffusivity, and solubility coefficients of $CH_4$ for SOS46/[EMIM][TFSI] membranes.

| Feed Pressure (kPa) | $CH_4$ Permeability (barrers) | $CH_4$ Diffusivity ($10^{-6}$ cm$^2$/s) | $CH_4$ Solubility (cm$^3$ of $CH_4$ at STP) |
|---|---|---|---|
| 85 * | 32 | 1.5 | 0.0 |
| 96 * | 38 | 1.0 | 2.7 |
| 405 * | 52 | 2.2 | 0.2 |
| 480 * | 50 | 1.2 | 0.0 |

* Membrane thickness (430 μm).

FIG. 33 is Robeson plot showing the single-gas $CO_2/N_2$ separation performance of SOS22 and SOS46 saturated with [EMIM][TFSI]. SOS data were collected at 22-24° C. and at transmembrane pressures between about 26 kPa and about 413 kPa. Also included were separation performance data from similar RTIL-block copolymer membrane materials produced at ambient temperature, transmembrane pressure of 202 kPa and at 25° C. and transmembrane pressure of 400 kPa, neat [EMIM][TFSI] at 25° C., and semi-crystalline PEO (at 790 kPa and 25, 35 and 45° C.). FIG. 33 represented only composite values for which both the $CO_2/N_2$ permselectivity and the $CO_2$ permeability were recorded at matched transmembrane pressures (within 5%). Additional $CO_2$ permeability data collected during a 28-day membrane longevity experiment shown below at Table 12.

TABLE 12

The measured permeability, diffusivity, and solubility coefficients of $CO_2$ for an SOS46/[EMIM][TFSI] membrane over 28 days at a feed pressure of approximately 230 kPa, having an average membrane thickness of about 255 μm.

| Day | $CO_2$ Permeability (barrers) | $CO_2$ Diffusivity ($10^{-6}$ cm$^2$/s) | $CO_2$ Solubility (cm$^3$ of $CO_2$ at STP) |
|---|---|---|---|
| 1 | 889 | 1.6 | 4.3 |
| 3 | 854 | 2.5 | 2.6 |
| 3 | 845 | 2.5 | 2.6 |
| 4 | 942 | 2.8 | 2.6 |
| 6 | 938 | 2.9 | 2.5 |
| 8 | 989 | 3.1 | 2.4 |
| 8 | 980 | 1.6 | 3.0 |
| 8 | 970 | 2.7 | 2.7 |
| 21 | 957 | 3.0 | 2.5 |
| 21 | 975 | 2.9 | 2.6 |
| 22 | 977 | 2.9 | 2.5 |
| 23 | 972 | 2.9 | 2.5 |
| 24 | 955 | 3.1 | 2.4 |
| 25 | 955 | 2.4 | 3.0 |
| 26 | 996 | 3.2 | 2.4 |
| 28 | 971 | 2.8 | 2.6 |

Both SOS22 and SOS46 membranes performed similarly, producing measured $CO_2$ permeabilities from between about 567 barrers and about 996 barrers. The $CO_2/N_2$ selectivities ranged between about 21.3 and about 59.8. These values varied considerably between membrane samples and appeared uncorrelated to feed pressure. The measured values traversed the 2008 Robeson plot upper bound and was on par with similar style membranes, which also significantly increased in $CO_2/N_2$ selectivity while experiencing relatively small losses in $CO_2$ permeability. The highly elastic and yet distensible nature of these membranes at such high loadings differentiates them from this group. The elasticity and intrinsic ability to accommodate tensile loading without plastic deformation gave these membranes an inherent ability to withstand transmembrane pressures over significant time durations.

The origin of measurement-to-measurement and membrane-to-membrane differences in performance produced within the same SOS blend types remains under investigation. Variations in film thickness uniformity, surface morphology, stress states across the membrane surface, and uncertainties of gas permeability measurements (sample mounting, leak rates, etc.) were likely contributors. Correlations between performance and these specific film characteristics remained unaddressed. The data represented that no discernible trend in separation was observed from a range of measured membrane thicknesses (135 μm to 430 μm).

The RTIL-hydrogel membranes displayed $CO_2/N_2$ selectivities higher than neat [EMIM][TFSI]. The nanostructure of block copolymers has significantly affected light-gas permeation and selectivity properties. The glassy polystyrene domains (comprising only about 0.5 wt % of the membrane mass) may be responsible. Without wishing to be bound by any particular theory, confinement of ionic liquids inside the nanostructure of porous materials may significantly affect $CO_2$ diffusivity and solubility properties. The local environment may disrupt the bulk RTIL liquid structure, thereby producing increased free volume and differences in RTIL mobility. The active matrix in SOS membranes comprised dense high molecular weight PEO brushes saturated with RTIL solvent. The local interaction between the PEO chains and the RTIL (a good solvent for PEO) may have decreased resistance to $CO_2$ transport. Likewise, the interaction between quadripolar $CO_2$ and the PEO chains themselves may have influenced the increase.

FIG. 33 included the combined $CO_2$ permselectivities and permeabilities of semi-crystalline PEO at 790 kPa and three temperatures (25° C., 35° C., and 45° C.) compared to neat [EMIM][TFSI] and the SOS membranes. PEO has exceptional $CO_2/N_2$ selectivity at ambient temperature. At temperatures closer to the PEO melt temperature (65° C.), permeability improved moderately, presumably as the amorphous chains (not involved in crystalline lamellae) gained mobility. The "doping" of the [EMIM][TFSI] with the PEO chains of the block copolymer was consistent with the improved selectivity measured in the SOS membranes.

Example 22—Mechanical Performance of the Membranes

Figure 28:
FIG. 28. SO/SOS RTIL composite membranes containing ca. 95 wt % 1-ethyl-3-methylimidazolium bis(trifluoromethanesulfonyl)imide ([EMIM][TFSI]) (left). The membranes were highly elastic, with an ability to accommodate strains to nearly 300% without plastic deformation (right).
Figure 29:
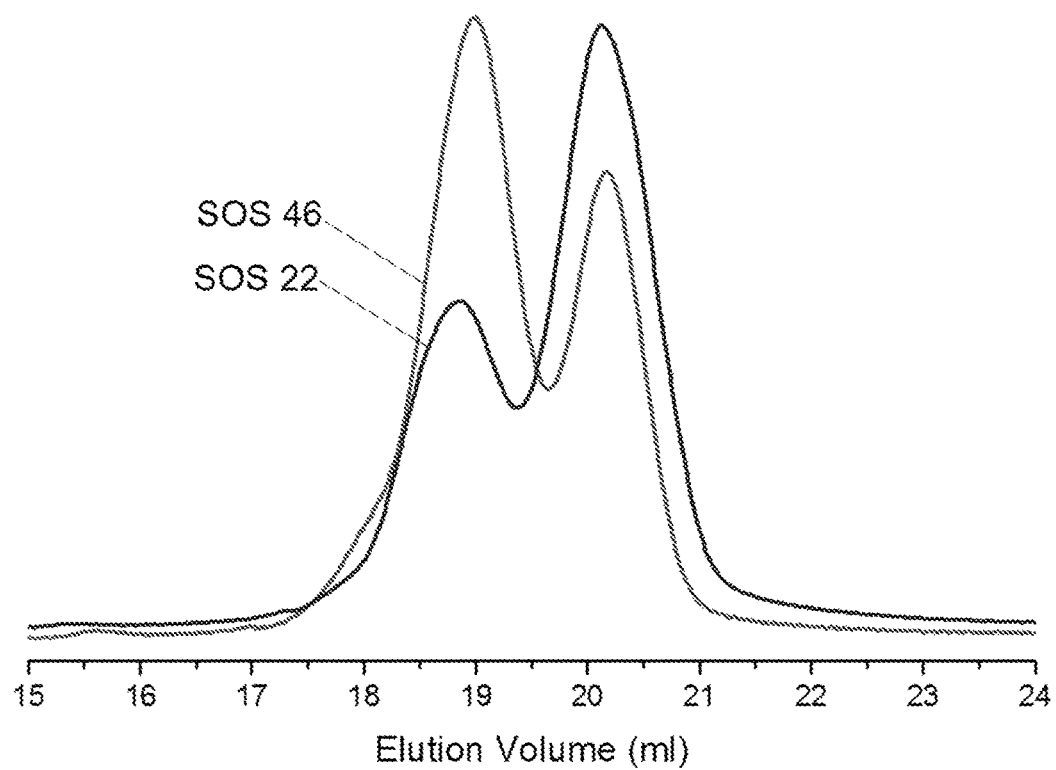
FIG. 29. Size-exclusion chromatography (SEC) chromatograms of dry polymer blends SOS22 and SOS46. Left and right peak positions corresponded to the elution of SOS triblock and SO diblock copolymer in each blend, respectively.

The elastic RTIL composite membranes of Example 19 starkly contrasted to the many solid, gel-like, and liquid phase RTIL-containing membrane. Such elasticity was demonstrated qualitatively in simple stretching experiments (see FIG. 28). The free-standing membrane placed upon a porous support must withstand the normal compressive force of the transmembrane pressure differential and a significant tensile force, generated by a Laplace pressure, where the membrane spans the pore openings of the support, like a diaphragm.

Figure 34A:
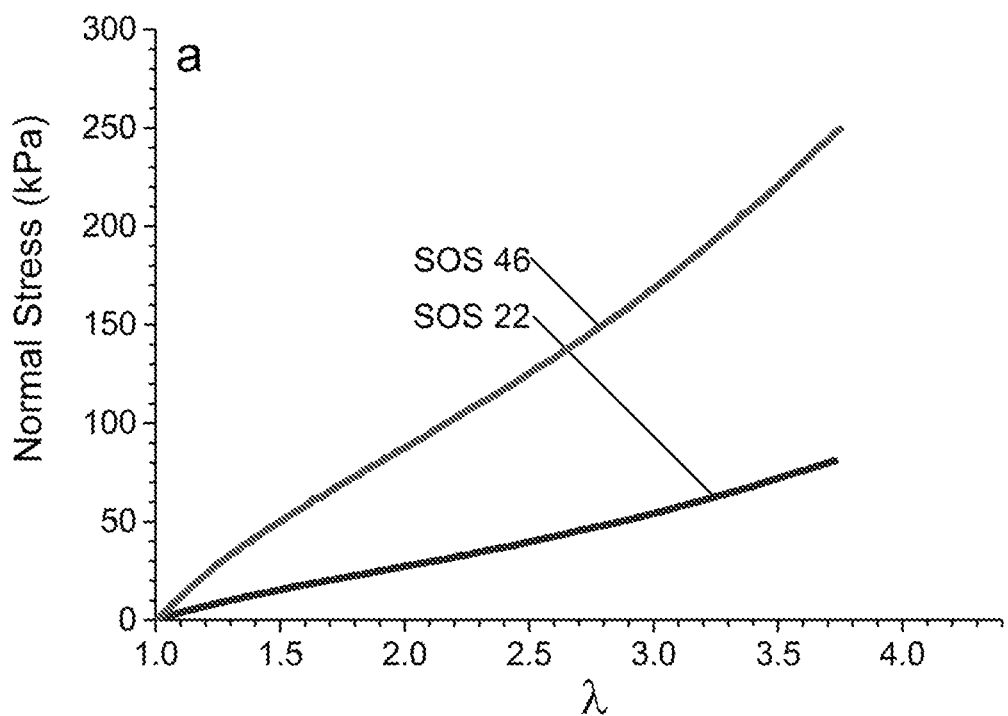
FIG. 34A Stress-strain behavior of under uniaxial tension applied with a strain rate of 2% $s^{-1}$.

To evaluate the mechanical performance of the SO/SOS RTIL composite membranes, the stress-strain behavior under both uniaxial tension and unconfined compression was evaluated (FIG. 34). FIG. 34A showed representative stress-strain data from typical tensile loading experiment in which the samples were pulled at 10% $s^{-1}$ to failure. The normal engineering stress (kPa) was plotted against the extension ratio ($\lambda$=ratio of the length under tension to the original sample length). Both RTIL loaded samples of SOS46 and SOS22 failed at a $\lambda$ value of approximately 3.8 (a strain of nearly 300%). The ultimate tensile strength (UTS), defined as the highest normal stress before failure, was just greater than three times higher for SOS46 than for SOS22 (250 kPa and 80 kPa, respectively), underscoring the importance of triblock copolymer concentration in dictating the mechanical response of the swollen composite.

Figure 34B:
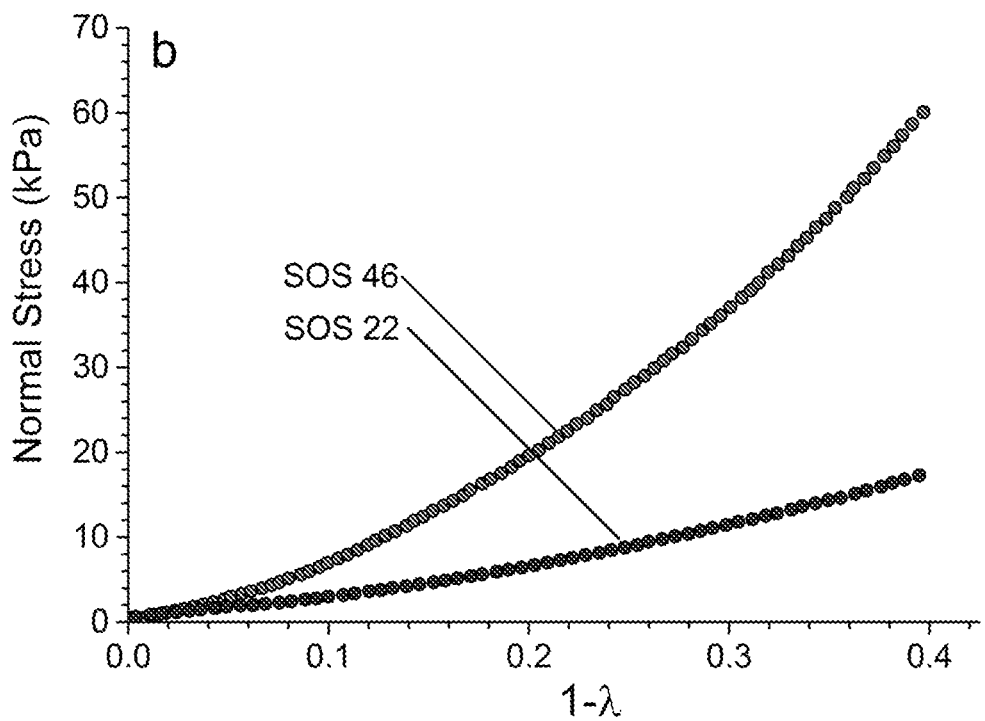
FIG. 34B Stress-strain behavior under unconfined compression applied at a strain rate=10% $s^{-1}$.

Similar differences in behavior were observed when subjected to unconfined compression. Using a strain rate of 10% $s^{-1}$, unconfined compression was performed to 40% strain (FIG. 34B). Beyond 40% strain, the RTIL composite samples rapid increased in compressive stress beyond transducer capabilities. The compressive modulus of the RTIL swollen SOS46 up to 40% strain was about five times higher than that of SOS22 (348 kPa vs. 71 kPa, respectively).

The mechanical property dependence on triblock copolymer composition found in the RTIL-swollen composites mimics that found in similarly designed hydrogel systems, where the UTS and compressive modulus also increased with increasing triblock content. Tuning the mechanical properties of the composite membrane through simple shifts in SOS content provided a facile and convenient strategy for changing the mechanical behavior in these systems. The 24 mol % increase in SOS (from 22 mol % to 46 mol %) resulted in a three- to four-fold increase in mechanical strength. The latter related to the high PEO solubility in [EMIM][TFSI], which produced quire similar $CO_2$ gas permeability and separation properties in SOS46 and SOS22 membranes. The triblock copolymer content may be increased in these membranes without significant loss in $CO_2/N_2$ separation performance.

Figure 35A:
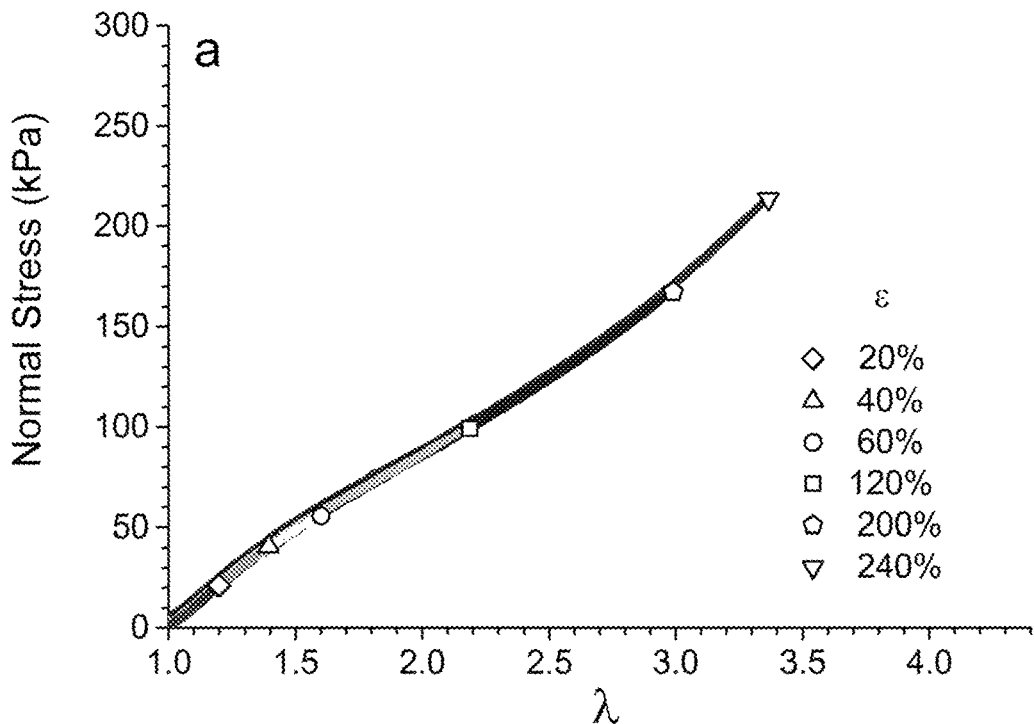
FIG. 35A. Cyclic tensile loading performed on a single sample of RTIL swollen on SOS46 membrane at 20° C. Tensile loading was cycled through progressively increasing strains. Loading and unloading were performed with a strain rate of 2% $s^{-1}$.

The tethered-sphere nanostructure withstood significant transmembrane pressure differentials. The distensibility as a biphasic elastomer composite was reversible, without undergoing plastic deformation under a sustained or changing load. FIG. 35A showed a progressive tensile loading experiment in which a single coupon of the membrane loaded and unload to progressively higher strains. Using a strain rate of 2% $s^{-1}$ (FIG. 35A), the modulus of the swollen RTIL composites did not degrade with each additional cycle and exhibited no detectable hysteresis during the release of the tensile force. First, the tethered-sphere network absorbed the stress elastically and reversibly without breaking bonds or disrupting the network structure over a significant range of stresses. The network absorbed stress through relaxation of dynamic chain entanglements in the diblock copolymer population, in combination with traditional mechanisms of energy dissipation associated with chain stretching and chain slip in the tethering triblock copolymer population. The connectivity among the individual spheres, which is highly redundant at 46 mol % triblock copolymer, produced a mechanical connectivity that was extremely efficient at distributing stress across the sample. Second, the lack of significant hysteresis upon the release of the tensile force confirmed that strain produced RTIL movement internal to the membrane only, with no detectable RTIL leakage under load conditions. The elastic restoring force in the tethered-sphere network was such that RTIL redistribution was promoted at a rate slower than 2% $s^{-1}$. No other membranes based on BCP and RTILs have these unique material properties.

Figure 35B:
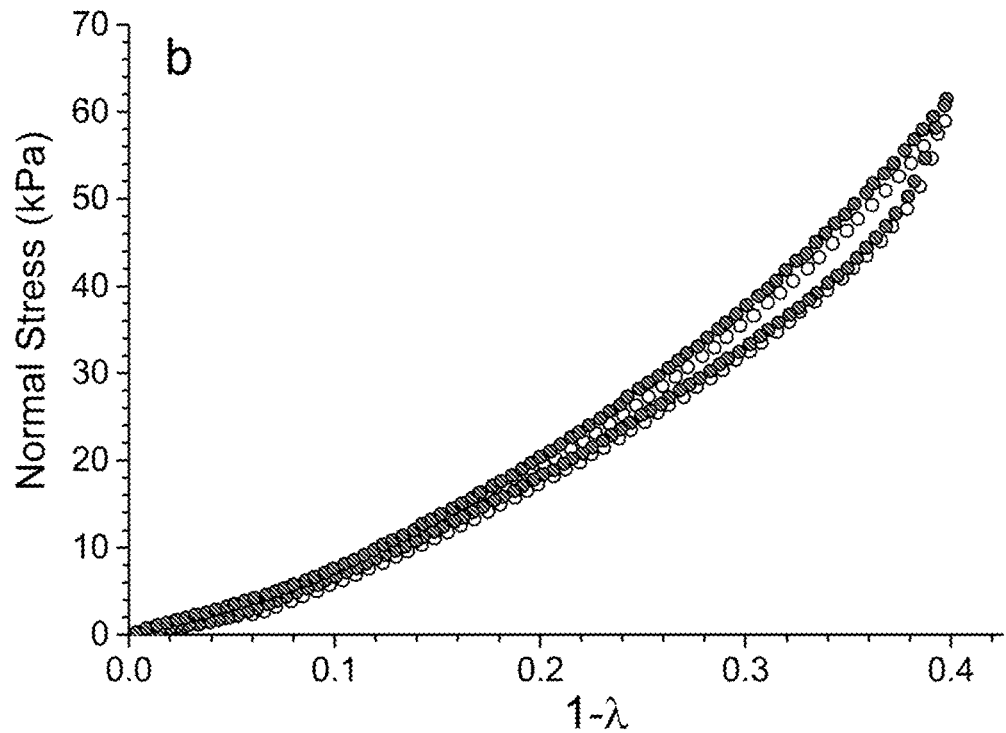
FIG. 35B Unconfined compression-decompression cycles performed on a single sample of RTIL swollen SOS46 membrane at 20° C.

Cyclic loading under unconfined compression confirmed the elastic reversibility of the membranes. Ten unconfined compression-decompression cycles at a constant strain rate of 10% $s^{-1}$ (FIG. 35B) were also performed on the swollen SOS46 samples. The first and eleventh cycles agreed, showing no property degradation during mechanical loading and unloading. Intra-cycle hysteresis was observed during the release of the compressive load. Coincidence with the compression data was eventually achieved before reaching zero applied force, implying fast redistribution of RTIL molecules. This behavior confirmed that hysteresis observed under cyclic compression was related to the differences between the strain rate and the RTIL mass-transfer rates in the membrane. Full recovery and excellent reproducibility of successive cycles indicated that very little, if any, liquid was exuded from the membrane under compressive strains up to 40%.

Figure 36A:
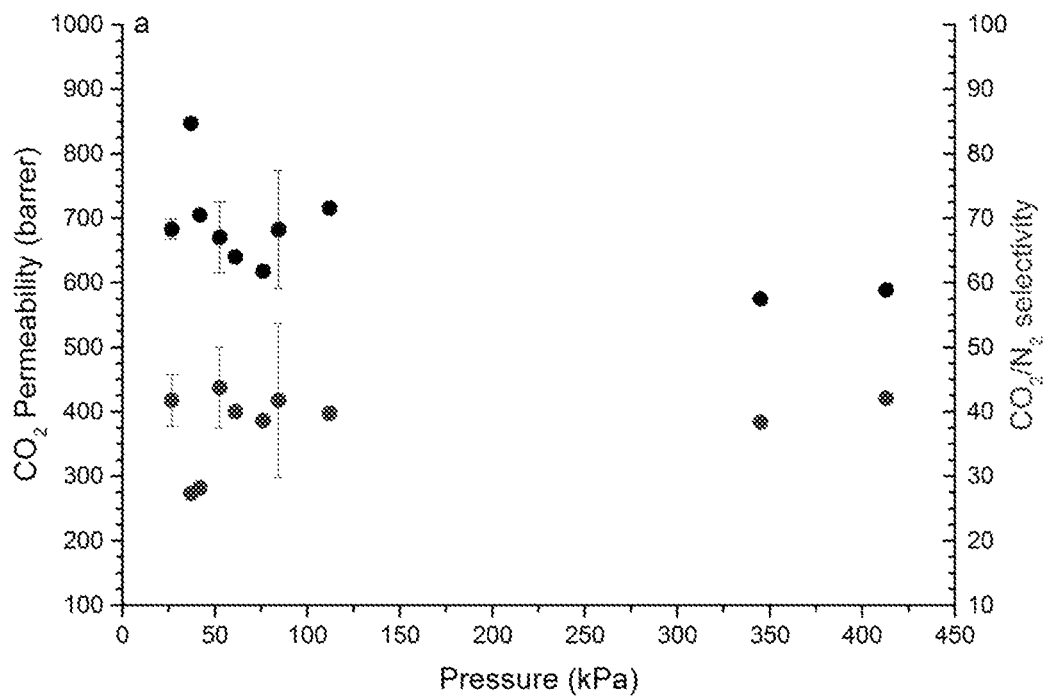
FIG. 36. Single-gas $CO_2/N_2$ permselectivity data as a function of increasing feed pressure for the RTIL composite membranes fabricated from SOS22 (FIG. 36A) and SOS46 (FIG. 36B). All data were collected at 23° C. When multiple membranes were tested, mean values and standard errors were indicated.
Figure 36B:
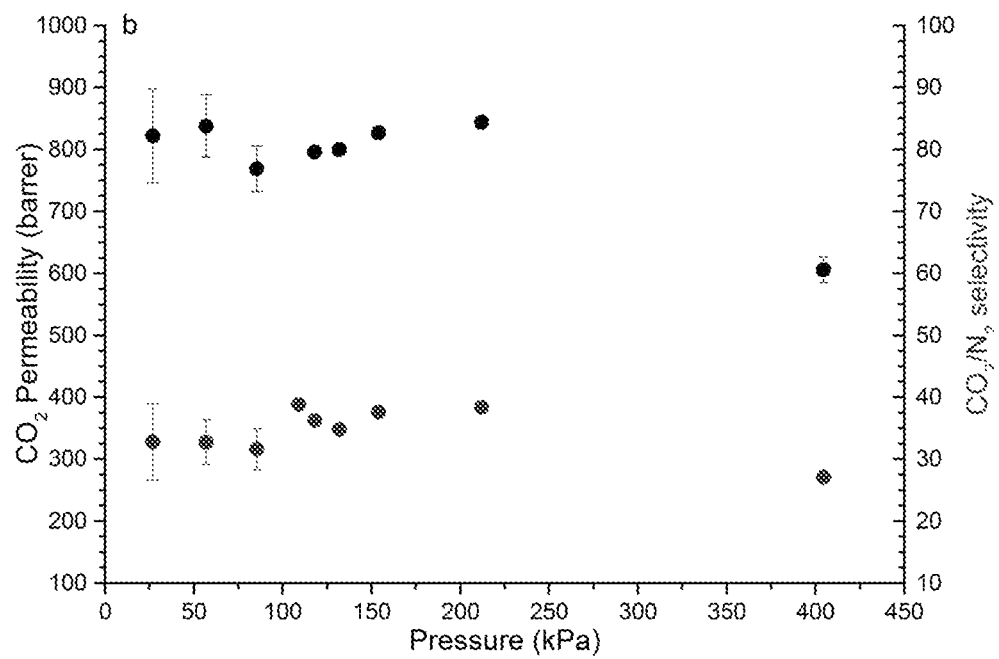

Example 23—Effect of Transmembrane Pressure on $CO_2/N_2$ Separation Performance Industrial processes for separating light gases can operate over a wide range of pressure differentials. As shown in FIG. 36, $CO_2/N_2$ selectivity and $CO_2$ permeability were measured by increasing transmembrane pressure differentials, including pressures just above 400 kPa in both the SOS22 and SOS46 systems (Example 19). Data were collected at a given pressure differential using multiple membranes and presented as mean values with calculated standard deviations. For the membranes of a given triblock copolymer blend ratio, the effect of increasing transmembrane pressure on $CO_2/N_2$ separation performance was minor over the range of pressures examined. For the SOS46 membrane run just above 400 kPa, a slight decline in both $CO_2$ permeability and $CO_2/N_2$ selectivity was observed. The thickness of this membrane was 430 µm, which was about twice the thickness of the other three SOS46 membranes.

The SOS22 membranes exhibited a slightly higher average $CO_2/N_2$ selectivity compared to the SOS46 composites. The $CO_2$ permeability exhibited the inverse trend. While the inverse relationship itself, consistent with the Robeson flux-selectivity tradeoff was not unexpected, that the membrane system containing the higher RTIL content (SOS22) should exhibit the lower permeability (but the higher selectivity) is not obvious. The role of RTIL mobility and liquid structure as a function of the PEO chain concentration throughout active layer may be important o determining ultimate gas separation performance.

FIG. 36 shows the single-gas $CO_2/N_2$ permselectivity data as a function of increasing feed pressure for the RTIL composite membranes fabricated from SOS22 (top) and SOS46 (bottom). All data were collected at 23° C. When multiple membranes were tested, mean values and standard errors are indicated.

Example 24—Performance Longevity of the Hydrogel Membranes

Figure 37:
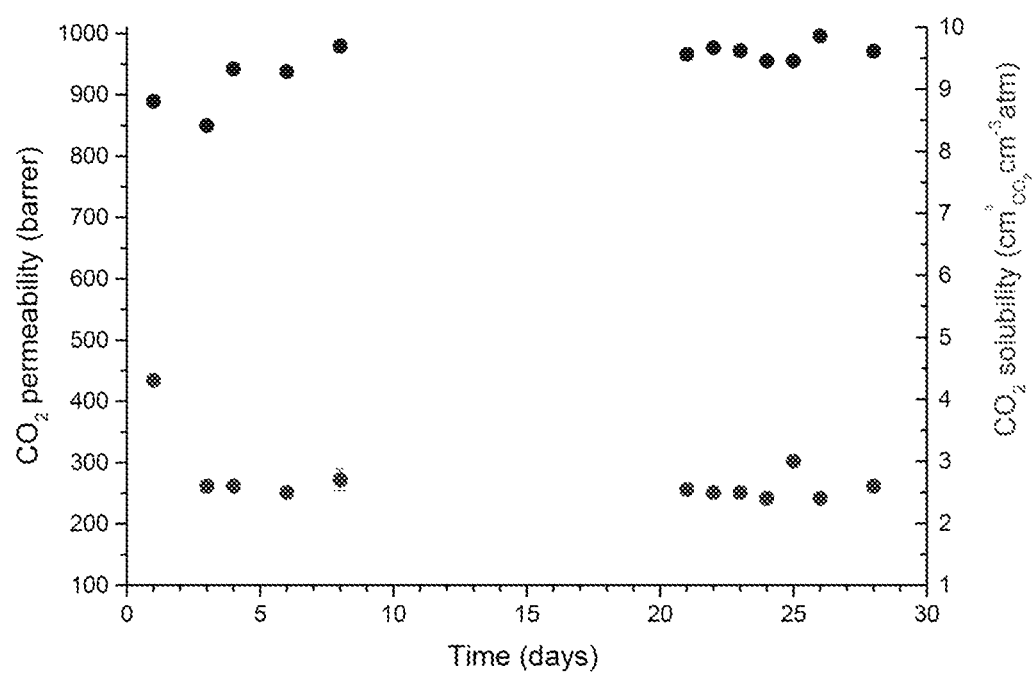
FIG. 37. The $CO_2$ permeability and $CO_2$ solubility over a 28-day time period for a SOS46 membrane saturated with [EMIM][TFSI].

To examine the potential long-term stability of the SO/SOS RTIL composite membranes under gas separation conditions, a single SOS46 membrane was saturated with [EMIM][TFSI] and measured for $CO_2$ permeation 16 times over 28 days (FIG. 37). Between tests the membrane was kept under dynamic vacuum. All tests were performed with a $CO_2$ feed pressure of about 230 kPa. Initially, variations in $CO_2$ permeability of about 50 barrers were observed. Between days 8 and 28 the $CO_2$ permeability of this membrane stabilized, giving consistent readings of $9.7\pm0.1\times10^2$ barrers, showing that membranes of the SO/SOS based RTIL composite membranes maintained their permeation performance over a reasonable timescale while sustaining cycled transmembrane pressures between applied vacuum and 230 kPa. They did not leak physically entrained RTIL over the 28 days. The PS core domains remained glassy, confirming that exposure to the RTIL solvating the PEO chains, or that the dissolved $CO_2$ during measurement did not negatively impact the mechanical integrity of these membranes through plasticization. Water in the feed gas did not adversely affect the system's mechanical properties.

Example 25—Hydrogels Having a Combination of RTIL and an Aqueous Medium

Figure 38:
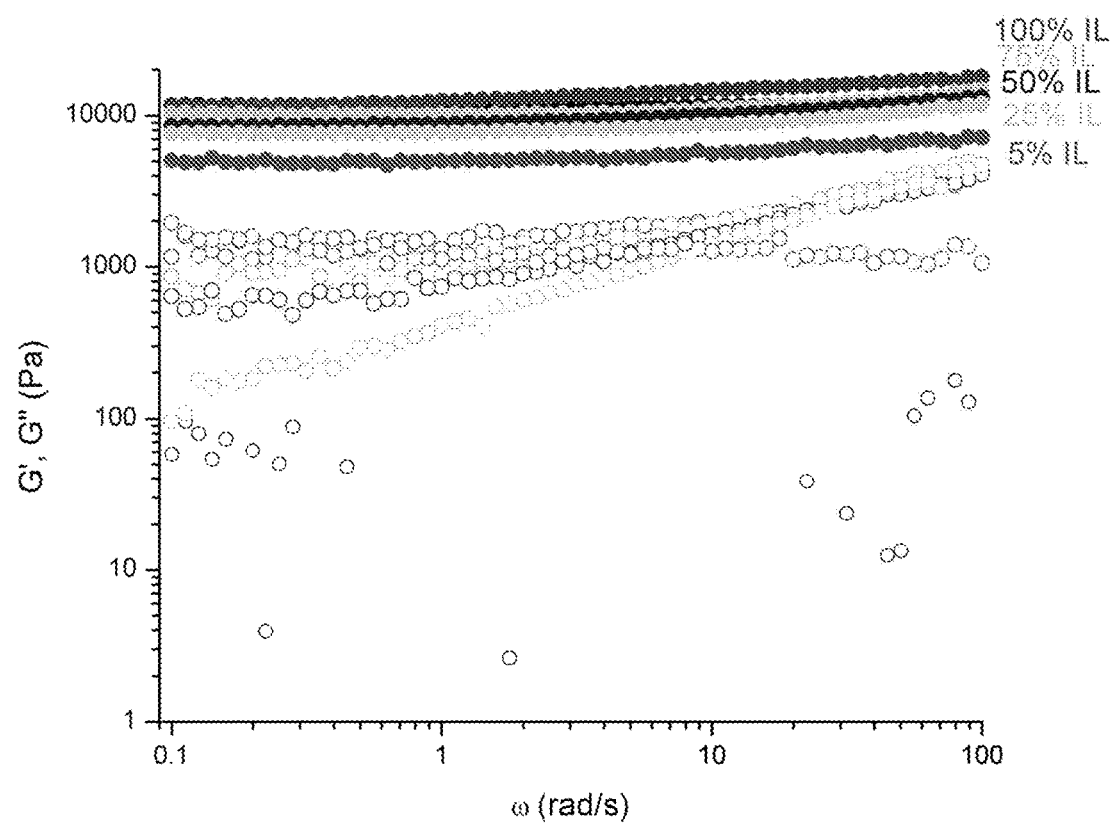
FIG. 38. The stress strain data obtained from rheological frequency sweeps for hydrogels formed from SOS20 swollen in liquid media comprising mixtures of [(dhp)mIm][dca]/water.
Figure 39:
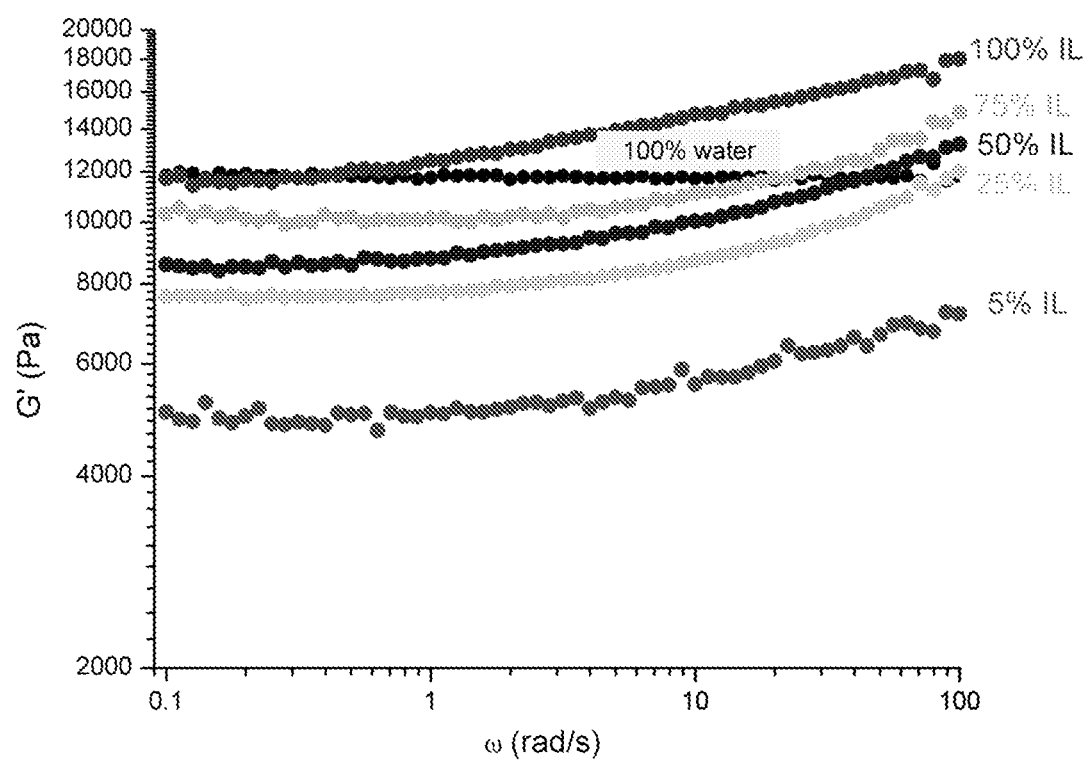
FIG. 39. The stress strain data obtained from rheological frequency sweeps for hydrogel formed SOS20 swollen in liquid media comprising mixtures of [(dhp)mIm][dca]/water, as in FIG. 38 but with the isolated elastic modulus data.

Hydrogels were formed from mixtures of the RTIL 1-(2,3-dihydroxypropyl)-alkyl imidazolium dicyanamide [(dhp)mIm][dca] and water by swelling 80:20 SO/SOS (SOS20, Example 19), produced as described herein. FIG. 38 shows the stress strain data for SOS20 swollen in aqueous mixtures of [(dhp)mIm][dca]/water, including 100% water, 5:95 (vol/vol) ionic liquid/water, 25:75 (vol/vol) ionic liquid/water, 50:50 (vol/vol) ionic liquid/water, 75:25 (vol/vol) ionic liquid/water, and 100% ionic liquid. FIG. 38 shows the rheological frequency sweeps for SOS20 swollen in the aqueous mixtures of [(dhp)mIm][dca]/water. FIG. 39 shows the same rheological frequency sweeps as in FIG. 38 but with only the elastic modulus data. As can be seen from these data, mechanically stable, thermoplastic hydrogels were formed using a liquid medium comprising a mixture of the RTIL and aqueous medium.

Example 26—Hydrogel Recovery after Extreme Compression

Figure 40:
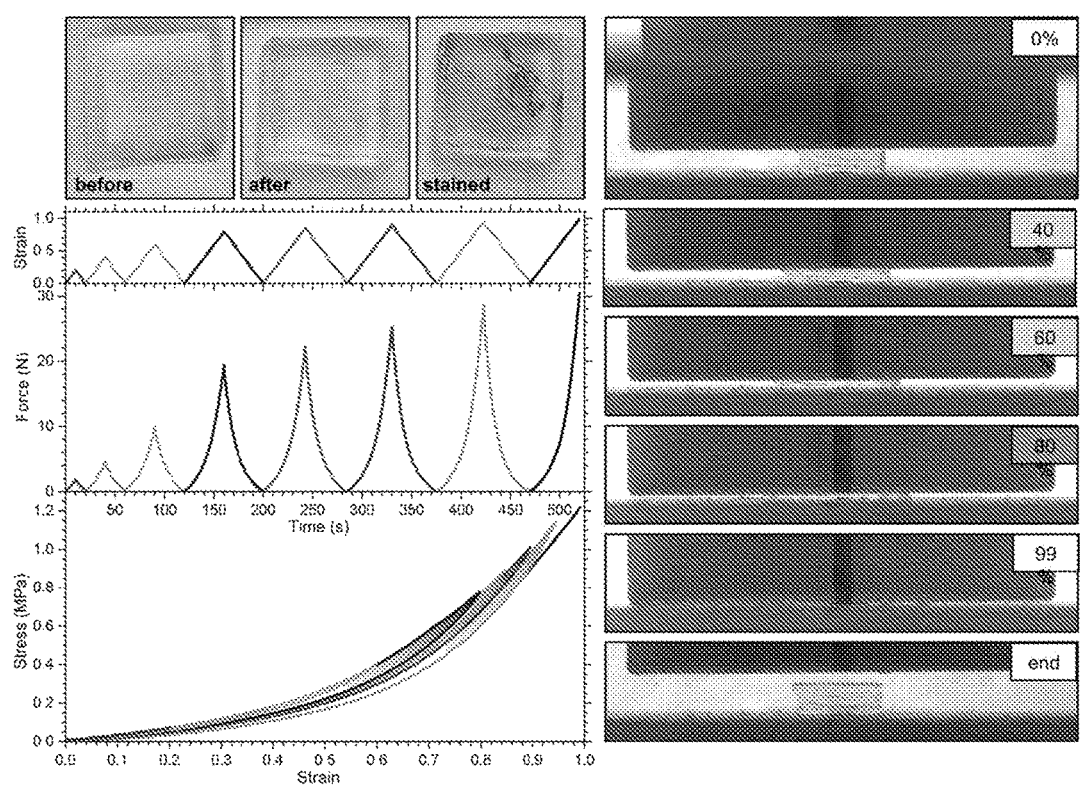
FIG. 40. Example of an SO/SOS hydrogel composed of 61 mol % SOS swollen with phosphate buffered saline (PBS) and subjected to unconfined compression at a rate of 2% strain/s to about 20% strain, and then a return to 0% strain at the same rate. Successive cycles increased the final strain to about 40%, about 60%, about 80%, about 90%, about 95%, and about 99% strain. The images above and to the right show that the square sample (5 mm×5 mm) remained intact, without catastrophic failure typical of most hydrogel systems.

An SO/SOS hydrogel composed of 61 mol % SOS swollen with phosphate buffered saline (PBS) was subjected to progressively higher loadings under unconfined compression, as shown at FIG. 40. The first cycle consisted of compression at a rate of 2% strain/s to about 20% strain, and then a return to 0% strain at the same rate. Successive cycles increased the final strain to about 40%, about 60%, about 80%, about 90%, about 95%, and about 99% strain. As shown in the images above and to the right in FIG. 40, the square sample (5 mm×5 mm) remained intact, without catastrophic failure typical of most hydrogel systems. Additionally, cycles confirmed no cycle-to-cycle hysteresis to 60% strain, and minimal cycle-to-cycle hysteresis at strains above 60%.

The origin of the hysteresis in this sample was small crack formation at about 70% strain. Crack propagation appears to be suppressed such that additional damage is limited at higher strains. As the stained image shows, fracture appears to have occurred at an isolated location in the hydrogel, and remained localized to the original fracture location. The absence of microcracks at other locations in the hydrogel suggested that fracture was initiated at a localized defect and was not a product of material limitations in the absence of such stress concentrations.

This experiment was performed on a square sample, for which significant in-plane stresses in the non-radial directions were produced, and which may be the impetus for the original crack initiation event. It is believed that the square sample fractured because of the lateral shear stresses the sample feels to due to the asymmetry in its shape. In a similar compression experiment using a circular sample, two successive cycles to 99% progressed with no damage and perfectly overlapping stress strain behavior.

Figure 43:
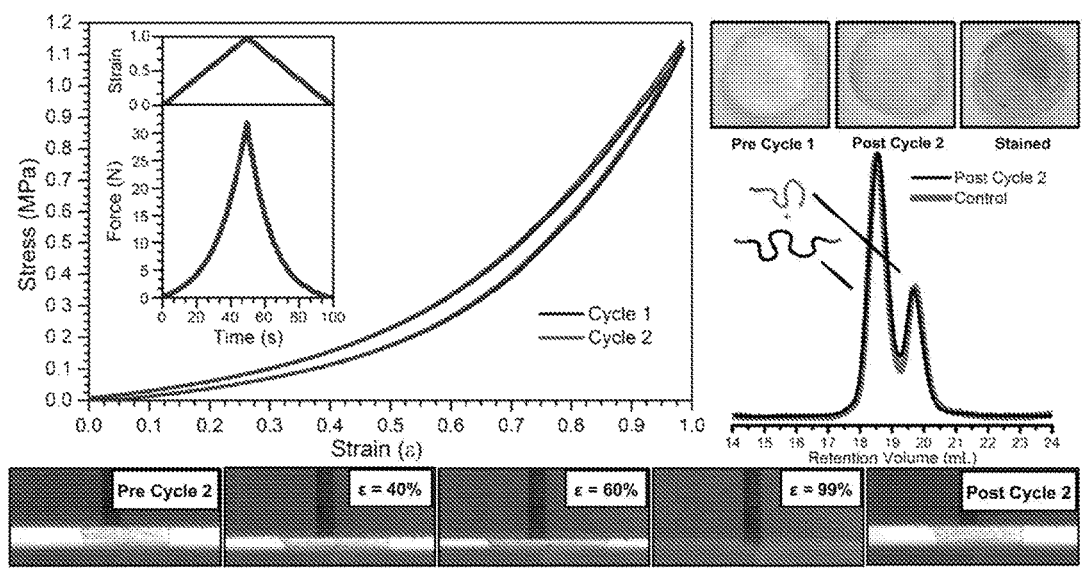
FIG. 43. Overlay of the stress versus strain data from two successive compression cycles to 99% strain (strain rate=2% $s^{-1}$) for a hydrogel (6 mm×1.6 mm, 85 wt % phosphate buffered saline (PBS)) containing 61 mol % SOS triblock copolymer submerged in a phosphate-buffered saline (PBS) bath during testing.

FIG. 43 shows the overlay of the stress versus strain data from two successive compression cycles to 99% strain (strain rate=2% s$^{-1}$) for a hydrogel (6 mm×1.6 mm, 85 wt % phosphate-buffered saline (PBS))) containing 61 mol % SOS triblock copolymer, submerged in a phosphate-buffered saline (PBS) bath. SEC data confirmed no change in molecular weight distribution in the constituent block copolymers comprising the hydrogel following consecutive compression cycles. Staining with India ink confirmed the lack of visible crack formation. Video stills (bottom of the figure) depicted the progression of the second compression cycle.

Regardless, the hydrogel averted catastrophic failure through suppression of crack propagation because of the structure's ability to intrinsically redistribute stress. The hydrogel can be compressed to 99% strain (1/100th of its original thickness) without failure. Most hydrogels fracture catastrophically at compressions much less than 80%.

It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

What is claimed is:

1. A block copolymer hydrogel, comprising:
a glass formed from a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and
a liquid medium at a concentration between about 32:1 and about 2:1 liquid medium/SO—SOS by weight, the liquid medium comprising at least one room-temperature ionic liquid (RTIL);
the block copolymer hydrogel having a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

2. The hydrogel of claim 1, wherein the molar ratio is between about 80:20 and about 20:80 SO/SOS.

3. The hydrogel of claim 1, wherein the polystyrene is a partially or fully hydrogenated polystyrene.

4. The hydrogel of claim 1, wherein the SO—SOS dry blend is heated to a temperature between about 100° C. and about 180° C., under a pressure between about 50 psig and about 800 psig, and for between about 5 minutes and about 50 minutes.

5. The hydrogel of claim 1, wherein the liquid medium concentration is between about 16:1 and about 4:1 liquid medium/SO—SOS by weight.

6. The hydrogel of claim 1, wherein the fatigue resistance is characterized by a modulus recoverable to at least 92% of its value before the compression cycles were run.

7. The hydrogel of claim 1, wherein the at least one room-temperature ionic liquid comprises 1-ethyl-3-methyl-imidazolium bis(trifluoromethanesulfonyl)imide.

8. A glass comprising: glassy domains having a glass transition temperature of at least 60° C.; and crystalline domains, wherein the glass is formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS, wherein the polystyrene is a partially or a fully hydrogenated polystyrene.

9. The glass of claim 8, wherein the molar ratio is between about 80:20 and about 20:80 SO/SOS.

10. The glass of claim 8 formed from heating the SO—SOS dry blend to a temperature between about 100° C. and about 180° C., under a pressure between about 50 psig and about 800 psig, and for between about 5 minutes and about 50 minutes.

11. A membrane, comprising a block copolymer hydrogel of claim 1, the membrane having a $CO_2/N_2$ selectivities between about 20:1 and about 60:1.

12. A battery separator, comprising a block copolymer hydrogel of claim 1, the battery separator increasing effective resistance of an electrolyte by a factor of less than about 4.

13. The battery separator of claim 12, have a porosity of at least about 80%.

14. A method for preparing a block copolymer hydrogel, comprising:
contacting polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS to form an SO—SOS dry blend;
heating the SO—SOS dry blend to form an SO—SOS melt;
allowing the SO—SOS melt to attain ambient temperature to form an SO—SOS glass; and
contacting the SO—SOS glass with a liquid medium to form a block copolymer hydrogel, wherein the liquid medium comprises at least one room-temperature ionic liquid (RTIL),
the block copolymer hydrogel having a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

15. The method of claim 14, wherein the SO—SOS dry blend is formed by dissolving the SO and SOS in an organic solvent and removing the organic solvent.

16. The method of claim 14, wherein the molar ratio is between about 80:20 and about 20:80 SO/SOS.

17. The method of claim 14, wherein the SO—SOS dry blend is heated to a temperature between about 100° C. and about 180° C., under a pressure between about 50 psig and about 800 psig, and for between about 5 minutes and about 50 minutes.

18. The method of claim 14, wherein the liquid medium concentration is between about 16:1 and about 4:1 liquid medium/SO—SOS by weight.

19. The method of claim 14, wherein the fatigue resistance is characterized by a modulus recoverable to at least 92% of its value before the compression cycles were run.

20. The method of claim 10, wherein the at least one room-temperature ionic liquid is selected from the group consisting of 1-ethyl-3-methyl imidazolium bis(trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis(trifluoromethane)sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([($C_{11}$OH)MIM][TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM][BF4]), 1-(2,3-dihydroxypropyl)-3-alkyl imidazolium bis(trifluoromethane)sulfonimide ([(dhp)MIM][TFSI]), 1-(2,3-dihydroxypropyl)-3-alkyl imidazolium hexafluorophosphate ([(dhp)MIM][PF6]), and combinations thereof.

21. The method of claim 20, wherein the at least one room-temperature ionic liquid comprises 1-ethyl-3-methyl-imidazolium bis(trifluoromethanesulfonyl)imide.

22. The method of claim 14, further comprising hydrogenating the polystyrene.

23. The hydrogel of claim 1, wherein chain ends of the SO are functionalized with azide and alkyne groups.

24. The method of claim 14, wherein chain ends of the SO are functionalized with azide and alkyne groups, and wherein the method further comprises coupling the SO chain ends in the liquid medium to modify the SO/SOS molar ratio.

25. The hydrogel of claim 1, wherein the at least one room-temperature ionic liquid is selected from the group consisting of 1-ethyl-3-methyl imidazolium bis(trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis(trifluoromethane)sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([($C_{11}$OH)MIM][TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM][BF4]), 1-(2,3-dihydroxypropyl)-3-alkyl imidazolium bis(trifluoromethane)sulfonimide ([(dhp)MIM][TFSI]), 1-(2,3-dihydroxypropyl)-3-alkyl imidazolium hexafluorophosphate ([(dhp)MIM][PF6]), and combinations thereof.

26. A block copolymer hydrogel, comprising:
a glass formed from a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and
a liquid medium at a concentration between about 32:1 and about 2:1 liquid medium/SO—SOS by weight, the liquid medium comprising at least one buffer;
the block copolymer hydrogel having a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

27. The hydrogel of claim 26, wherein the at least one buffer is selected from the group consisting of phosphate-buffered saline (PBS) and Ringer's solution.

28. The hydrogel of claim 27, wherein the at least one buffer is phosphate-buffered saline (PBS).

29. The hydrogel of claim 28, wherein the molar ratio is between about 80:20 and about 20:80 SO/SOS.

30. The hydrogel of claim 28, wherein the polystyrene is a partially or fully hydrogenated polystyrene.

31. The hydrogel of claim 28, wherein the SO—SOS dry blend is heated to a temperature between about 100° C. and about 180° C., under a pressure between about 50 psig and about 800 psig, and for between about 5 minutes and about 50 minutes.

32. The hydrogel of claim 28, wherein the liquid medium concentration is between about 16:1 and about 4:1 liquid medium/SO—SOS by weight.

33. The hydrogel of claim 28, wherein the fatigue resistance is characterized by a modulus recoverable to at least 92% of its value before the compression cycles were run.

34. The hydrogel of claim 28, wherein chain ends of the SO are functionalized with azide and alkyne groups.

35. A method for preparing a block copolymer hydrogel, comprising:
contacting polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS to form an SO—SOS dry blend;
heating the SO—SOS dry blend to form an SO—SOS melt;
allowing the SO—SOS melt to attain ambient temperature to form an SO—SOS glass; and
contacting the SO—SOS glass with a liquid medium to form a block copolymer hydrogel, wherein the liquid medium comprises at least one buffer,
the block copolymer hydrogel having a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

36. The method of claim 35, wherein the at least one buffer is selected from the group consisting of phosphate-buffered saline (PBS) and Ringer's solution.

37. The method of claim 36, wherein the at least one buffer is phosphate-buffered saline (PBS).

38. The method of claim 37, wherein the SO—SOS dry blend is formed by dissolving the SO and SOS in an organic solvent and removing the organic solvent.

39. The method of claim 37, wherein the molar ratio is between about 80:20 and about 20:80 SO/SOS.

40. The method of claim 37, wherein the SO—SOS dry blend is heated to a temperature between about 100° C. and about 180° C., under a pressure between about 50 psig and about 800 psig, and for between about 5 minutes and about 50 minutes.

41. The method of claim 37, wherein the liquid medium concentration is between about 16:1 and about 4:1 liquid medium/SO—SOS by weight.

42. The method of claim 37, wherein the fatigue resistance is characterized by a modulus recoverable to at least 92% of its value before the compression cycles were run.

43. The method of claim 37, further comprising hydrogenating the polystyrene.

44. The method of claim 37, wherein chain ends of the SO are functionalized with azide and alkyne groups, and wherein the method further comprises coupling the SO chain ends in the liquid medium to modify the SO/SOS molar ratio.

* * * * *

UNITED STATES PATENT AND TRADEMARK OFFICE
CERTIFICATE OF CORRECTION

PATENT NO. : 10,428,185 B2
APPLICATION NO. : 15/539312
DATED : October 1, 2019
INVENTOR(S) : Bailey et al.

Page 1 of 1

It is certified that error appears in the above-identified patent and that said Letters Patent is hereby corrected as shown below:

In the Claims

Claim 20, Column 64, Line 43, delete "10" and replace with --14--.

Signed and Sealed this
Seventeenth Day of March, 2020

Andrei Iancu
*Director of the United States Patent and Trademark Office*